(12) United States Patent
Lee et al.

(10) Patent No.: US 9,447,439 B2
(45) Date of Patent: Sep. 20, 2016

(54) MICROORGANISM PRODUCING 4-HYDROXYBUTYRATE AND A METHOD FOR PRODUCING 4-HYDROXYBUTYRATE IN ANAEROBIC CONDITION USING THE SAME

(71) Applicant: Samsung Electronics Co., Ltd., Suwon-si, Gyeonggi-do (KR)

(72) Inventors: Youngmin Lee, Suwon-si (KR); Wooyong Lee, Hwaseong-si (KR); Jinwoo Kim, Seoul (KR); Jaechan Park, Yongin-si (KR); Jinhwan Park, Suwon-si (KR); Hwayoung Cho, Hwaseong-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 0 days.

(21) Appl. No.: 14/468,067

(22) Filed: Aug. 25, 2014

(65) Prior Publication Data

US 2015/0056670 A1 Feb. 26, 2015

(30) Foreign Application Priority Data

Aug. 23, 2013 (KR) .......................... 10-2013-0100568

(51) Int. Cl.
| | |
|---|---|
| *C12P 7/42* | (2006.01) |
| *C12N 9/00* | (2006.01) |
| *C12P 7/46* | (2006.01) |
| *C12N 9/02* | (2006.01) |
| *C12P 17/04* | (2006.01) |

(52) U.S. Cl.
CPC ............... *C12P 7/42* (2013.01); *C12N 9/0008* (2013.01); *C12N 9/93* (2013.01); *C12P 7/46* (2013.01); *C12P 17/04* (2013.01); *C12Y 101/01027* (2013.01); *C12Y 103/05* (2013.01); *C12Y 401/01* (2013.01); *C12Y 101/01061* (2013.01); *C12Y 102/01002* (2013.01); *C12Y 102/01024* (2013.01); *C12Y 102/07003* (2013.01); *C12Y 108/01004* (2013.01); *C12Y 203/01012* (2013.01); *C12Y 208/03* (2013.01); *C12Y 604/01001* (2013.01); *Y02P 20/52* (2015.11)

(58) Field of Classification Search
IPC ......................................................... C12P 7/42
See application file for complete search history.

(56) References Cited

U.S. PATENT DOCUMENTS

| | | |
|---|---|---|
| 2010/0330634 A1 | 12/2010 | Park et al. |
| 2012/0094345 A1 | 4/2012 | Burk et al. |
| 2012/0122171 A1 | 5/2012 | Burk et al. |
| 2015/0064758 A1 | 3/2015 | Lee et al. |

FOREIGN PATENT DOCUMENTS

| | | |
|---|---|---|
| KR | 2007-0096347 A | 10/2007 |
| KR | 2015-0025482 A | 3/2015 |

OTHER PUBLICATIONS

Litsanov et al., "Towards homosuccinate fermentation: metabolic engineering of 2*Corynebacterium glutamicum* for anaerobic succinate production from 3 glucose and formate," *Appl. Environ. Microbiol.*, doi:10.1128/AEM.07790-11, pp. 1-47 (2012).

Yim et al., "Metabolic engineering of *Escherichia coli* for direct production of 1,4-butanediol," *Nature Chemical Biology*, 7: 445-452 (2011).

*Primary Examiner* — Suzanne M Noakes
(74) *Attorney, Agent, or Firm* — Leydig, Voit & Mayer, Ltd.

(57) ABSTRACT

A genetically modified microorganism comprising a polynucleotide encoding α-ketoglutarate synthase or a mutant thereof, and a polynucleotide encoding pyruvate carboxylase or a mutant thereof; wherein the genetically modified microorganism has decreased malate quinone oxidoreductase activity and/or decreased phosphoenolpyruvate carboxykinase activity compared to an unmodified microorganism of the same type, and wherein the genetically modified microorganism produces 4-hydroxybutyrate.

19 Claims, 4 Drawing Sheets

US 9,447,439 B2

MICROORGANISM PRODUCING 4-HYDROXYBUTYRATE AND A METHOD FOR PRODUCING 4-HYDROXYBUTYRATE IN ANAEROBIC CONDITION USING THE SAME

CROSS-REFERENCE TO RELATED APPLICATIONS

This application claims the benefit of Korean Patent Application No. 10-2013-0100568, filed on Aug. 23, 2013, in the Korean Intellectual Property Office, the entire disclosure of which is hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted concurrently herewith and identified as follows: One 149,196 Byte ASCII (Text) file named "718145 ST25-Revised.TXT" created on Nov. 3, 2014.

BACKGROUND

1. Field

The present disclosure relates to a genetically modified microorganism that produces 4-hydroxybutyrate and a method of producing 4-hydroxybutyrate using the genetically modified microorganism.

2. Description of the Related Art

Biodegradable polymers have been suggested as an alternative to the synthetic polymers which account for a great part of severe environmental pollution. Accordingly, various biodegradable polymers have been developed. One such biodegradable polymer is poly-β-hydroxybutyrate, which is a biodegradable polymer accumulated in a nutritionally imbalanced state by various microorganisms and has excellent properties such as biodegradability, moisture resistance, piezoelectricity, and biocompatibility. 4-hydroxybutyrate (4HB), which is one of the various types of poly-β-hydroxybutyrate, is a representative polyhydroxyalkanoate (PHA). 4HB is a substance produced as a white powder in a small quantity from wine, beef, and fruit. Many studies are conducted with regard to 4HB as a biodegradable plastic material as 4HB shows a wide range of physical properties from crystalline plastic to highly elastic rubber as 4HB is similar to polyester. 4HB for medical use is generally produced by fermentation. Although a method of producing 1,4-butandiol (1,4-BDO) from 4HB is known, it has not been commercialized yet.

4HB has been used as a starting material in producing other C4-chemicals such as 1,4-BDO and γ-butyrolactone (GBL) by methods using a microorganism. 4HB may easily be converted to various other C4-chemicals such as 1,4-BDO, GBL, and tetrahydrofuran (THF). These various chemicals are used in the chemical industries as polymer, solvent, and fine chemical intermediates.

Most C4-chemicals that are currently synthesized are derived from 1,4-butandiol or maleic anhydride, but the chemical production process needs to be improved or replaced by a newly developed process as production costs are increasing due to rising oil prices. A biological process for producing C4-chemicals is suggested as an alternative to the chemical process, but the yield of 4HB production using conventional microorganisms is low. Thus, there is a need for a mutant microorganism capable of producing 4HB, and a biological method of producing 4HB using the mutant microorganism.

SUMMARY

Provided is a genetically modified (i.e. engineered) microorganism that produces 4-hydroxybutyrate (4HB), and a method of increasing 4HB production by using the prepared strain. The genetically modified microorganism comprises a polynucleotide encoding α-ketoglutarate synthase or a mutant thereof, and a polynucleotide encoding pyruvate carboxylase or a mutant thereof; and has decreased malate quinone oxidoreductase activity and/or decreased phosphoenolpyruvate carboxykinase activity compared to an unmodified microorganism of the same type.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
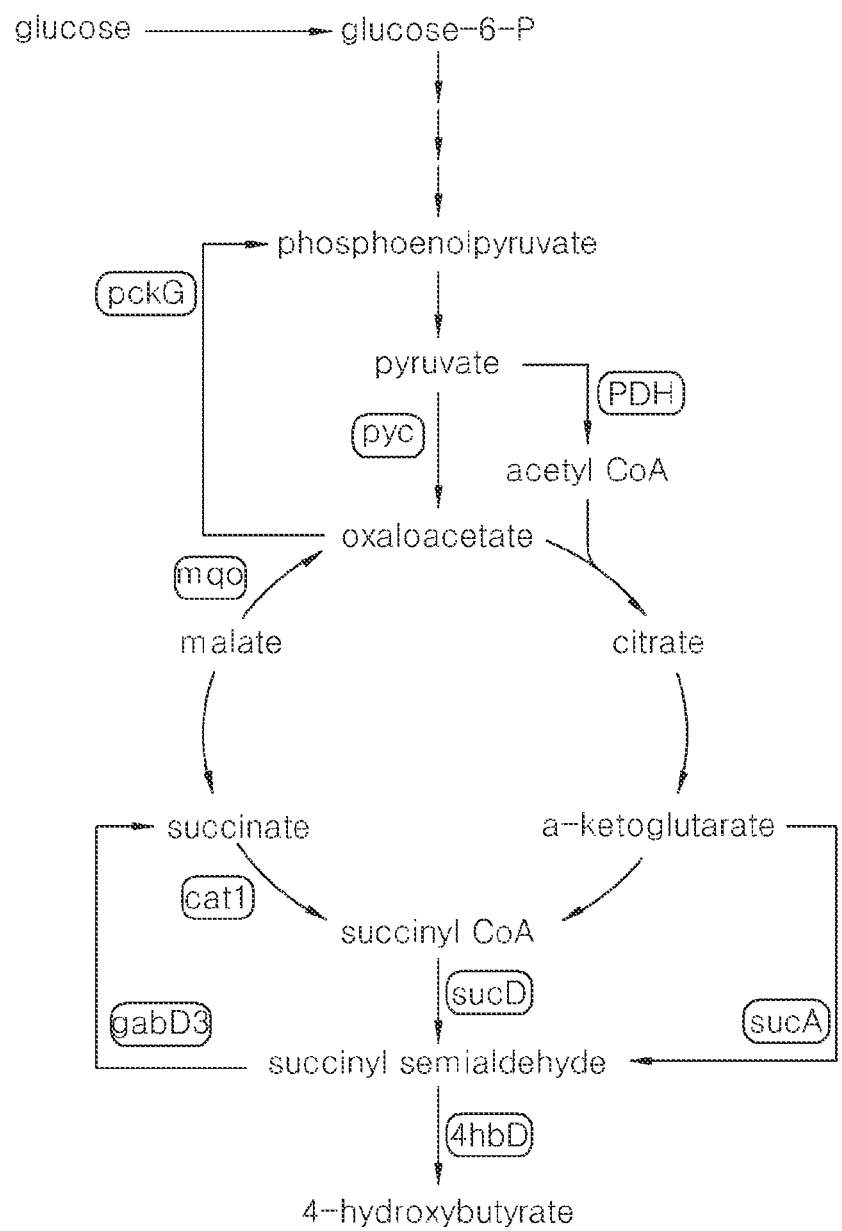
FIG. 1 is a flow chart displaying genes for alteration, deletion, and introduction in metabolic pathways and glycolysis pathways for 4HB production in a microorganism.
Figure 2:
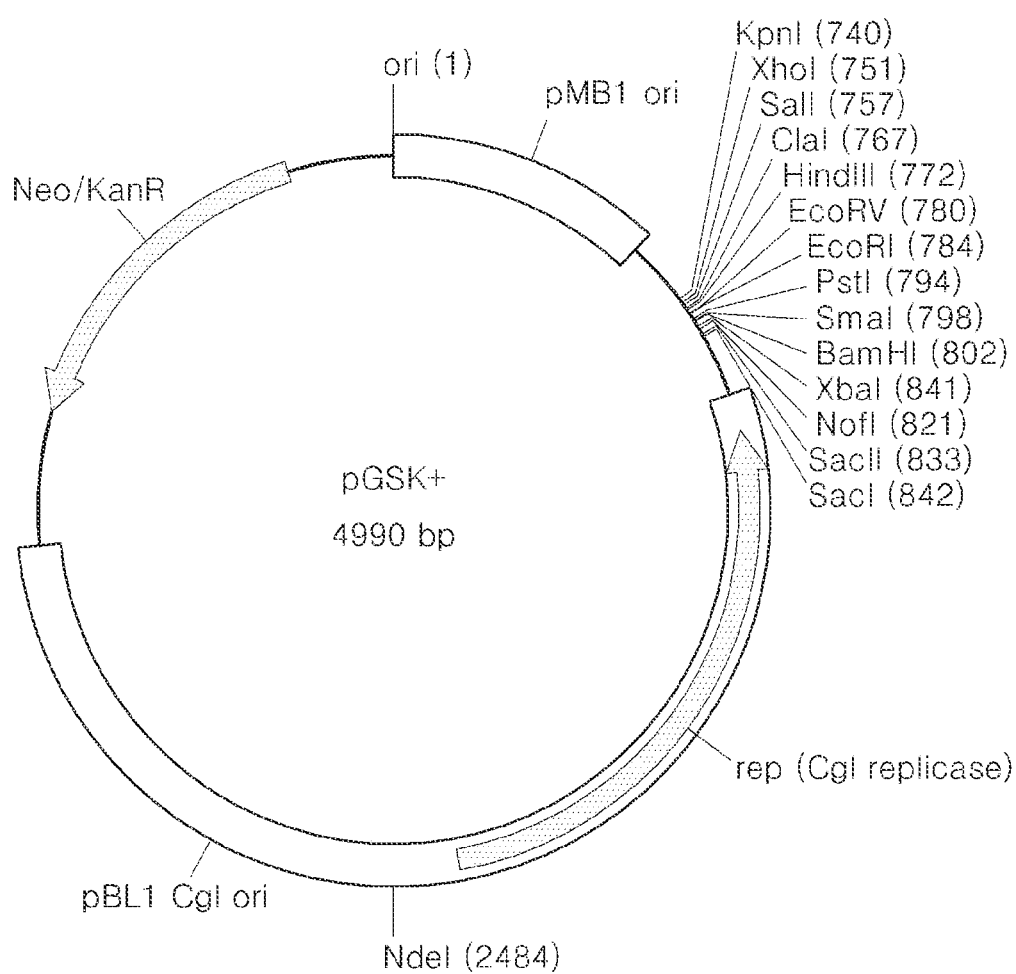
FIG. 2 is a map of the expression vector pGSK+ used in preparing a genetically modified microorganism.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items.

Provided is a genetically modified microorganism (i.e., a strain) that produces 4-hydroxybutyrate (4HB).

An embodiment of invention provides a genetically modified microorganism that produces 4HB, wherein the activity of malate quinone oxidoreductase and/or the activity of phosphoenolpyruvate carboxykinase is eliminated or decreased compared to an unmodified microorganism of the same type, and wherein the genetically modified microorganism comprises a polynucleotide encoding α-ketoglutarate synthase or a mutant thereof, and/or a polynucleotide encoding pyruvate carboxylase or a mutant thereof.

The term "unmodified microorganism of the same type" means a reference microorganism that is compared to a genetically modified microorganism comprising a subject modification. The reference microorganism refers to a wild-type microorganism or a parental microorganism. The parental microorganism refers to a microorganism that has not undergone the subject modification that the genetically modified microorganism has undergone and is genetically identical to the genetically modified microorganism except for the modification, and thus serves as a reference microorganism for the modification.

In addition, the genetically modified microorganism may be a microorganism wherein the activity of succinate semialdehyde dehydrogenase is eliminated or decreased.

In addition, the genetically modified microorganism may further include a polynucleotide encoding pyruvate dehydrogenase or a mutant thereof.

In addition, the genetically modified microorganism may further include a polynucleotide encoding formate dehydrogenase or a mutant thereof.

The strain may be a strain selected from the group consisting of lumen bacteria, *Corynebacterium* genus, *Brevibacterium* genus, and *Escherichia coli*. The strain may be *Corynebacterium glutamicum*. In particular, *Corynebacterium glutamicum* may be cultured in a wide range of culture conditions and at a high growth rate. In addition, *Corynebacterium glutamicum* is non-pathogenic and harmless to environment, as they do not produce a spore. In particular, *Corynebacterium glutamicum* is highly available in industries as it may be cultured to a concentration four times higher than that of *Escherichia coli*.

The strain capable of producing 4HB may be a strain wherein the activity of lactate dehydrogenase is eliminated or decreased compared to an unmodified microorganism of the same type. The strain capable of producing 4HB may include succinyl-CoA:coenzyme A transferase or a mutant thereof, coenzyme-dependent succinate semialdehyde dehydrogenase or a mutant thereof, and 4-hydroxybutyrate dehydrogenase or a mutant thereof.

Lactate dehydrogenase is an enzyme that catalyzes the conversion of pyruvate to lactate. The lactate dehydrogenase may include lactate dehydrogenase (Ldh), lactate dehydrogenase A (LdhA), lactate dehydrogenase B (LdhB), and lactate dehydrogenase C (LdhC). The activity of the lactate dehydrogenase may be eliminated or decreased in a genetically modified microorganism. The lactate dehydrogenase may an enzyme classified as EC.1.1.1.27. The lactate dehydrogenase may be referred to as LdhA. The genetically modified microorganism may be a microorganism wherein a gene encoding lactate dehydrogenase is inactivated or attenuated. The mutant of lactate dehydrogenase may be an enzyme having catalytic activity the same as that of lactate dehydrogenase and sequence identity of 80% or higher with amino acid sequence of a wild type lactate dehydrogenase. The mutant may be an enzyme having catalytic activity the same as that of lactate dehydrogenase and sequence identity of 85% or higher, 90% or higher, 95% or higher, or 99% or higher with amino acid sequence of a wild type lactate dehydrogenase.

The succinyl-CoA:coenzyme A transferase may be referred to as Cat1. The enzyme catalyzes the conversion of succinate to succinyl-CoA. The succinyl-CoA:coenzyme A transferase may be an enzyme classified as EC.2.8.3. The enzyme may be derived from *Corynebacterium glutamicum* or *Clostridium kluyveri*. The succinyl-CoA:coenzyme A transferase may have an amino acid sequence of SEQ ID NO: 1. A polynucleotide encoding the succinyl-CoA:coenzyme A transferase may have a nucleic acid of SEQ ID NO: 2. The mutant of the succinyl-CoA:coenzyme A transferase may be an enzyme having catalytic activity the same as that of the succinyl-CoA:coenzyme A transferase and sequence identity of 80% or higher with amino acid sequence of a wild type the succinyl-CoA:coenzyme A transferase. The mutant may be an enzyme having catalytic activity the same as that of the succinyl-CoA:coenzyme A transferase and sequence identity of 85% or higher, 90% or higher, 95% or higher, or 99% or higher with amino acid sequence of a wild type the succinyl-CoA:coenzyme A transferase.

The CoA-dependent succinate semialdehyde dehydrogenase may be referred to as SucD. The enzyme catalyzes the conversion of succinyl-CoA to succinyl semialdehyde. A polynucleotide encoding the CoA-dependent succinate semialdehyde dehydrogenase (SEQ ID NO: 3) may be derived from a *Corynebacterium glutamicum* or *Porphyromonas gingivalis*. The polynucleotide encoding the CoA-dependent succinate semialdehyde dehydrogenase may have a nucleic acid of SEQ ID NO: 4. The mutant of CoA-dependent succinate semialdehyde dehydrogenase may be an enzyme having catalytic activity the same as that of CoA-dependent succinate semialdehyde dehydrogenase and sequence identity of 80% or higher with amino acid sequence of a wild type succinate semialdehyde dehydrogenase. The mutant may be an enzyme having catalytic activity the same as that of CoA-dependent succinate semialdehyde dehydrogenase and sequence identity of 85% or higher, 90% or higher, 95% or higher, or 99% or higher with amino acid sequence of a CoA-dependent succinate semialdehyde dehydrogenase.

The 4-hydroxybutyrate dehydrogenase may be referred to as 4Hbd. The enzyme catalyzes the conversion of succinyl semialdehyde to 4HB. The enzyme may be derived from a *Corynebacterium glutamicum* or *Porphyromonas gingivalis*. The 4-hydroxybutyrate dehydrogenase may have an amino acid sequence of SEQ ID NO: 5. A polynucleotide encoding the 4-hydroxybutyrate dehydrogenase may have a nucleic acid of SEQ ID NO: 6. The mutant of 4-hydroxybutyrate dehydrogenase may be an enzyme having catalytic activity the same as that of 4-hydroxybutyrate dehydrogenase and sequence identity of 80% or higher with amino acid sequence of a wild type 4-hydroxybutyrate dehydrogenase. The mutant may be an enzyme having catalytic activity the same as that of 4-hydroxybutyrate dehydrogenase and sequence identity of 85% or higher, 90% or higher, 95% or higher, or 99% or higher with amino acid sequence of a wild type 4-hydroxybutyrate dehydrogenase.

A gene may be additionally introduced into or eliminated from a strain capable of producing 4HB. For example, activity of malate quinone oxidoreductase may be eliminated or decreased in the strain compared to an unmodified microorganism of the same type. Malate quinone oxidoreductase may be referred to as Mqo. The enzyme catalyzes the conversion of converting malate to oxaloacetate. The malate quinone oxidoreductase may have an amino acid sequence of SEQ ID NO: 17. Gene addition, substitution, or deletion may be performed in a polynucleotide encoding malate quinone oxidoreductase in order to decrease activity of malate quinone oxidoreductase. The polynucleotide encoding malate quinone oxidoreductase may be partly or totally deleted by homologous recombination. The polynucleotide encoding malate quinone oxidoreductase may have a nucleic acid sequence of SEQ ID NO: 18.

Activity of phosphoenolpyruvate carboxykinase may be eliminated or decreased in the strain compared to an unmodified microorganism of the same type. Phosphoenolpyruvate carboxykinase may be referred to as PckG. The enzyme catalyzes the conversion of converting oxaloacetate to phosphoenolpyruvate. The phosphoenolpyruvate carboxykinase may have an amino acid sequence of SEQ ID NO: 19. Gene addition, substitution, or deletion may be performed in a polynucleotide encoding phosphoenolpyruvate carboxykinase in order to decrease activity of phosphoenolpyruvate carboxykinase. The polynucleotide encoding phosphoenolpyruvate carboxykinase may be partly or totally deleted by homologous recombination. The polynucleotide encoding phosphoenolpyruvate carboxykinase may have a nucleic acid sequence of SEQ ID NO: 20.

The microorganism may include a polynucleotide encoding α-ketoglutarate synthase or a mutant thereof. α-ketoglutarate synthase may be referred to as SucA. The enzyme catalyzes the conversion of ketoglutarate to succinyl semialdehyde. The enzyme may be derived from *Corynebacterium glutamicum* or *Mycobacterium bovis*. The α-ketoglutarate synthase may have an amino acid sequence of SEQ ID NO: 7. A polynucleotide encoding the α-ketoglutarate synthase may have a nucleic acid of SEQ ID NO: 8. The mutant of α-ketoglutarate synthase is an enzyme having catalytic activity the same as that of α-ketoglutarate synthase and sequence identity of 80% or higher with amino acid sequence of a wild type α-ketoglutarate synthase. The mutant may be an enzyme having catalytic activity the same as that of α-ketoglutarate synthase and sequence identity of 85% or higher, 90% or higher, 95% or higher, or 99% or higher with amino acid sequence of a wild type α-ketoglutarate synthase.

The microorganism may include a polynucleotide encoding pyruvate carboxylase or a mutant thereof. Pyruvate carboxylase may be referred to as Pyc. The enzyme catalyzes the conversion of pyruvate to oxaloacetate. The enzyme may be derived from *Corynebacterium glutamicum* or *Escherichia coli*. The pyruvate carboxylase may have an amino acid sequence of SEQ ID NO: 9. The mutant of pyruvate carboxylase is an enzyme having catalytic activity the same as that of pyruvate carboxylase and sequence identity of 80% or higher with amino acid sequence of a wild type pyruvate carboxylase. The mutant may be an enzyme having catalytic activity the same as that of pyruvate carboxylase and sequence identity of 85% or higher, 90% or higher, 95% or higher, or 99% or higher with amino acid sequence of a wild type pyruvate carboxylase. The mutant of pyruvate carboxylase may be formed by substituting the 458th amino acid of a wild type pyruvate carboxylase. The 458th amino acid of a wild type pyruvate carboxylase may be proline. The 458th amino acid of a wild type pyruvate carboxylase may be substituted with serine (SEQ ID NO: 10). The polynucleotide encoding pyruvate carboxylase may have a nucleic acid sequence of SEQ ID NO: 11.

Activity of succinate semialdehyde dehydrogenase may be eliminated or decreased in the strain. Succinate semialdehyde dehydrogenase may be referred to as SSADH. The enzyme catalyzes the conversion of succinyl semialdehyde to succinate. The succinate semialdehyde dehydrogenase may have an amino acid sequence of SEQ ID NO:21. Gene addition, substitution, or deletion may be performed in NCgl0049, NCgl0463, or NCgl2619 gene in order to decrease activity of succinate semialdehyde dehydrogenase. The NCgl0049 polynucleotide may be partly or totally deleted by homologous recombination. The NCgl0049 polynucleotide may have a nucleic acid sequence of SEQ ID NO: 22. The NCgl0463 polynucleotide may have a nucleic acid sequence of SEQ ID NO: 23. The NCgl2619 polynucleotide may have a nucleic acid sequence of SEQ ID NO: 24.

The microorganism may include a polynucleotide encoding pyruvate dehydrogenase. The pyruvate dehydrogenase may be referred to as "pyruvate dehydrogenase complex" and also Pdh. The pyruvate dehydrogenase catalyzes the conversion of to acetyl CoA. The pyruvate dehydrogenase complex includes pyruvate dehydrogenase (E1), dihydrolipoyl transacetylase (E2), and dihydrolipoyl dehydrogenase (E3). In the pyruvate dehydrogenase, E1 is also referred to as AceE, E2 is referred to as AceF, and E3 is referred to as lpd or lpdA, depending on microorganisms.

A polynucleotide encoding the pyruvate dehydrogenase includes lpd, aceE, and aceF genes. The genes may be derived from *Corynebacterium glutamicum* or *Escherichia coli*. The lpd gene may be a polynucleotide having a nucleic acid sequence of SEQ ID NO: 12. The aceE gene may be a polynucleotide having a nucleic acid sequence of SEQ ID NO: 13. The aceF gene may be a polynucleotide having a nucleic acid sequence of SEQ ID NO: 14.

The microorganism may include a polynucleotide encoding formate dehydrogenase or a mutant thereof. Formate dehydrogenase may be referred to as Fdh. The enzyme catalyzes the conversion of formate to bicarbonate. The enzyme may be derived from *Corynebacterium glutamicum* or *Mycobacterium vaccae*. The formate dehydrogenase may have an amino acid sequence of SEQ ID NO: 15. The polynucleotide encoding formate dehydrogenase may have a nucleic acid sequence of SEQ ID NO: 16.

The polynucleotide encoding an enzyme may be introduced to a strain as it is inserted into a vector. The polynucleotide may be operably linked with a regulatory sequence. A regulatory sequence, which is a sequence regulating expression of the polynucleotide, may include a promoter, a terminator, or an enhancer.

The term "vector" refers to a DNA product including a DNA sequence operably linked with an appropriate regulation sequence capable of expressing DNA in an appropriate host cell. The vector may be a plasmid vector, a bacteriophage vector, or a cosmid vector. To operate as an expression vector, a vector may include a replication origin, a promoter, a multi-cloning site (MCS), a selection marker or a combination thereof. A replication origin gives a function to a plasmid to replicate itself independently of hose cell chromosome. A promoter operates in transcription process of an inserted foreign gene. An MCS enables a foreign gene to be inserted through various restriction enzyme sites. A selection marker verifies whether a vector has been properly introduced to a host cell. A selection includes an antibiotic-resistant gene generally used in the art. For example, a selection marker may include a gene resistant to ampicillin, gentamycin, carbenicillin, chloramphenicol, streptomycin, kanamycin, geneticin, neomycin or tetracycline. Considering the cost, ampicillin or gentamycin-resistant gene may be used.

When a vector of an embodiments uses a prokaryotic cell as host cell, a strong promoter, for example, lamda-PL promoter, trp promoter, lac promoter or T7 promoter, is included in the vector. If a vector uses a eukaryotic cell as host cell, the vector may include a promoter derived from genome of a mammal (metallothionin promoter, e.g.) or a promoter derived from a mammal virus (adenovirus late promoter, vaccinia virus 7.5K promoter, SV40 promoter, cytomegalovirus promoter or tk promoter of HSV promoter, e.g.). The promoter may be a lamda-PL promoter, trp promoter, lac promoter or T7 promoter. In this manner, a promoter is operably linked with a sequence encoding a gene.

The promoter is operably linked with a sequence encoding a gene. The term "operably linked" herein means a functional bond between a nucleic acid expression regulatory sequence (e.g. promoter, signal sequence or array at transcription regulation factor binding site, a terminator, or an enhancer) and another nucleic acid sequence. Through the functional bond, the regulatory sequence may control transcription and/or translation of a nucleotide encoding the gene.

The term "transformation" herein refers to introducing a gene to a host cell so that the gene may be expressed in the microorganism by methods known in the art (e.g., heat shock and electroporation). A transformed gene, only if the gene may be expressed in the host cell, may be any gene whether the gene is inserted into a chromosome of the host cell or the gene exists outside a chromosome. The gene, which is a polynucleotide capable of encoding a polypeptide, may be DNA or RNA. The introduction of the gene may be any type of introduction, only if the gene may be introduced into and expressed in the host cell. For example, the gene may be introduced into a host cell by an introduction in the form of an expression cassette, which is a polynucleotide structure including all factors related to the expression of the gene by itself. The expression cassette usually includes a promoter, a transcription termination signal, a ribosome binding site, and a translation termination signals operably linked with the gene. The expression cassette may be an expression vector capable of self-replication. In addition, the gene may be introduced as itself or in the form of a polynucleotide structure to a host cell and then be operably linked with a sequence related to an expression in the host cell.

Attenuation of activity of the enzyme maybe performed by substituting an endogenous gene with a gene which is altered so that enzyme activity may be weakened or deleted, by substituting a promoter of the gene with a promoter weaker than an endogenous promoter, or by deleting the gene from a chromosome. A gene encoding an enzyme may be deleted from genome of a microorganism by homologous recombination.

Another aspect relates to a method of producing C4-chemicals by culturing the genetically modified microorganism in a cell culture medium, whereby the microorganism produces a C4-chemical; and recovering the C4-chemical from the culture solution. The C4-chemicals may include succinic acid, succinate, fumaric acid, malic acid, or a C4 chemical derived therefrom. For example, production of C4-chemicals included in TCA cycle or substances derived therefrom may be increased by culturing the microorganism of an aspect. In addition, the substances derived from succinate may be 4-HB, 1,4-BDO, γ-butyrolactone (GBL) or C4 chemicals derived therefrom but are not limited thereto.

The culturing may be performed under an appropriate culture medium composition and culture conditions known in this art. The culture medium composition and culture conditions may be conveniently adjusted according to the selected microorganism. The culturing method may include batch culturing, continuous culturing, fed-batch culturing or a combination thereof. The fed-batch culturing may use a culture medium having glucose 50 g/L, corn steep liquor 10 g/L, $(NH_4)_2SO_4$ 45 g/L, UREA 4.5 g/L, $KH_2PO_4$ 0.5 g/L, $MgSO_4/7H_2O$ 0.5 g/L, $FeSO_4/7H_2O$ (10 g/L) stock 1 mL, $MnSO_4/4H_2O$ (10 g/L) stock 1 mL, beta-alanin (5 g/L) stock 1 mL, nicotinic acid (5 g/L) stock 1 mL, thiamine-HCl (5 g/L) stock 1 mL, and D-biotin (0.3 g/L) stock 1 mL. The culture condition may comprise a combination of aerobic and anaerobic conditions. For example, the genetically modified microorganism may be cultured under aerobic condition for 20 hr and subsequently, under anaerobic condition for 80 hr.

The culture medium may include various carbon sources, nitrogen sources, and trace elements. The carbon source may include a carbohydrate such as glucose, sucrose, lactose, fructose, maltose, starch, and cellulose, a lipid such as soybean oil, sunflower oil, castor oil, and coconut oil, a fatty acid such as palmitic acid, stearic acid, and linoleic acid, an organic acid such as acetic acid or a combination thereof. The culturing may be performed by using glucose as a carbon source. The nitrogen source may include an organic nitrogen source such as peptone, yeast extract, meat extract, malt extract, corn steep liquid, and soybean, an inorganic nitrogen source such as urea, ammonium sulfate, ammonium chloride, ammonium phosphate, ammonium carbonate, and ammonium nitrate or a combination thereof. The culture medium may include as a phosphorous source, for example, potassium dihydrogen phosphate, dipotassium phosphate, a sodium-containing salt corresponding to potassium dihydrogen phosphate, and dipotassium phosphate, and a metal salt such as magnesium sulfate and iron sulfate. The culture medium or an individual component may be added to the culture in a batch mode or a continuous mode.

In addition, pH of the culture may be adjusted during the culturing by adding a compound such as ammonium hydroxide, potassium hydroxide, ammonia, phosphoric acid or sulfuric acid to the culture in an appropriate mode. In addition, bubble formation may be repressed by using an endoplasmic reticulum such as fatty acid polyglycol ester.

The microorganism may be cultured under anaerobic conditions. The term "anaerobic conditions" herein refers to a state wherein oxygen content is lower than that of normal atmospheric state. Anaerobic conditions may be formed, for example, by supplying carbon dioxide or nitrogen at a flow rate range from about 0.1 vvm (Volume per Volume per Minute) to about 0.4 vvm, from about 0.2 vvm to about 0.3 vvm or at a flow rate of 0.25 vvm. In addition, anaerobic conditions may be formed by setting an aeration rate in the range from about 0 vvm and to 0.4 vvm, from about 0.1 vvm to about 0.3 vvm or from 0.15 vvm to about 0.25 vvm.

The method of producing C4-chemicals includes recovering of the produced C4-chemicals from the culture. The produced C4-chemicals may be succinic acid, succinate, fumaric acid, malic acid or a C4-chemical derived therefrom. According to one embodiment, the produced C4-chemicals may be 4-HB, 1,4-BDO, GBL or a C4-chemical derived therefrom. For example, the recovery of 4-HB may be performed by using known separation and purification methods. The recovery may be performed by centrifugation, ion exchange chromatography, filtration, precipitation or a combination thereof. Recovery of C4-chemicals, for example, recovery of succinic acid, 4HB, or GBL may be performed by a method known in this art including filtration of culture solution.

In addition, the method of producing C4-chemicals may be used to produce other various organic compounds by converting the C4-chemicals to other organic chemicals. A substrate structurally related to 4-HB may be synthesized by chemically converting the 4-HB yielded in the method described above. According to one embodiment, gamma butyrolactone (GBL) may be yielded by reacting 4-HB at about 100° C. to 200° C. in the presence of a strong acid and then distilling the reactant. The yielded GBL may be converted to N-methyl pyrrolidone (NMP) by amination using an aminating agent, for example, methylamine. In addition, the yielded GBL may be selectively converted to tetrahydrofuran (THF), 1,4-BDO or butanol by hydrogenation using a metal-containing catalyst, for example, Ru or Pd.

The poly-4-hydroxybutyrate may be yielded by biologically converting the produced 4-HB. The biological conversion may be achieved by polyhydroxyalkanoate synthase, 4-HB-CoA:coenzyme A transferase or a combination thereof.

As described above, according to the one or more of the above embodiments, yield of 4HB production was improved by performing additional genetic engineering in a genetically modified microorganism that produces 4HB. In particular, activity of enzymes involved in various metabolic pathways was altered, and a genetically modified microorganism capable of producing 4HB at the optimal yield was developed by a combination of various genetic mutations. As the genetically modified microorganism having increased 4HB productivity may produce 4HB at a high yield by anaerobic fermentation, the strain may be very useful in industries.

A genetically modified microorganism capable of producing 4HB at a high efficiency in anaerobic conditions may be effectively used in 4HB production. As 4HB is a compound highly useful in industries, 4HB productivity increase in the strain may increase utility of 4HB by reducing unit price of 4HB production. Therefore, the transformed microorganism may be very useful in industries.

It should be understood that the exemplary embodiments described therein should be considered in a descriptive sense only and not for purposes of limitation. Descriptions of features or aspects within each embodiment should typically be considered as available for other similar features or aspects in other embodiments.

Example 1

Preparation of Transformed Strain 1.1 Preparation of CGL (Δldh) Strain
(1) Preparation of Replacement Vector To prevent excessive lactate accumulation in natural *Corynebacterium* during anaerobic fermentation, a gene (SEQ ID NO: 42) expressing L-lactate dehydrogenase (NCgl2810) in the strain was eliminated. An open reading frame (ORF) region of 230 bp in the gene was eliminated by gene substitution. Sequence of the eliminated region is shown in SEQ ID NO: 29.

An upstream region corresponding to first 200 bp of ldhA gene was amplified by PCR using genome DNA of CGL ATCC 13032 as a template and using ldhA_up_5' (SEQ ID NO:25) and ldhA_up_3' (SEQ ID NO: 26) primer sets. A downstream region corresponding to last 200 bp of ldhA gene was amplified by PCR using primer sets ldhA_down_5' (SEQ ID NO:27) and ldhA_down_3' (SEQ ID NO:28). The PCR amplification was performed by repeating, 30 times, a cycle including a denaturation step at 95° C. for 30 seconds, an annealing step at 55° C. for 30 seconds, and an extension step at 72° C. for 30 seconds. All the PCR amplifications hereinafter were performed under the same conditions. Afterward, flanking regions upstream and downstream from ldhA gene was overlapped with an extended region of an oligonucleotide and linked with each other by using 16 bp In-Fusion® HD Cloning Kit (cat no. 639691 manufactured by Clontech). The linked regions upstream and downstream from the ldhA product were ligated with pK19mobsacB (obtained from ATCC 87098) at BamHI and SalI restriction enzyme sites. As a result, pK19mobsacB-Δldh was obtained.

(2) Preparation of CGL (Δldh) Strain

The obtained plasmid, pK19mobsacB-ΔldhA, was used to delete a corresponding gene in CGL by homologous recombination according to Schafer et al. (1994). The pK19mobsacB-Δldh vector was introduced to CGL ATCC13032 bp electroporation. The strain wherein the vector was introduced was cultured at 30° C. by streaking the strain on *lactobacillus* selection (LBHIS) culture medium including kanamycin 25 µg/ml. The LBHIS culture medium includes brain-heart infusion broth 18.5 g/L, 0.5 M sorbitol, 5 g/L bacto-tryptone, 2.5 g/L bacto-yeast extract, 5 g/L NaCl, and 18 g/L bacto-agar. Hereinafter, composition of LBHIS medium is the same. The colony was streaked on LB-sucrose culture medium and cultured at 30° C. Then, only the colonies wherein double crossing-over occurred were selected. Gene deletion was verified by PCR using primer sets (SEQ ID NO: 25 and SEQ ID NO: 28). The obtained strain was named as CGL(Δldh).

TABLE 1

| SEQ ID NO | Sequence |
|---|---|
| 25 | 5'-GCAGGCATGCAAGCTTCTAGTCTGGGGAGCGAAACC-3' |
| 26 | 5'-GAGCTCAGTCAGTCATGGACGCCACGAGGAAGATG-3' |
| 27 | 5'-TGACTGACTGAGCTCCTGGACAAAGACCCAGAGCT-3' |
| 28 | 5'-GGCCAGTGCCAAGCTTTTGCGGGCACCAACGTAATG-3' |

1.2 Preparation of Strain Capable of Producing 4HB

The CGL(Δldh) strain prepared in Example 1.1 was genetically engineered further so that the strain may become capable of producing 4HB. In order to attenuate NCgl0049 gene, a polynucleotide encoding succinyl-CoA:coenzyme A transferase, CoA-dependent succinate semialdehyde dehydrogenase, and 4-hydroxybutyrate dehydrogenase (SEQ ID NO:45) was introduced by substituting the gene at the NCgl0049 gene position. The gene was introduced to a *Corynebacterium* using pK19mobsacB vector (ATCC87098). In other words, sequences of the regions upstream and downstream of the NCgl0049 gene and sequence of the cat1, sucD, and 4hbd gene regions (SEQ ID NO:45) were synthesized and ligated with pK19mobsacB at XbaI and NheI restriction enzyme sites.

The obtained plasmid was used to substitute the NCgl0049 gene with the synthesized cat1, sucD, and 4hbd genes by homologous recombination according to Schafer et al. (1994). Deletion of NCgl0049 and introduction of cat1, sucD, and 4hbd genes were verified by PCR using primer sets (SEQ ID NO: 43 and SEQ ID NO: 44). The obtained strain was named as C011.

TABLE 2

| SEQ ID NO | Sequence |
|---|---|
| 43 | 5'-ATT CGG TGA GGA ATC CGG CGG TG-3' |
| 44 | 5'-CTA TGA GAC AGT CGT CCT GTA CCC AT-3' |

1.3 Preparation of Gene-Deleted Strain for Efficient Production of 4HB 1.3.1 Deletion of Malate Quinone Oxidoreductase Gene (1) Preparation of Replacement Vector An upstream region corresponding to first 200 bp of malate quinone oxidoreductase gene was amplified by PCR using genome DNA of CGL ATCC 13032 as a template and using primer sets (SEQ ID NO: 30 and SEQ ID NO: 31). A downstream region corresponding to last 200 bp of malate quinone oxidoreductase gene was amplified by PCR using primer sets (SEQ ID NO: 32 and SEQ ID NO: 33). Afterward, flanking regions upstream and downstream from malate quinone oxidoreductase gene was overlapped with an extended region of an oligonucleotide and linked with each other by using 16 bp In-Fusion® HD Cloning Kit (cat no. 639691 manufactured by Clontech). The linked regions upstream and downstream from the malate quinone oxidoreductase product were ligated with pK19mobsacB at BamHI and SalI restriction enzyme sites. As a result, pK19mobsacB-Δmqo was obtained.

(2) Preparation of CGL (ΔLdh ΔMqo) Strain

In the C011 strain prepared in Example 1.2), expression of malate quinone oxidoreductase having an amino acid sequence of SEQ ID NO: 17 was additionally repressed. For this, a polynucleotide having a nucleic acid sequence of SEQ ID NO: 18 was deleted by homologous recombination. The obtained plasmid, pK19mobsacB-Δmqo, was used to delete a corresponding gene in CGL C011 by homologous recombination according to Schafer et al. (1994).ABbrevdge deletion was verified by PCR using primer sets (SEQ ID NO: 28 and SEQ ID NO: 31).

1.3.2. Deletion of Phosphoenolpyruvate Carboxykinase (1) Preparation of Replacement Vector An upstream region corresponding to first 200 bp of phosphoenolpyruvate carboxykinase gene was amplified by PCR using genome DNA of CGL ATCC 13032 as a template and using primer sets (SEQ ID NO: 34 and SEQ ID NO: 35). A downstream region corresponding to last 200 bp of phosphoenolpyruvate carboxykinase gene was amplified by PCR using primer sets (SEQ ID NO: 36 and SEQ ID NO: 37). Afterward, flanking regions upstream and downstream from phosphoenolpyruvate carboxykinase gene was overlapped with an extended region of an oligonucleotide and linked with each other by using 16 bp In-Fusion® HD Cloning Kit (cat no. 639691 manufactured by Clontech). The linked regions upstream and downstream from the phosphoenolpyruvate carboxykinase product were ligated with pK19mobsacB at BamHI and SalI restriction enzyme sites. As a result, pK19mobsacB-pckG was obtained.

(2) Preparation of CGL (Δldh ΔpckG) Strain

Expression of phosphoenolpyruvate carboxykinase having an amino acid sequence of SEQ ID NO: 19 was additionally repressed. For this, a polynucleotide having a nucleic acid sequence of SEQ ID NO: 20 was deleted by homologous recombination. The obtained plasmid, the vector prepared above, pK19mobsacB (ATCC 87098), was used to delete a corresponding gene. Specifically, pckG gene was deleted by homologous recombination according to Schafer et al. (1994) by introducing the plasmid prepared above, pK19mobsacB-ΔpckG, into C011 (Δmqo) strain. Gene deletion was verified by PCR using primer sets (SEQ ID NO: 34 and SEQ ID NO: 37). The obtained strain was named as C011 (ΔmqoΔpckG).

TABLE 3

| SEQ ID NO | Sequence |
| --- | --- |
| 30 | 5'-CTGCAGGTCGACTCTAGAGAAGAAGTAGTCCGTCATGCCGTGAACC-3' |
| 31 | 5'-TAGAAGATTATTTTTGACTGACGCGTGGGGCG-3' |
| 32 | 5'-GTCAAAAATAATCTTCTAACTGCTTTCTTTAAAGCACCCG-3' |
| 33 | 5'-CTCGGTACCCGGGGATCCTCTTAAAGCCTGAGATAGCGAGTTCCA-3' |
| 34 | 5'-GCTCTAGAGTCATGTATTTAGGTAGGGC-3' |
| 35 | 5'-ATCTGAAAGCATGCATTTGCAACGACACCAAGT-3' |
| 36 | 5'-GTTGCAAATGCATGCTTTCAGATACAGAACTAG-3' |
| 37 | 5'-GCTCTAGACAGTCGTTGAACTCAGGT-3' |

1.4. Preparation of Gene-Introduced Strain for Efficient Production of 4HB 1.4.1. Introduction of Pyruvate Carboxylase Gene In an amino acid sequence of pyruvate carboxylase of the strain prepared in Examples 1.2 or 1.3, proline-458 was additionally substituted with serine. Specifically, the substitution was performed by using primers SEQ ID NO: 38 to 41.

An upstream region corresponding to first 200 bp from the proline amino acid position of pyruvate carboxylase was amplified by PCR using primer sets (SEQ ID NO: 38 and SEQ ID NO: 39). A downstream region from the proline amino acid position of pyruvate carboxylase was amplified by PCR using primer sets (SEQ ID NO: 40 and SEQ ID NO: 41). Afterward, the upstream and downstream regions substituting proline with serine in pyruvate carboxylase were overlapped with an extended region of an oligonucleotide and linked with each other by using 16 bp In-Fusion® HD Cloning Kit (cat no. 639691 manufactured by Clontech). The linked regions upstream and downstream from the phosphoenolpyruvate carboxykinase product were ligated with pK19mobsacB at BamHI and SalI restriction enzyme sites.

The obtained plasmid pK19mobsacB-mutated pyc$^{P458S}$ was introduced to the C011 (ΔmqoΔpckG) strain by homologous recombination according to Schafer et al. (1994). Gene introduction was verified by PCR using primer sets (SEQ ID NO: 38 and SEQ ID NO:41). The obtained strain was named as C011 (ΔmqoΔpckG pyc$^{P458S}$).

TABLE 4

| SEQ ID NO | Sequence |
|---|---|
| 38 | 5'-GCTCTAGATTGAGCACACCGTGACT-3' |
| 39 | 5'-CCGGATTCATTGCCGATCAC<u>T</u>C-3' |
| 40 | 5'-GCTCTAGACTGTCCCACGGATCCTCAAA-3' |
| 41 | 5'-CTGAAGGAGGTGCG<u>A</u>GTGA-3' |

1.4.2. Introduction of α-Ketoglutarate Synthase Gene

In order to introduce α-ketoglutarate synthase gene sucA, pK19 mobsacB-sucA was prepared by introducing a synthesized polynucleotide (SEQ ID NO:46) encoding α-ketoglutarate synthase to pK19mobsacB (ATCC 87098) vector cleaved by XbaI and NheI. The obtained plasmid pK19mobsacB-sucA was introduced to the C011 (ΔmqoΔpckG pyc$^{P458S}$) strain by homologous recombination according to Schafer et al. (1994). Gene introduction was verified by PCR using primer sets (SEQ ID NO: 54 and SEQ ID NO: 55). The obtained strain was named as C098.

1.4.3. Introduction of Pyruvate Dehydrogenase (1) Preparation of pGST1 Vector

Four PCR products were obtained by using Phusion High-Fidelity DNA Polymerase (New England Biolabs, cat.# M0530). PCR was performed by using CGL promoter screening vector pET2 (GenBank accession number: AJ885178.1) as a template and using primer sequences MD-616 (SEQ ID NO: 56) and MD-618 (SEQ ID NO: 57), and using primer sequences MD-615 (SEQ ID NO: 58) and MD-617 (SEQ ID NO: 59). PCR was performed by using mammalian fluorescence protein expression vector pEGFP-C1 (Clonetech) as a template and using primer sequences MD-619 (SEQ ID NO: 60) and MD-620 (SEQ ID NO: 61). PCR was performed by using E. coli cloning vector pBluescriptII SK+ as a template and using primer sequences LacZa-NR (SEQ ID NO: 62) and MD-404 (SEQ ID NO: 63). Each of the PCR products of 3010 bp, 854 bp, 809 bp, and 385 bp was cloned to a circular plasmid by In-Fusion EcoDry PCR Cloning Kit (Clonetech, cat.#639690) method.

The cloned vector was transformed to One Shot TOP10 Chemically Competent Cell (Invitrogen, cat.# C4040-06), which was then cultured in LB culture medium including kanamycin 25 mg/L. Growing colonies were selected, and vectors were recovered from selected colonies. Then, the vector sequences were verified through full sequence analysis. The vector was named as pGSK+. To prepare a CGL shuttle vector including a transcription terminator and a 3' untranslated region (UTR), a 3'UTR of CGL gltA (NCgl0795) and a rho-independent terminator of rrnB of E. coli rrnB were inserted to the pGSK+ vector. A 108 bp PCR fragment of gltA 3'UTR was obtained by performing PCR using CGL (ATCC13032) genome DNA as a template with the primer sequences MD-627 (SEQ ID NO: 64) and MD-628 (SEQ ID NO: 65).

In addition, an rrnB transcription terminator 292 bp PCR product was obtained by performing PCR using E. coli (MG1655) genome DNA as a template with the primer sequences MD-629 (SEQ ID NO: 66) and MD-630 (SEQ ID NO: 67). The two amplified fragments were inserted to SacI digested pGSK+ by using In-Fusion EcoDry PCR Cloning Kit (Clonetech, cat.#639690). The cloned vector was transformed to One Shot TOP10 Chemically Competent Cell (Invitrogen, cat.# C4040-06), which was then cultured in LB culture medium including kanamycin 25 mg/L. Growing colonies were selected, and vectors were recovered from selected colonies. Then, the vector sequences were verified through full sequence analysis. The vector was named as pGST1.

A CGL shuttle vector wherein each gene of E. coli Pdh complex is over-expressed under NCgl1929 promoter was prepared. 206 bp, 1454 bp, 2694 bp, and 1935 bp DNA fragments were obtained by performing PCR using CGL NCgl1929 promoter, Ec.lpd open reading frame (SEQ ID NO: 53) encoding E. coli dihydrolipoamide dehydrogenase (SEQ ID NO: 52) next to natural ribosome binding site, Ec.aceE open reading frame (SEQ ID NO: 49) encoding E. coli pyruvate dehydrogenase (SEQ ID NO: 48) next to natural ribosome binding site, and Ec.aceF open reading frame (SEQ ID NO: 51) encoding E. coli dihydrolipoamide acetyltransferase (SEQ ID NO:50) next to natural ribosome binding site, with primers J0180 (SEQ ID NO: 68) and MD-1081 (SEQ ID NO: 69), MD-1082 (SEQ ID NO: 70) and MD-1083 (SEQ ID NO: 71), MD-1084 (SEQ ID NO: 72) and MD-1085 (SEQ ID NO: 73), and MD-1086 (SEQ ID NO: 74) and MD-1087 (SEQ ID NO: 55), respectively.

The DNA fragments were ligated with KpnI/XbaI digested pGST1 vector using In-Fusion EcoDry PCR Cloning Kit (Clonetech, cat.#639690). The cloned vector was transformed to One Shot TOP10 Chemically Competent Cell (Invitrogen, cat.# C4040-06), which was then cultured in LB culture medium including kanamycin 25 mg/L. Vectors were recovered from the colonies. Then, the vector preparation was verified through full sequence analysis. The vector was named as MD0376. C158 strain was obtained by transforming the MD0376 vector in the form of a vector to C098 strain.

1.4.4 Introduction of Formate Dehydrogenase Gene

In order to introduce formate dehydrogenase gene, pK19 mobsacB-fdh was prepared by introducing a synthesized polynucleotide (SEQ ID NO: 47) encoding synthesized formate dehydrogenase to pK19mobsacB (ATCC 87098) vector cleaved by BamHI and EcoRI. The obtained plasmid pK19mobsacB-fdh was introduced to the C098 strain by homologous recombination according to Schafer et al. (1994). Gene introduction was verified by PCR using primer sets (SEQ ID NO: 76 and SEQ ID NO: 77). The obtained strain was named as C209.

TABLE 5

| Name of strain | Genotype |
|---|---|
| CGL(Δldh) | ATCC13032 Δldh |
| C011 | ATCC13032 Δldh, ΔNcgl0049, cat1, sucD, 4hbD |
| C098 | ATCC13032 Δldh, ΔNcgl0049, cat1, sucD, 4hbD, Δmqo, ΔpckG, pyc$^{P458S}$, sucA |
| C158 | ATCC13032 Δldh, ΔNcgl0049, cat1, sucD, 4hbD, Δmqo, ΔpckG, pyc$^{P458S}$, sucA, MD0376 |
| C209 | ATCC13032 Δldh, ΔNcgl0049, cat1, sucD, 4hbD, Δmqo, ΔpckG, pyc$^{P458S}$, sucA, fdh |

Example 2

Production of Various C4 Chemicals Using Transformed Strains

Each of the various CGL strains prepared in Example 1 was fermented in a fermenter at 30° C. Glucose was used as a carbon source. Fermentation was performed in anaerobic conditions for producing various C4 chemicals. Specifically, fed-batch fermentation was performed. The culture medium included glucose 50 g/L, corn steep liquor 10 g/L, $(NH_4)_2SO_4$ 45 g/L, urea 4.5 g/L, $KH_2PO_4$ 0.5 g/L, $MgSO_4/7H_2O$ 0.5 g/L, $FeSO_4/7H_2O$ (10 g/L) stock 1 mL, $MnSO_4/4H_2O$ (10 g/L) stock 1 mL, beta-ALANIN (5 g/L) stock 1 mL, nicotinic acid (5 g/L) stock 1 mL, thiamine-HCl (5 g/L) stock 1 mL, and D-Biotin (0.3 g/L) stock 1 mL. Fermentation was performed by supplying oxygen until $OD_{600}$ 80, and then by blocking oxygen supply for 100 hours.

Figure 3:
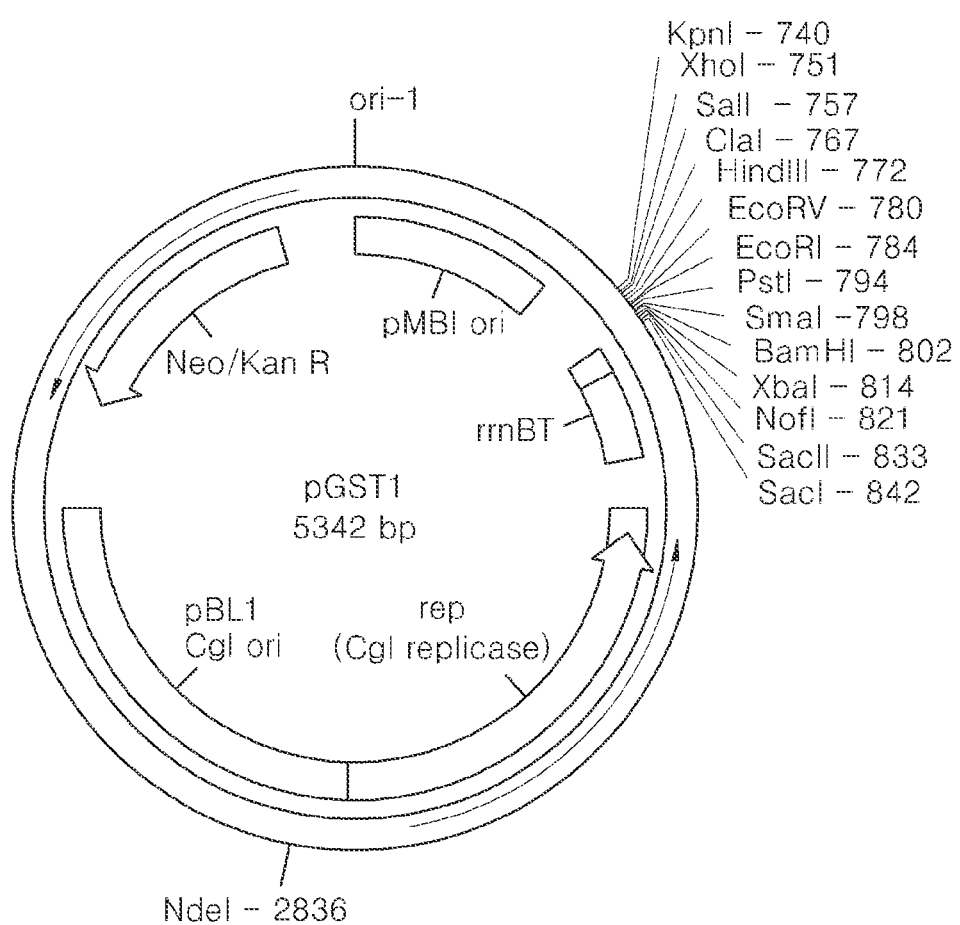
FIG. 3 is a map of the expression vector pGST1 used in preparing a genetically modified microorganism.
Figure 4:
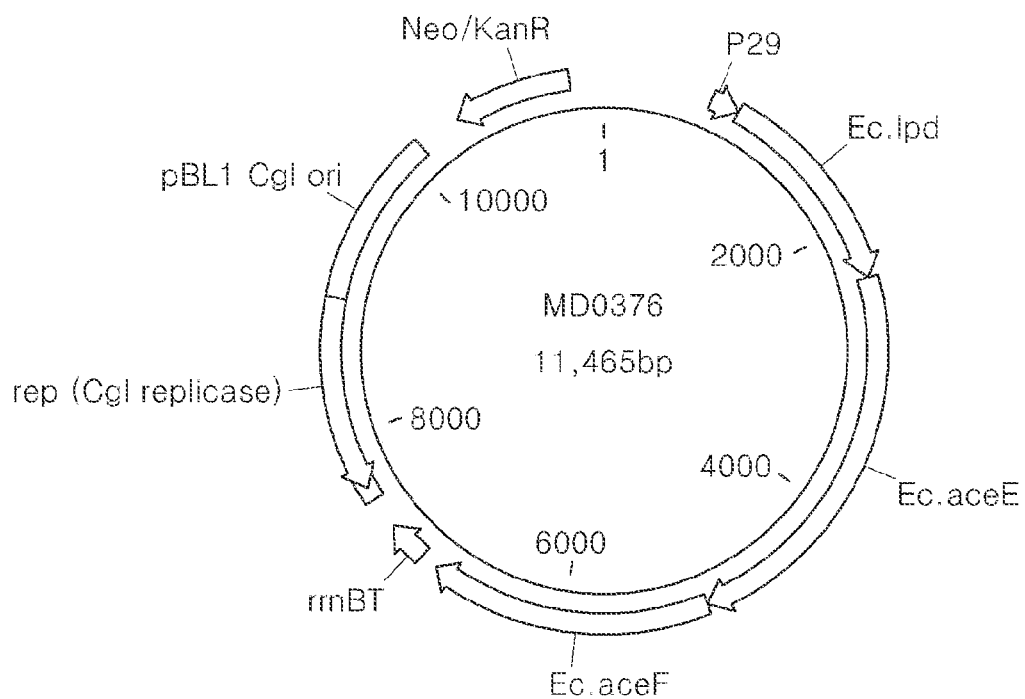
FIG. 4 is a map of the expression vector MD0376 used in preparing a genetically modified microorganism.
Figure 5:
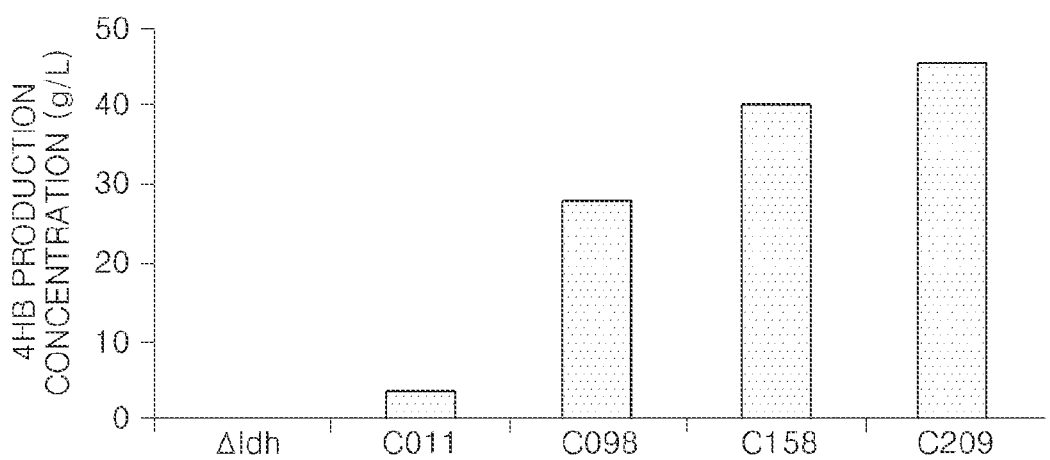
FIG. 5 is a graph comparing 4HB production concentration between the basic *Corynebacteria* strain and a genetically engineered strain.

4HB production of the strains was verified in the conditions. The basic C011 strain was verified to produce 4HB of 4.0 g/L. The additionally transformed strain C098, which was fermented in the conditions the same as those of the C011 strain, produced 28.4 g/L 4HB, which was 7.1 times the 4HB production of the C011 strain (Refer to Table 6 and FIG. 3). In addition, the C158 strain produced 40.5 g/L 4HB, which was 10.1 times and 1.4 times the 4HB production of the C011 strain and the C098 strain, respectively (Refer to Table 6 and FIG. 3). In addition, the C158 strain produced 45.7 g/L 4HB, which was 11.4 times and 1.6 times the 4HB production of the C011 strain and the C098 strain, respectively (Refer to Table 6 and FIG. 3). Under the same condition, the concentrations of succinic acid and GBL produced by the C029 strain were also measured. The C029 strain produced 12.7 g/L succinic acid and 0.3 g/L GBL, while the Δldh strain did not produce succinic acid or GBL.

TABLE 6

| Strain | 4HB Production (g/L) |
|---|---|
| Δldh | 0 |
| C011 | 4 |
| C098 | 28.4 |
| C158 | 40.5 |
| C209 | 45.7 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

What is claimed is:

1. A genetically modified microorganism comprising
a polynucleotide encoding exogenous α-ketoglutarate synthase, and
a polynucleotide encoding endogenous pyruvate carboxylase or a mutant thereof;
wherein the genetically modified microorganism has decreased malate quinone oxidoreductase activity, decreased phosphoenolpyruvate carboxykinase activity, or a combination thereof, compared to an unmodified microorganism of the same type,
wherein the genetically modified microorganism produces 4-hydroxybutyrate, and
wherein the genetically modified microorganism is a strain selected from the group consisting of lumen bacteria, *Corynebacterium* genus, *Brevibacterium* genus, and *Escherichia coli*.

2. The genetically modified microorganism of claim 1, wherein the microorganism comprises a polynucleotide encoding succinyl-CoA:coenzyme A transferase or a mutant thereof, a polynucleotide encoding coenzyme A-dependent succinate semialdehyde dehydrogenase or a mutant thereof, and a polynucleotide encoding 4-hydroxybutyrate dehydrogenase or a mutant thereof.

3. The genetically modified microorganism of claim 1, wherein the microorganism has decreased succinate semialdehyde dehydrogenase activity compared to an unmodified microorganism of the same type.

4. The genetically modified microorganism of claim 1, wherein one or more of NCg10049, NCg10463, and NCg12619 genes in the microorganism has an addition, substitution, or deletion mutation that eliminates succinate semialdehyde dehydrogenase activity, wherein the NCg10049 gene comprises the nucleic acid sequence of SEQ ID NO: 22, the NCg10463 gene comprises the nucleic acid sequence of SEQ ID NO: 23, and the NCg12619 gene comprises the nucleic acid sequence of SEQ ID NO: 24.

5. The genetically modified microorganism of claim 1, wherein the microorganism additionally comprises a polynucleotide encoding pyruvate dehydrogenase or a mutant thereof.

6. The genetically modified microorganism of claim 1, wherein the microorganism additionally comprises a gene encoding dihydrolipoyl dehydrogenase (E3), a gene encoding pyruvate dehydrogenase (E1), and a gene encoding dihydrolipoyl transacetylase (E2).

7. The genetically modified microorganism of claim 6, wherein the gene encoding dihydrolipoyl dehydrogenase (E3) comprises the nucleic acid sequence of SEQ ID NO: 12, the gene encoding pyruvate dehydrogenase (E1) comprises the nucleic acid sequence of SEQ ID NO: 13, and the gene dihydrolipoyl transacetylase (E2) comprises the nucleic acid sequence of SEQ ID NO: 14.

8. The genetically modified microorganism of claim 1, wherein the microorganism additionally comprises a polynucleotide encoding formate dehydrogenase or a mutant thereof.

9. The genetically modified microorganism of claim 1, wherein the microorganism is a strain of the *Corynebacterium* genus.

10. The genetically modified microorganism of claim 9, wherein the strain of *Corynebacterium* genus is *Corynebacterium glutamicum*.

11. The genetically modified microorganism of claim 1, wherein the pyruvate carboxylase comprises the amino acid sequence of SEQ ID NO: 9.

12. The genetically modified microorganism of claim 1, wherein the mutant pyruvate carboxylase comprises the amino acid sequence of SEQ ID NO: 10.

13. The genetically modified microorganism of claim 1, wherein the α-ketoglutarate synthase comprises the amino acid sequence of SEQ ID NO: 7.

14. The genetically modified microorganism of claim 2, wherein the succinyl-CoA:coenzyme A transferase comprises the amino acid sequence of SEQ ID NO: 1, the CoA-dependent succinate semialdehyde dehydrogenase comprises the amino acid sequence of SEQ ID NO: 3, and the 4-hydroxybutyrate dehydrogenase comprises the amino acid sequence of SEQ ID NO: 5.

15. The genetically modified microorganism of claim 8, wherein the formate dehydrogenase comprises the amino acid sequence of SEQ ID NO: 15.

16. A method of producing a C4-chemical comprising:

culturing the genetically modified microorganism of claim 1 in a cell culture medium, whereby the microorganism produces a C4-chemical; and recovering the C4-chemical from the cell culture medium.

17. The method of claim 16, wherein the C4-chemical is 4-hydroxybutyrate.

18. The method of claim 16, wherein the genetically modified microorganism additionally comprises a polynucleotide encoding pyruvate dehydrogenase or a mutant thereof and a polynucleotide encoding formate dehydrogenase or a mutant thereof.

19. The method of claim 18, wherein the C4-chemical is selected from the group consisting of succinic acid, 4-hydroxybutyrate, and gamma butyrolactone.

* * * * *

SEQUENCE LISTING

```
<160> NUMBER OF SEQ ID NOS: 77

<210> SEQ ID NO 1
<211> LENGTH: 538
<212> TYPE: PRT
<213> ORGANISM: Artificial Sequence
<220> FEATURE:
<223> OTHER INFORMATION: Synthetic (Cat1 enzyme)

<400> SEQUENCE: 1

Met Ser Lys Gly Ile Lys Asn Ser Gln Leu Lys Lys Lys Asn Val Lys
1               5                   10                  15

Ala Ser Asn Val Ala Glu Lys Ile Glu Glu Lys Val Glu Lys Thr Asp
            20                  25                  30

Lys Val Val Glu Lys Ala Ala Glu Val Thr Glu Lys Arg Ile Arg Asn
        35                  40                  45

Leu Lys Leu Gln Glu Lys Val Val Thr Ala Asp Val Ala Ala Asp Met
    50                  55                  60

Ile Glu Asn Gly Met Ile Val Ala Ile Ser Gly Phe Thr Pro Ser Gly
```

```
                65                  70                  75                  80
        Tyr Pro Lys Glu Val Pro Lys Ala Leu Thr Lys Lys Val Asn Ala Leu
                        85                  90                  95
        Glu Glu Glu Phe Lys Val Thr Leu Tyr Thr Gly Ser Ser Thr Gly Ala
                       100                 105                 110
        Asp Ile Asp Gly Glu Trp Ala Lys Ala Gly Ile Ile Glu Arg Arg Ile
                       115                 120                 125
        Pro Tyr Gln Thr Asn Ser Asp Met Arg Lys Lys Ile Asn Asp Gly Ser
                       130                 135                 140
        Ile Lys Tyr Ala Asp Met His Leu Ser His Met Ala Gln Tyr Ile Asn
        145                 150                 155                 160
        Tyr Ser Val Ile Pro Lys Val Asp Ile Ala Ile Glu Ala Val Ala
                       165                 170                 175
        Ile Thr Glu Glu Gly Asp Ile Ile Pro Ser Thr Gly Ile Gly Asn Thr
                       180                 185                 190
        Ala Thr Phe Val Glu Asn Ala Asp Lys Val Ile Val Glu Ile Asn Glu
                       195                 200                 205
        Ala Gln Pro Leu Glu Leu Glu Gly Met Ala Asp Ile Tyr Thr Leu Lys
                       210                 215                 220
        Asn Pro Pro Arg Arg Glu Pro Ile Pro Ile Val Asn Ala Gly Asn Arg
        225                 230                 235                 240
        Ile Gly Thr Thr Tyr Val Thr Cys Gly Ser Glu Lys Ile Cys Ala Ile
                       245                 250                 255
        Val Met Thr Asn Thr Gln Asp Lys Thr Arg Pro Leu Thr Glu Val Ser
                       260                 265                 270
        Pro Val Ser Gln Ala Ile Ser Asp Asn Leu Ile Gly Phe Leu Asn Lys
                       275                 280                 285
        Glu Val Glu Glu Gly Lys Leu Pro Lys Asn Leu Pro Ile Gln Ser
                       290                 295                 300
        Gly Val Gly Ser Val Ala Asn Ala Val Leu Ala Gly Leu Cys Glu Ser
        305                 310                 315                 320
        Asn Phe Lys Asn Leu Ser Cys Tyr Thr Glu Val Ile Gln Asp Ser Met
                       325                 330                 335
        Leu Lys Leu Ile Lys Cys Gly Lys Ala Asp Val Val Ser Gly Thr Ser
                       340                 345                 350
        Ile Ser Pro Ser Pro Glu Met Leu Pro Glu Phe Ile Lys Asp Ile Asn
                       355                 360                 365
        Phe Phe Arg Glu Lys Ile Val Leu Arg Pro Gln Glu Ile Ser Asn Asn
                       370                 375                 380
        Pro Glu Ile Ala Arg Arg Ile Gly Val Ile Ser Ile Asn Thr Ala Leu
        385                 390                 395                 400
        Glu Val Asp Ile Tyr Gly Asn Val Asn Ser Thr His Val Met Gly Ser
                       405                 410                 415
        Lys Met Met Asn Gly Ile Gly Gly Ser Gly Asp Phe Ala Arg Asn Ala
                       420                 425                 430
        Tyr Leu Thr Ile Phe Thr Thr Glu Ser Ile Ala Lys Lys Gly Asp Ile
                       435                 440                 445
        Ser Ser Ile Val Pro Met Val Ser His Val Asp His Thr Glu His Asp
                       450                 455                 460
        Val Met Val Ile Val Thr Glu Gln Gly Val Ala Asp Leu Arg Gly Leu
        465                 470                 475                 480
        Ser Pro Arg Glu Lys Ala Val Ala Ile Ile Glu Asn Cys Val His Pro
                       485                 490                 495
```

```
Asp Tyr Lys Asp Met Leu Met Glu Tyr Phe Glu Ala Cys Lys Ser
            500                 505                 510

Ser Gly Gly Asn Thr Pro His Asn Leu Glu Lys Ala Leu Ser Trp His
        515                 520                 525

Thr Lys Phe Ile Lys Thr Gly Ser Met Lys
        530                 535

<210> SEQ ID NO 2
<211> LENGTH: 1617
<212> TYPE: DNA
<213> ORGANISM: Artificial Sequence
<220> FEATURE:
<223> OTHER INFORMATION: Synthetic (polynucleotides coding Cat1 enzyme)

<400> SEQUENCE: 2
atgagtaaag ggataaagaa ttcacaattg aaaaaaaaga atgtaaaggc tagtaatgtg     60
gcagaaaaga ttgaagagaa agttgaaaaa acagataagg ttgttgaaaa ggcagctgag    120
gttacagaaa aacgaattag aaacttgaag cttcaggaaa aagttgtaac agcagatgtg    180
gcagctgata tgatagaaaa cggtatgatt gttgcaatta gcggatttac tccttccggg    240
tatcctaaag aagtacctaa agcattgact aaaaaagtta atgccttaga ggaagaattc    300
aaggtaacac tttatacagg ttcatctaca ggagccgata tagacggaga atgggcaaaa    360
gcaggaataa tagaaagaag aattccatat cagacaaatt ctgatatgag gaaaaaaata    420
aatgatggtt ctattaagta tgctgatatg catttaagcc atatggctca atatattaat    480
tattctgtaa ttcctaaagt agatatagct ataatagagg cagtagctat tacagaagaa    540
ggggatatta ttccttcaac aggaattgga aatacagcta cttttgtgga aaatgcagat    600 aagtaatag tggaaattaa tgaggctcaa ccgcttgaat ggaaggtat ggcagatata    660 tatacattaa aaaaccctcc aagaagagag cccataccta tagttaatgc aggcaatagg    720 ataggggacca catatgtgac ctgtggttct gaaaaaatat gcgctatagt gatgacaaat    780
acccaggata aacaagacc tcttacagaa gtgtctcctg tatctcaggc tatatccgat    840
aatcttatag atttttaaa taagaggtt gaagagggaa aattacctaa gaacctgctt    900
cctatacagt caggagttgg aagtgtagca atgcagtttt tggccggact ttgtgaatca    960 aatttttaaaa atttgagttg ttatacagaa gttatacagg attctatgct gaagcttata   1020
aaatgtggta agcagatgt ggtgtcaggc acttccataa gtccttcacc ggagatgttg   1080
cctgagttca taaaggacat aaatttcttt agagaaaaga tagtattaag accacaggaa   1140
ataagtaata atccagagat agcaagaaga ataggagtta tatccataaa cactgctttg   1200
gaagtagata tatatggtaa tgtaaactcc actcatgtta tgggaagcaa aatgatgaat   1260
ggtataggcg gttctggaga cttttgccaga aatgcatatt tgactatatt cactacagag   1320
tctatcgcca aaaaggaga tatatcatct atagttccta tggtatccca tgtggatcat   1380
acagaacatg atgtaatggt aattgttaca gaacagggag tagcagattt aagaggtctt   1440
tctcctaggg aaaaggccgt ggctataata gaaaattgtg ttcatcctga ttacaaggat   1500
atgcttatgg aatattttga agaggcttgt aagtcatcag gtgaaatac accacataat   1560 cttgaaaaag ctctttcctg gcatacaaaa tttataaaaa ctggtagtat gaaataa     1617

<210> SEQ ID NO 3
<211> LENGTH: 451
<212> TYPE: PRT
<213> ORGANISM: Artificial Sequence
```

<220> FEATURE:
<223> OTHER INFORMATION: Synthetic (SUCD enzyme)

<400> SEQUENCE: 3

```
Met Glu Ile Lys Glu Met Val Ser Leu Ala Arg Lys Ala Gln Lys Glu
1               5                   10                  15

Tyr Gln Ala Thr His Asn Gln Glu Ala Val Asp Asn Ile Cys Arg Ala
            20                  25                  30

Ala Ala Lys Val Ile Tyr Glu Asn Ala Ala Ile Leu Ala Arg Glu Ala
        35                  40                  45

Val Asp Glu Thr Gly Met Gly Val Tyr Glu His Lys Val Ala Lys Asn
    50                  55                  60

Gln Gly Lys Ser Lys Gly Val Trp Tyr Asn Leu His Asn Lys Lys Ser
65                  70                  75                  80

Ile Gly Ile Leu Asn Ile Asp Glu Arg Thr Gly Met Ile Glu Ile Ala
                85                  90                  95

Lys Pro Ile Gly Val Val Gly Ala Val Thr Pro Thr Thr Asn Pro Ile
            100                 105                 110

Val Thr Pro Met Ser Asn Ile Ile Phe Ala Leu Lys Thr Cys Asn Ala
        115                 120                 125

Ile Ile Ile Ala Pro His Pro Arg Ser Lys Lys Cys Ser Ala His Ala
130                 135                 140

Val Arg Leu Ile Lys Glu Ala Ile Ala Pro Phe Asn Val Pro Glu Gly
145                 150                 155                 160

Met Val Gln Ile Ile Glu Glu Pro Ser Ile Glu Lys Thr Gln Glu Leu
                165                 170                 175

Met Gly Ala Val Asp Val Val Ala Thr Gly Gly Met Gly Met Val
            180                 185                 190

Lys Ser Ala Tyr Ser Ser Gly Lys Pro Ser Phe Gly Val Gly Ala Gly
        195                 200                 205

Asn Val Gln Val Ile Val Asp Ser Asn Ile Asp Phe Glu Ala Ala Ala
    210                 215                 220

Glu Lys Ile Ile Thr Gly Arg Ala Phe Asp Asn Gly Ile Ile Cys Ser
225                 230                 235                 240

Gly Glu Gln Ser Ile Ile Tyr Asn Glu Ala Asp Lys Glu Ala Val Phe
                245                 250                 255

Thr Ala Phe Arg Asn His Gly Ala Tyr Phe Cys Asp Glu Ala Glu Gly
            260                 265                 270

Asp Arg Ala Arg Ala Ala Ile Phe Glu Asn Gly Ala Ile Ala Lys Asp
        275                 280                 285

Val Val Gly Gln Ser Val Ala Phe Ile Ala Lys Lys Ala Asn Ile Asn
    290                 295                 300

Ile Pro Glu Gly Thr Arg Ile Leu Val Val Glu Ala Arg Gly Val Gly
305                 310                 315                 320

Ala Glu Asp Val Ile Cys Lys Glu Lys Met Cys Pro Val Met Cys Ala
                325                 330                 335

Leu Ser Tyr Lys His Phe Glu Glu Gly Val Glu Ile Ala Arg Thr Asn
            340                 345                 350

Leu Ala Asn Glu Gly Asn Gly His Thr Cys Ala Ile His Ser Asn Asn
        355                 360                 365

Gln Ala His Ile Ile Leu Ala Gly Ser Glu Leu Thr Val Ser Arg Ile
    370                 375                 380

Val Val Asn Ala Pro Ser Ala Thr Ala Gly Gly His Ile Gln Asn
385                 390                 395                 400
```

Gly Leu Ala Val Thr Asn Thr Leu Gly Cys Gly Ser Trp Gly Asn Asn
                405                 410                 415

Ser Ile Ser Glu Asn Phe Thr Tyr Lys His Leu Leu Asn Ile Ser Arg
            420                 425                 430

Ile Ala Pro Leu Asn Ser Ser Ile His Ile Pro Asp Asp Lys Glu Ile
        435                 440                 445

Trp Glu Leu
    450

<210> SEQ ID NO 4
<211> LENGTH: 1356
<212> TYPE: DNA
<213> ORGANISM: Artificial Sequence
<220> FEATURE:
<223> OTHER INFORMATION: Synthetic (polynucleotides coding SUCD enzyme)

<400> SEQUENCE: 4

```
atggaaatca agaaatggt gagccttgca cgcaaggctc agaaggagta tcaagctacc      60
cataaccaag aagcagttga caacatttgc cgagctgcag caaaagttat ttatgaaaat    120
gcagctattc tggctcgcga agcagtagac gaaaccggca tgggcgttta cgaacacaaa    180
gtggccaaga tcaaggcaa atccaaaggt gtttggtaca acctccacaa taaaaaatcg    240
attggtatcc tcaatataga cgagcgtacc ggtatgatcg agattgcaaa gcctatcgga    300
gttgtaggag ccgtaacgcc gacgaccaac ccgatcgtta ctccgatgag caatatcatc    360
tttgctctta agacctgcaa tgccatcatt attgccccc accccagatc aaaaaaatgc    420
tctgcacacg cagttcgtct gatcaaagaa gctatcgctc cgttcaacgt accggaaggt    480
atggttcaga tcatcgaaga acccagcatc gagaagacgc aggaactcat gggcgccgta    540
gacgtagtag ttgctacggg tggtatgggc atggtgaagt ctgcatattc ttcaggaaag    600
ccttctttcg gtgttggagc cggtaacgtt caggtgatcg tggatagcaa catcgatttc    660
gaagctgctg cagaaaaaat catcaccggt cgtgctttcg acaacggtat catctgctca    720
ggcgaacaga gcatcatcta caacgaggct gacaaggaag cagttttcac agcattccgc    780
aaccacggtg catatttctg tgacgaagcc gaaggagatc gggctcgtgc agctatcttc    840
gaaaatggag ccatcgcgaa agatgtagta ggtcagagcg ttgccttcat gccaagaaa    900
gcaaacatca atatccccga gggtacccgt attctcgttg ttgaagctcg cggcgtagga    960
gcagaagacg ttatctgtaa ggaaaagatg tgtcccgtaa tgtgcgccct cagctacaag   1020
cacttcgaag aaggtgtaga atcgcacgt acgaacctcg ccaacgaagg taacggccac   1080
acctgtgcta tccactccaa caatcaggca cacatcatcc tcgcaggatc agagctgacg   1140
gtatctcgta tcgtagtgaa tgctccgagt gccactacag caggcggtca catccaaaac   1200
ggtcttgccg taaccaatac gctcggatgc ggatcatggg gtaataactc tatctccgag   1260
aacttcactt acaagcacct cctcaacatt tcacgcatcg caccgttgaa ttcaagcatt   1320
cacatccccg atgacaaaga aatctgggaa ctctaa                              1356
```

<210> SEQ ID NO 5
<211> LENGTH: 371
<212> TYPE: PRT
<213> ORGANISM: Artificial Sequence
<220> FEATURE:
<223> OTHER INFORMATION: Synthetic (4HBD enzyme)

<400> SEQUENCE: 5

```
Met Gln Leu Phe Lys Leu Lys Ser Val Thr His His Phe Asp Thr Phe
1               5                   10                  15

Ala Glu Phe Ala Lys Glu Phe Cys Leu Gly Glu Arg Asp Leu Val Ile
                20                  25                  30

Thr Asn Glu Phe Ile Tyr Glu Pro Tyr Met Lys Ala Cys Gln Leu Pro
            35                  40                  45

Cys His Phe Val Met Gln Glu Lys Tyr Gly Gln Gly Glu Pro Ser Asp
        50                  55                  60

Glu Met Met Asn Asn Ile Leu Ala Asp Ile Arg Asn Ile Gln Phe Asp
65                  70                  75                  80

Arg Val Ile Gly Ile Gly Gly Thr Val Ile Asp Ile Ser Lys Leu
                85                  90                  95

Phe Val Leu Lys Gly Leu Asn Asp Val Leu Asp Ala Phe Asp Arg Lys
                100                 105                 110

Ile Pro Leu Ile Lys Glu Lys Glu Leu Ile Ile Val Pro Thr Thr Cys
                115                 120                 125

Gly Thr Gly Ser Glu Val Thr Asn Ile Ser Ile Ala Glu Ile Lys Ser
        130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
                180                 185                 190

Ser Pro Lys Ala Ser Pro Tyr Ser Arg Leu Phe Ser Glu Ala Ala Trp
        195                 200                 205

Asp Ile Ile Leu Glu Val Phe Lys Lys Ile Ala Glu His Gly Pro Glu
        210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                245                 250                 255

Tyr Pro Leu Gly Gly Asn Tyr His Val Pro His Gly Glu Ala Asn Tyr
                260                 265                 270

Gln Phe Phe Thr Glu Val Phe Lys Val Tyr Gln Lys Lys Asn Pro Phe
        275                 280                 285

Gly Tyr Ile Val Glu Leu Asn Trp Lys Leu Ser Lys Ile Leu Asn Cys
        290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Glu Val
                325                 330                 335

Arg Gly Phe Ala Glu Ser Val Leu Lys Thr Gln Gln Arg Leu Leu Ala
                340                 345                 350

Asn Asn Tyr Val Glu Leu Thr Val Asp Glu Ile Glu Gly Ile Tyr Arg
        355                 360                 365

Arg Leu Tyr
    370

<210> SEQ ID NO 6
<211> LENGTH: 1116
<212> TYPE: DNA
<213> ORGANISM: Artificial Sequence
<220> FEATURE:
<223> OTHER INFORMATION: Synthetic (polynucleotides coding 4HBD enzyme)
```

<400> SEQUENCE: 6

```
atgcaacttt tcaaactcaa gagtgtaaca catcactttg acactttgc agaatttgcc      60
aaggaattct gtcttggaga acgcgacttg gtaattacca acgagttcat ctatgaaccg     120
tatatgaagg catgccagct ccctgccat tttgttatgc aggagaaata tgggcaaggc     180
gagccttctg acgaaatgat gaataacatc ttggcagaca tccgtaatat ccagttcgac     240
cgcgtaatcg gtatcggagg aggtacggtt attgacatct ctaaactttt cgttctgaaa     300
ggattaaatg atgtactcga tgcattcgac cgcaaaatac ctcttatcaa agagaaagaa     360
ctgatcattg tgcccacaac atgcggaacg ggtagcgagg tgacgaacat ttctatcgca     420
gaaatcaaaa gccgtcacac caaaatggga ttggctgacg atgccattgt tgcagaccat     480
gccatcatca tacctgaact tctgaagagc ttgcctttcc acttctacgc atgcagtgca     540
atcgatgctc ttatccatgc catcgagtca tacgtatctc ctaaagccag tccatattct     600
cgtctgttca gtgaggcggc ttgggacatt atcctggaag tattcaagaa aatcgccgaa     660
cacggccctg aataccgctt cgaaaagctg ggagaaatga tcatggccag caactatgcc     720
ggtatagcct tcggaaatgc aggagtagga gccgtccacg cactatccta cccgttggga     780
ggcaactatc acgtgccgca tggagaagca aactatcagt tcttcacaga ggtattcaaa     840
gtataccaaa agaagaatcc tttcggctat atagtcgaac tcaactggaa gctctccaag     900
atactgaact gccagcccga atacgtatat ccgaagctgg atgaacttct cggatgcctt     960
cttaccaaga aacctttgca cgaataccgg atgaaggacg aagaggtaag aggctttgcg    1020
gaatcagtgc ttaagacaca gcaaagattg ctcgccaaca actacgtaga gcttactgta    1080
gatgagatcg aaggtatcta cagaagactc tactaa                             1116
```

<210> SEQ ID NO 7
<211> LENGTH: 1214
<212> TYPE: PRT
<213> ORGANISM: Artificial Sequence
<220> FEATURE:
<223> OTHER INFORMATION: Synthetic (SUCA enzyme)

<400> SEQUENCE: 7

```
Met Tyr Arg Lys Phe Arg Asp Asp Pro Ser Ser Val Asp Pro Ser Trp
  1               5                  10                  15

His Glu Phe Leu Val Asp Tyr Ser Pro Glu Pro Thr Ser Gln Pro Ala
             20                  25                  30

Ala Glu Pro Thr Arg Val Thr Ser Pro Leu Val Ala Glu Arg Ala Ala
         35                  40                  45

Ala Ala Ala Pro Gln Ala Pro Pro Lys Pro Ala Asp Thr Ala Ala Ala
     50                  55                  60

Gly Asn Gly Val Val Ala Ala Leu Ala Ala Lys Thr Ala Val Pro Pro
 65                  70                  75                  80

Pro Ala Glu Gly Asp Glu Val Ala Val Leu Arg Gly Ala Ala Ala Ala
                 85                  90                  95

Val Val Lys Asn Met Ser Ala Ser Leu Glu Val Pro Thr Ala Thr Ser
            100                 105                 110

Val Arg Ala Val Pro Ala Lys Leu Leu Ile Asp Asn Arg Ile Val Ile
        115                 120                 125

Asn Asn Gln Leu Lys Arg Thr Arg Gly Gly Lys Ile Ser Phe Thr His
    130                 135                 140

Leu Leu Gly Tyr Ala Leu Val Gln Ala Val Lys Lys Phe Pro Asn Met
```

```
            145                 150                 155                 160
Asn Arg His Tyr Thr Glu Val Asp Gly Lys Pro Thr Ala Val Thr Pro
                165                 170                 175

Ala His Thr Asn Leu Gly Leu Ala Ile Asp Leu Gln Gly Lys Asp Gly
                180                 185                 190

Lys Arg Ser Leu Val Val Ala Gly Ile Lys Arg Cys Glu Thr Met Arg
                195                 200                 205

Phe Ala Gln Phe Val Thr Ala Tyr Glu Asp Ile Val Arg Arg Ala Arg
210                 215                 220

Asp Gly Lys Leu Thr Thr Glu Asp Phe Ala Gly Val Thr Ile Ser Leu
225                 230                 235                 240

Thr Asn Pro Gly Thr Ile Gly Thr Val His Ser Val Pro Arg Leu Met
                245                 250                 255

Pro Gly Gln Gly Ala Ile Ile Gly Val Gly Ala Met Glu Tyr Pro Ala
                260                 265                 270

Glu Phe Gln Gly Ala Ser Glu Glu Arg Ile Ala Glu Leu Gly Ile Gly
                275                 280                 285

Lys Leu Ile Thr Leu Thr Ser Thr Tyr Asp His Arg Ile Ile Gln Gly
                290                 295                 300

Ala Glu Ser Gly Asp Phe Leu Arg Thr Ile His Glu Leu Leu Leu Ser
305                 310                 315                 320

Asp Gly Phe Trp Asp Glu Val Phe Arg Glu Leu Ser Ile Pro Tyr Leu
                325                 330                 335

Pro Val Arg Trp Ser Thr Asp Asn Pro Asp Ser Ile Val Asp Lys Asn
                340                 345                 350

Ala Arg Val Met Asn Leu Ile Ala Ala Tyr Arg Asn Arg Gly His Leu
                355                 360                 365

Met Ala Asp Thr Asp Pro Leu Arg Leu Asp Lys Ala Arg Phe Arg Ser
                370                 375                 380

His Pro Asp Leu Glu Val Leu Thr His Gly Leu Thr Leu Trp Asp Leu
385                 390                 395                 400

Asp Arg Val Phe Lys Val Asp Gly Phe Ala Gly Ala Gln Tyr Lys Lys
                405                 410                 415

Leu Arg Asp Val Leu Gly Leu Leu Arg Asp Ala Tyr Cys Arg His Ile
                420                 425                 430

Gly Val Glu Tyr Ala His Ile Leu Asp Pro Glu Gln Lys Glu Trp Leu
                435                 440                 445

Glu Gln Arg Val Glu Thr Lys His Val Lys Pro Thr Val Ala Gln Gln
450                 455                 460

Lys Tyr Ile Leu Ser Lys Leu Asn Ala Ala Glu Ala Phe Glu Thr Phe
465                 470                 475                 480

Leu Gln Thr Lys Tyr Val Gly Gln Lys Arg Phe Ser Leu Glu Gly Ala
                485                 490                 495

Glu Ser Val Ile Pro Met Met Asp Ala Ala Ile Asp Gln Cys Ala Glu
                500                 505                 510

His Gly Leu Asp Glu Val Val Ile Gly Met Pro His Arg Gly Arg Leu
                515                 520                 525

Asn Val Leu Ala Asn Ile Val Gly Lys Pro Tyr Ser Gln Ile Phe Thr
                530                 535                 540

Glu Phe Glu Gly Asn Leu Asn Pro Ser Gln Ala His Gly Ser Gly Asp
545                 550                 555                 560

Val Lys Tyr His Leu Gly Ala Thr Gly Leu Tyr Leu Gln Met Phe Gly
                565                 570                 575
```

```
Asp Asn Asp Ile Gln Val Ser Leu Thr Ala Asn Pro Ser His Leu Glu
            580                 585                 590

Ala Val Asp Pro Val Leu Glu Gly Leu Val Arg Ala Lys Gln Asp Leu
        595                 600                 605

Leu Asp His Gly Ser Ile Asp Ser Asp Gly Gln Arg Ala Phe Ser Val
610                 615                 620

Val Pro Leu Met Leu His Gly Asp Ala Ala Phe Ala Gly Gln Gly Val
625                 630                 635                 640

Val Ala Glu Thr Leu Asn Leu Ala Asn Leu Pro Gly Tyr Arg Val Gly
            645                 650                 655

Gly Thr Ile His Ile Ile Val Asn Asn Gln Ile Gly Phe Thr Thr Ala
                660                 665                 670

Pro Glu Tyr Ser Arg Ser Ser Glu Tyr Cys Thr Asp Val Ala Lys Met
            675                 680                 685

Ile Gly Ala Pro Ile Phe His Val Asn Gly Asp Asp Pro Glu Ala Cys
        690                 695                 700

Val Trp Val Ala Arg Leu Ala Val Asp Phe Arg Gln Arg Phe Lys Lys
705                 710                 715                 720

Asp Val Val Ile Asp Met Leu Cys Tyr Arg Arg Gly His Asn Glu
            725                 730                 735

Gly Asp Asp Pro Ser Met Thr Asn Pro Tyr Met Tyr Asp Val Val Asp
                740                 745                 750

Thr Lys Arg Gly Ala Arg Lys Ser Tyr Thr Glu Ala Leu Ile Gly Arg
            755                 760                 765

Gly Asp Ile Ser Met Lys Glu Ala Asp Ala Leu Arg Asp Tyr Gln
770                 775                 780

Gly Gln Leu Glu Arg Val Phe Asn Glu Val Arg Glu Leu Glu Lys His
785                 790                 795                 800

Gly Val Gln Pro Ser Glu Ser Val Glu Ser Asp Gln Met Ile Pro Ala
            805                 810                 815

Gly Leu Ala Thr Ala Val Asp Lys Ser Leu Leu Ala Arg Ile Gly Asp
            820                 825                 830

Ala Phe Leu Ala Leu Pro Asn Gly Phe Thr Ala His Pro Arg Val Gln
        835                 840                 845

Pro Val Leu Glu Lys Arg Arg Glu Met Ala Tyr Glu Gly Lys Ile Asp
850                 855                 860

Trp Ala Phe Gly Glu Leu Leu Ala Leu Gly Ser Leu Val Ala Glu Gly
865                 870                 875                 880

Lys Leu Val Arg Leu Ser Gly Gln Asp Ser Arg Arg Gly Thr Phe Ser
            885                 890                 895

Gln Arg His Ser Val Leu Ile Asp Arg His Thr Gly Glu Glu Phe Thr
            900                 905                 910

Pro Leu Gln Leu Leu Ala Thr Asn Ser Asp Gly Ser Pro Thr Gly Gly
        915                 920                 925

Lys Phe Leu Val Tyr Asp Ser Pro Leu Ser Glu Tyr Ala Ala Val Gly
            930                 935                 940

Phe Glu Tyr Gly Tyr Thr Val Gly Asn Pro Asp Ala Val Val Leu Trp
945                 950                 955                 960

Glu Ala Gln Phe Gly Asp Phe Val Asn Gly Ala Gln Ser Ile Ile Asp
            965                 970                 975

Glu Phe Ile Ser Ser Gly Glu Ala Lys Trp Gly Gln Leu Ser Asn Val
            980                 985                 990
```

Val Leu Leu Leu Pro His Gly His Glu Gly Gln Gly Pro Asp His Thr
        995                 1000                1005

Ser Ala Arg Ile Glu Arg Phe Leu Gln Leu Trp Ala Glu Gly Ser
    1010                1015                1020

Met Thr Ile Ala Met Pro Ser Thr Pro Ser Asn Tyr Phe His Leu
    1025                1030                1035

Leu Arg Arg His Ala Leu Asp Gly Ile Gln Arg Pro Leu Ile Val
    1040                1045                1050

Phe Thr Pro Lys Ser Met Leu Arg His Lys Ala Ala Val Ser Glu
    1055                1060                1065

Ile Lys Asp Phe Thr Glu Ile Lys Phe Arg Ser Val Leu Glu Glu
    1070                1075                1080

Pro Thr Tyr Glu Asp Gly Ile Gly Asp Arg Asn Lys Val Ser Arg
    1085                1090                1095

Ile Leu Leu Thr Ser Gly Lys Leu Tyr Tyr Glu Leu Ala Ala Arg
    1100                1105                1110

Lys Ala Lys Asp Asn Arg Asn Asp Leu Ala Ile Val Arg Leu Glu
    1115                1120                1125

Gln Leu Ala Pro Leu Pro Arg Arg Arg Leu Arg Glu Thr Leu Asp
    1130                1135                1140

Arg Tyr Glu Asn Val Lys Glu Phe Phe Trp Val Gln Glu Glu Pro
    1145                1150                1155

Ala Asn Gln Gly Ala Trp Pro Arg Phe Gly Leu Glu Leu Pro Glu
    1160                1165                1170

Leu Leu Pro Asp Lys Leu Ala Gly Ile Lys Arg Ile Ser Arg Arg
    1175                1180                1185

Ala Met Ser Ala Pro Ser Ser Gly Ser Ser Lys Val His Ala Val
    1190                1195                1200

Glu Gln Gln Glu Ile Leu Asp Glu Ala Phe Gly
    1205                1210

<210> SEQ ID NO 8
<211> LENGTH: 3645
<212> TYPE: DNA
<213> ORGANISM: Artificial Sequence
<220> FEATURE:
<223> OTHER INFORMATION: Synthetic (polynucleotides coding SUCA enzyme)

<400> SEQUENCE: 8
atgtaccgaa aattccgcga cgatccatct tctgtcgatc cttcatggca tgaattcctt    60
gtggattatt cacccgagcc aacttctcaa cctgctgccg aacctacgcg tgtgacttcg   120
ccattggttg ctgaacgcgc agcagcagcg gctccccaag ctccaccaaa gcccgcagat   180
actgccgctg caggtaacgg tgtagttgct gcattggcag caaagaccgc tgtgccacct   240
ccagctgagg gtgatgaggt agctgtgctt cgtggagcag cagctgcggt tgtgaagaac   300
atgtctgctt ccctcgaggt gccgactgca acgtctgttc gcgccgtacc cgccaaactg   360
ctgatcgaca atcgcattgt gatcaacaat caactcaagc gtacgcgagg cggcaagatc   420
tcctttactc acttgttggg ctacgccctc gttcaggccg tcaagaaatt cccgaacatg   480
aaccgccatt acaccgaagt agacggaaag ccgacagccg tcacgccagc acacacgaac   540
ctgggcctcg ctatcgatct gcagggtaaa gacggtaaac gttcgcttgt cgtcgcaggc   600
atcaagcgct gcgagacaat gcgtttcgcc cagtttgtta ctgcgtatga ggatatcgtt   660
cgccgtgcgc gtgacggtaa gctcacaacc gaggacttcg caggggtcac gatcagcctt   720

```
acgaaccctg ggaccattgg taccgttcat tcggtcccac gactgatgcc aggccaaggg    780
gccatcatcg gcgttggggc tatggaatac cctgcggagt tccagggagc tctctgaggag   840
cgcattgcag aacttggcat cggtaagctg atcaccctga ctagcaccta tgaccaccgc    900
attattcagg gggcagaaag cggtgatttc ctccgaacca tccatgagct cctgctctcc    960
gatggctttt gggatgaggt tttccgagaa cttttccattc cgtacctccc ggtccgctgg  1020
agcaccgaca cccccgattc catcgtcgat aaaaacgccc gagtcatgaa cctcatcgct   1080
gcgtaccgta accgtggcca cttgatggcc gatacggacc ccttgcgctt ggacaaggct   1140
cgcttccgct cgcacccgga tcttgaagtg ctgacccatg gcctgaccct tgggatctg    1200
gatcgtgtct tcaaggtcga cggttttgcc ggagcacagt acaagaaact tcgagacgtc   1260
ctcggcctcc tgcgtgatgc gtactgccgt cacatcggcg tggaatatgc ccacatcctt   1320
gaccctgaac agaaggagtg gttggagcaa cgcgtcgaga ctaaacacgt gaagccaacc   1380
gtggcgcagc aaaagtacat cctgtcgaag ttgaacgcag ccgaggcctt cgagactttc   1440
ttgcagacca aatatgttgg ccaaaagcgg ttctctctgg agggcgcgga gtccgtgatt   1500
cctatgatgg atgccgctat cgaccaatgc gcagagcacg gactggacga ggtcgttatc   1560
ggcatgcctc atcgcggccg ccttaatgtc ttggcaaata ttgtgggaaa gccgtattcc   1620
cagatcttca ccgagttcga aggtaatctg aacccatccc aggctcatgg ctcgggcgat   1680
gttaagtacc acctgggcgc caccggtttg tatctccaga tgtttggtga taacgatatt   1740
caagttagcc ttaccgctaa tccgtcccac ctggaggctg tggatccggt gctcgaaggt   1800
ctcgtgcggg cgaagcagga tctgctcgac cacggttcca tcgactctga tggtcagcgc   1860
gccttctcag tcgttccctt gatgttgcac ggagatgcgg cattcgctgg tcaaggagta   1920
gtggcggaaa ccctcaacct cgcgaacctg ccgggctacc gcgttggggg cactatccac   1980
attattgtca caaccagat tggctttacc acagctcccg agtactctcg ctcttcagaa    2040
tactgtactg acgtcgcgaa gatgatcggt gcgccgatct tccatgtcaa cggcgacgac   2100
ccagaggcat gtgtctgggt cgcacgtctc gccgtcgatt tccgccagcg gttcaagaaa   2160
gacgtcgtga ttgacatgct tgctaccgc cgccgcgggc acaatgaggg agatgacca   2220
tcaatgacca acccatacat gtacgacgtt gtagatacca agcgcggcgc gcgtaaatcc   2280
tacaccgagg ccccttatcgg tcggggcgat atctccatga agaggctga agatgcactt   2340
cgggattacc agggccagtt ggaacgcgtt tttaacgaag ttcgcgagct ggaaaaacat   2400
ggagttcagc cgtccgagtc ggttgaaagc gatcaaatga ttccagctgg cttggcgacc   2460
gccgttgata aatccttgct ggctcggatc ggagatgcat tcctggcgct gcctaatggt   2520
ttcaccgcgc acccacgcgt gcagccggta cttgagaagc gccgtgaaat ggcctacgaa   2580
ggcaagattg actgggcatt cggtgaactg ctggctctgg gttcgctggt ggcggagggt   2640
aagcttgttc gactgtccgg ccaggattcc cgtcggggca ccttctccca gcgccactct   2700
gtcctgatcg atcggcacac aggcgaagaa ttcaccccctc tgcagcttct cgctaccaac   2760
tcagacggat cgccaaccgg aggaaagttc ctcgtatatg atagccccct ctcagaatac   2820
gcagcagtgg gctttgagta cggctacact gtaggcaatc ccgacgcggt ggtcctttgg   2880
gaggctcagt tcggtgactt tgttaacggc gcacagtcca tcatcgacga gtttatttca   2940
agcggcgaag caaagtgggg tcaattgtcc aatgtcgtgc tgctcctgcc acatggacac   3000
gaaggtcagg ggccggacca cacctccgct cgtattgaac gcttcctcca actgtgggca   3060
gaaggaagca tgaccattgc tatgccatcc accccatcaa attattttca cctgctgcgg   3120
```

-continued

```
cgccatgcct tggacgggat ccagcggcct cttattgtct tcacaccaaa gtccatgctc    3180
cgccacaaag ctgcagtgtc tgaaatcaaa gacttcaccg aaatcaagtt ccgctccgtt    3240
ctggaagaac caacctacga ggacggaatc ggcgaccgca acaaggtgtc ccgtatcctg    3300
ttgacttccg gaaaactcta ttacgaactt gcagcgcgta aggcaaagga taaccggaat    3360
gacctcgcca tcgtgcgcct ggagcagctc gcacctttgc ctcgtcgacg cctccgcgaa    3420
accctggacc gttacgaaaa cgttaaggaa ttttttctggg tgcaggaaga gcctgctaac    3480
cagggtgcct ggccacgttt tgggctcgag cttcccgaac tcctgccgga taaactcgct    3540
ggtattaaac ggatctcccg tcgtgctatg tctgcccctt ccagcggcag ctctaaggtg    3600
cacgcggtgg agcaacagga gatcctggat gaagcatttg gttaa                   3645
```

<210> SEQ ID NO 9
<211> LENGTH: 1140
<212> TYPE: PRT
<213> ORGANISM: Artificial Sequence
<220> FEATURE:
<223> OTHER INFORMATION: Synthetic (pyruvate carboxylase)

<400> SEQUENCE: 9

```
Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270
```

-continued

```
Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685
```

-continued

Leu Tyr Thr Leu Asp Tyr Tyr Leu Lys Met Ala Glu Glu Ile Val Lys
        690             695             700

Ser Gly Ala His Ile Leu Ala Ile Lys Asp Met Ala Gly Leu Leu Arg
705             710             715             720

Pro Ala Ala Val Thr Lys Leu Val Thr Ala Leu Arg Arg Glu Phe Asp
            725             730             735

Leu Pro Val His Val His Thr His Asp Thr Ala Gly Gly Gln Leu Ala
            740             745             750

Thr Tyr Phe Ala Ala Gln Ala Gly Ala Asp Ala Val Asp Gly Ala
        755             760             765

Ser Ala Pro Leu Ser Gly Thr Thr Ser Gln Pro Ser Leu Ser Ala Ile
770             775             780

Val Ala Ala Phe Ala His Thr Arg Arg Asp Thr Gly Leu Ser Leu Glu
785             790             795             800

Ala Val Ser Asp Leu Glu Pro Tyr Trp Glu Ala Val Arg Gly Leu Tyr
                805             810             815

Leu Pro Phe Glu Ser Gly Thr Pro Gly Pro Thr Gly Arg Val Tyr Arg
            820             825             830

His Glu Ile Pro Gly Gly Gln Leu Ser Asn Leu Arg Ala Gln Ala Thr
            835             840             845

Ala Leu Gly Leu Ala Asp Arg Phe Glu Leu Ile Glu Asp Asn Tyr Ala
850             855             860

Ala Val Asn Glu Met Leu Gly Arg Pro Thr Lys Val Thr Pro Ser Ser
865             870             875             880

Lys Val Val Gly Asp Leu Ala Leu His Leu Val Gly Ala Gly Val Asp
            885             890             895

Pro Ala Asp Phe Ala Ala Asp Pro Gln Lys Tyr Asp Ile Pro Asp Ser
            900             905             910

Val Ile Ala Phe Leu Arg Gly Glu Leu Gly Asn Pro Pro Gly Gly Trp
        915             920             925

Pro Glu Pro Leu Arg Thr Arg Ala Leu Glu Gly Arg Ser Glu Gly Lys
    930             935             940

Ala Pro Leu Thr Glu Val Pro Glu Glu Gln Ala His Leu Asp Ala
945             950             955             960

Asp Asp Ser Lys Glu Arg Arg Asn Ser Leu Asn Arg Leu Leu Phe Pro
            965             970             975

Lys Pro Thr Glu Glu Phe Leu Glu His Arg Arg Arg Phe Gly Asn Thr
        980             985             990

Ser Ala Leu Asp Asp Arg Glu Phe Phe Tyr Gly Leu Val Glu Gly Arg
        995             1000            1005

Glu Thr Leu Ile Arg Leu Pro Asp Val Arg Thr Pro Leu Leu Val
    1010            1015            1020

Arg Leu Asp Ala Ile Ser Glu Pro Asp Lys Gly Met Arg Asn
        1025            1030            1035

Val Val Ala Asn Val Asn Gly Gln Ile Arg Pro Met Arg Val Arg
        1040            1045            1050

Asp Arg Ser Val Glu Ser Val Thr Ala Thr Ala Glu Lys Ala Asp
    1055            1060            1065

Ser Ser Asn Lys Gly His Val Ala Ala Pro Phe Ala Gly Val Val
        1070            1075            1080

Thr Val Thr Val Ala Glu Gly Asp Glu Val Lys Ala Gly Asp Ala
    1085            1090            1095

Val Ala Ile Ile Glu Ala Met Lys Met Glu Ala Thr Ile Thr Ala

```
            1100                1105                1110

Ser Val  Asp Gly Lys Ile Asp  Arg Val Val Val Pro  Ala Ala Thr
            1115                1120                1125

Lys Val  Glu Gly Gly Asp Leu  Ile Val Val Val Ser
            1130                1135                1140

<210> SEQ ID NO 10
<211> LENGTH: 1140
<212> TYPE: PRT
<213> ORGANISM: Artificial Sequence
<220> FEATURE:
<223> OTHER INFORMATION: Synthetic (pyruvate carboxylase)

<400> SEQUENCE: 10

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
```

```
            325                 330                 335
Thr Gln Asp Lys Ile Lys Thr His Gly Ala Ala Leu Gln Cys Arg Ile
                340                 345                 350
Thr Thr Glu Asp Pro Asn Asn Gly Phe Arg Pro Asp Thr Gly Thr Ile
            355                 360                 365
Thr Ala Tyr Arg Ser Pro Gly Ala Gly Val Arg Leu Asp Gly Ala
        370                 375                 380
Ala Gln Leu Gly Gly Glu Ile Thr Ala His Phe Asp Ser Met Leu Val
385                 390                 395                 400
Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
            420                 425                 430
Gly Phe Leu Arg Ala Leu Leu Arg Glu Glu Asp Phe Thr Ser Lys Arg
        435                 440                 445
Ile Ala Thr Gly Phe Ile Ala Asp His Ser His Leu Leu Gln Ala Pro
        450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
            500                 505                 510
Arg Asp Arg Leu Lys Gln Leu Gly Pro Ala Ala Phe Ala Arg Asp Leu
        515                 520                 525
Arg Glu Gln Asp Ala Leu Ala Val Thr Asp Thr Thr Phe Arg Asp Ala
        530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
            580                 585                 590
Asp Pro Trp Asp Arg Leu Asp Glu Leu Arg Glu Ala Met Pro Asn Val
        595                 600                 605
Asn Ile Gln Met Leu Leu Arg Gly Arg Asn Thr Val Gly Tyr Thr Pro
        610                 615                 620
Tyr Pro Asp Ser Val Cys Arg Ala Phe Val Lys Glu Ala Ala Ser Ser
625                 630                 635                 640
Gly Val Asp Ile Phe Arg Ile Phe Asp Ala Leu Asn Asp Val Ser Gln
                645                 650                 655
Met Arg Pro Ala Ile Asp Ala Val Leu Glu Thr Asn Thr Ala Val Ala
            660                 665                 670
Glu Val Ala Met Ala Tyr Ser Gly Asp Leu Ser Asp Pro Asn Glu Lys
        675                 680                 685
Leu Tyr Thr Leu Asp Tyr Tyr Leu Lys Met Ala Glu Glu Ile Val Lys
        690                 695                 700
Ser Gly Ala His Ile Leu Ala Ile Lys Asp Met Ala Gly Leu Leu Arg
705                 710                 715                 720
Pro Ala Ala Val Thr Lys Leu Val Thr Ala Leu Arg Arg Glu Phe Asp
                725                 730                 735
Leu Pro Val His Val His Thr His Asp Thr Ala Gly Gly Gln Leu Ala
            740                 745                 750
```

Thr Tyr Phe Ala Ala Ala Gln Ala Gly Ala Asp Ala Val Asp Gly Ala
    755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
    1130                1135                1140

<210> SEQ ID NO 11
<211> LENGTH: 3423

<212> TYPE: DNA
<213> ORGANISM: Artificial Sequence
<220> FEATURE:
<223> OTHER INFORMATION: Synthetic (nucleotide coding pyruvate carboxylase)

<400> SEQUENCE: 11

| | | | | | |
|---|---|---|---|---|---|
| gtgtcgactc | acacatcttc | aacgcttcca | gcattcaaaa | agatcttggt | agcaaaccgc | 60 |
| ggcgaaatcg | cggtccgtgc | tttccgtgca | gcactcgaaa | ccggtgcagc | cacggtagct | 120 |
| atttacccc | gtgaagatcg | gggatcattc | caccgctctt | ttgcttctga | agctgtccgc | 180 |
| attggtaccg | aaggctcacc | agtcaaggcg | tacctggaca | tcgatgaaat | tatcggtgca | 240 |
| gctaaaaaag | ttaaagcaga | tgccatttac | ccgggatacg | gcttcctgtc | tgaaaatgcc | 300 |
| cagcttgccc | gcgagtgtgc | ggaaaacggc | attactttta | ttggcccaac | cccagaggtt | 360 |
| cttgatctca | ccggtgataa | gtctcgcgcg | gtaaccgccg | cgaagaaggc | tggtctgcca | 420 |
| gttttggcgg | aatccacccc | gagcaaaaac | atcgatgaga | tcgttaaaag | cgctgaaggc | 480 |
| cagacttacc | ccatctttgt | gaaggcagtt | gccggtggtg | gcggacgcgg | tatgcgtttt | 540 |
| gttgcttcac | ctgatgagct | tgcaaatta | gcaacagaag | catctcgtga | agctgaagcg | 600 |
| gctttcggcg | atggcgcggt | atatgtcgaa | cgtgctgtga | ttaaccctca | gcatattgaa | 660 |
| gtgcagatcc | ttggcgatca | cactggagaa | gttgtacacc | tttatgaacg | tgactgctca | 720 |
| ctgcagcgtc | gtcaccaaaa | agttgtcgaa | attgcgccag | cacagcattt | ggatccagaa | 780 |
| ctgcgtgatc | gcatttgtgc | ggatgcagta | aagttctgcc | gctccattgg | ttaccagggc | 840 |
| gcgggaaccg | tggaattctt | ggtcgatgaa | agggcaacc | acgtcttcat | cgaaatgaac | 900 |
| ccacgtatcc | aggttgagca | caccgtgact | gaagaagtca | ccgaggtgga | cctggtgaag | 960 |
| gcgcagatgc | gcttggctgc | tggtgcaacc | ttgaaggaat | tgggtctgac | ccaagataag | 1020 |
| atcaagaccc | acggtgcagc | actgcagtgc | cgcatcacca | cggaagatcc | aaacaacggc | 1080 |
| ttccgcccag | ataccggaac | tatcaccgcg | taccgctcac | caggcggagc | tggcgttcgt | 1140 |
| cttgacggtg | cagctcagct | cggtggcgaa | atcaccgcac | actttgactc | catgctggtg | 1200 |
| aaaatgacct | gccgtggttc | cgactttgaa | actgctgttg | ctcgtgcaca | gcgcgcgttg | 1260 |
| gctgagttca | ccgtgtctgg | tgttgcaacc | aacattggtt | tcttgcgtgc | gttgctgcgg | 1320 |
| gaagaggact | tcacttccaa | gcgcatcgcc | accggattca | ttgccgatca | cccgcacctc | 1380 |
| cttcaggctc | cacctgctga | tgatgagcag | ggacgcatcc | tggattactt | ggcagatgtc | 1440 |
| accgtgaaca | gcctcatgg | tgtgcgtcca | aaggatgttg | cagctcctat | cgataagctg | 1500 |
| cctaacatca | aggatctgcc | actgccacgc | ggttcccgtg | accgcctgaa | gcagcttggc | 1560 |
| ccagccgcgt | ttgctcgtga | tctccgtgag | caggacgcac | tggcagttac | tgataccacc | 1620 |
| ttccgcgatg | cacaccagtc | tttgcttgcg | acccgagtcc | gctcattcgc | actgaagcct | 1680 |
| gcggcagagg | ccgtcgcaaa | gctgactcct | gagcttttgt | ccgtggaggc | ctggggcggc | 1740 |
| gcgacctacg | atgtggcgat | gcgtttcctc | tttgaggatc | cgtgggacag | gctcgacgag | 1800 |
| ctgcgcgagg | cgatgccgaa | tgtaaacatt | cagatgctgc | ttcgcggccg | caacaccgtg | 1860 |
| ggatacaccc | cgtacccaga | ctccgtctgc | cgcgcgtttg | ttaaggaagc | tgccagctcc | 1920 |
| ggcgtggaca | tcttccgcat | cttcgacgcg | cttaacgacg | tctcccagat | gcgtccagca | 1980 |
| atcgacgcag | tcctggagac | caacaccgcg | gtagccgagg | tggctatggc | ttattctggt | 2040 |
| gatctctctg | atccaaatga | aaagctctac | acctggatt | actacctaaa | gatggcgagg | 2100 |
| gagatcgtca | agtctggcgc | tcacatcttg | gccattaagg | atatggctgg | tctgcttcgc | 2160 |

```
ccagctgcgg taaccaagct ggtcaccgca ctgcgccgtg aattcgatct gccagtgcac    2220
gtgcacaccc acgacactgc gggtggccag ctggcaacct actttgctgc agctcaagct    2280
ggtgcagatg ctgttgacgg tgcttccgca ccactgtctg gcaccacctc ccagccatcc    2340
ctgtctgcca ttgttgctgc attcgcgcac acccgtcgcg ataccggttt gagcctcgag    2400
gctgtttctg acctcgagcc gtactgggaa gcagtgcgcg gactgtacct gccatttgag    2460
tctggaaccc caggcccaac cggtcgcgtc taccgccacg aaatcccagg cggacagttg    2520
tccaacctgc gtgcacaggc accgcactg ggccttgcgg atcgtttcga actcatcgaa    2580
gacaactacg cagccgttaa tgagatgctg ggacgcccaa ccaaggtcac ccatcctcc     2640 aaggttgttg gcgacctcgc actccacctc gttggtgcgg gtgtggatcc agcagacttt    2700
gctgccgatc cacaaaagta cgacatccca gactctgtca tcgcgttcct gcgcggcgag    2760
cttggtaacc ctccaggtgg ctggccagag ccactgcgca cccgcgcact ggaaggccgc    2820
tccgaaggca aggcacctct gacggaagtt cctgaggaag agcaggcgca cctcgacgct    2880
gatgattcca aggaacgtcg caatagcctc aaccgcctgc tgttcccgaa gccaaccgaa    2940
gagttcctcg agcaccgtcg ccgcttcggc aacacctctg cgctggatga tcgtgaattc    3000
ttctacggcc tggtcgaagg ccgcgagact ttgatccgcc tgccagatgt gcgcaccca     3060 ctgcttgttc gcctggatgc gatctctgag ccagacgata agggtatgcg caatgttgtg    3120
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ccgtgactgt tgctgaaggt gatgaggtca aggctggaga tgcagtcgca    3300
atcatcgagg ctatgaagat ggaagcaaca atcactgctt ctgttgacgg caaaatcgat    3360
cgcgttgtgg ttcctgctgc aacgaaggtg aaggtggcg acttgatcgt cgtcgtttcc    3420
taa                                                                  3423
```

<210> SEQ ID NO 12
<211> LENGTH: 1425
<212> TYPE: DNA
<213> ORGANISM: Artificial Sequence
<220> FEATURE:
<223> OTHER INFORMATION: Synthetic (nucleotides coding lpd(lipoamide dehydrogenase))

<400> SEQUENCE: 12

```
atgagtactg aaatcaaaac tcaggtcgtg gtacttgggg caggccccgc aggttactcc     60
gctgccttcc gttgcgctga tttaggtctg gaaaccgtaa tcgtagaacg ttacaacacc    120
cttggcggtt tttgcctgaa cgtcggctgt atcccttcta agcactgct gcacgtagca    180 aaagttatcg aagaagccaa agcgctggct gaacacggta tcgtcttcgg cgaaccgaaa    240
accgatatcg acaagattcg tacctggaaa gagaaagtga tcaatcagct gaccggtggt    300
ctggctggta tggcgaaagg ccgcaaagtc aaagtggtca acggtctggg taaattcacc    360
ggggctaaca ccctggaagt tgaaggtgag aacggcaaaa ccgtgatcaa cttcgacaac    420
gcgatcattg cagcgggttc tcgcccgatc caactgccgt ttattccgca tgaagatccg    480
cgtatctggg actccactga cgcgctggaa ctgaagaag taccagaacg cctgctggta    540
atgggtggcg gtatcatcgg tctggaaatg ggcaccgttt accacgcgct gggttcacag    600
attgacgtgt tgaaatgtt cgaccaggtt atcccggcg ctgacaaaga catcgttaaa    660
gtcttcacca gcgtatcag caagaaattc aacctgatgc tggaaaccaa agttaccgcc    720
```

```
gttgaagcga aagaagacgg catttatgtg acgatggaag gcaaaaaagc acccgctgaa    780
ccgcagcgtt acgacgccgt gctggtagcg attggtcgtg tgccgaacgg taaaaacctc    840
gacgcaggca agcaggcgt ggaagttgac gaccgtggtt tcatccgcgt tgacaaacag    900
ctgcgtacca acgtaccgca catctttgct atcggcgata tcgtcggtca accgatgctg    960
gcacacaaag gtgttcacga aggtcacgtt gccgctgaag ttatcgccgg taagaaacac    1020
tacttcgatc cgaaagttat cccgtccatc gcctataccg aaccagaagt tgcatgggtg    1080
ggtctgactg agaagaagc gaaagagaaa ggcatcagct atgaaaccgc caccttcccg    1140
tgggctgctt ctggtcgtgc tatcgcttcc gactgcgcag acggtatgac caagctgatt    1200
ttcgacaaag aatctcaccg tgtgatcggt ggtgcgattg tcggtactaa cggcggcgag    1260
ctgctgggtg aaatcggcct ggcaatcgaa atgggttgtg atgctgaaga catcgcactg    1320
accatccacg cgcacccgac tctgcacgag tctgtgggcc tggcggcaga agtgttcgaa    1380
ggtagcatta ccgacctgcc gaacccgaaa gcgaagaaga agtaa             1425
```

<210> SEQ ID NO 13
<211> LENGTH: 2664
<212> TYPE: DNA
<213> ORGANISM: Artificial Sequence
<220> FEATURE:
<223> OTHER INFORMATION: Synthetic (nucleotides coding aceE(pyruvate dehydrogenase))

<400> SEQUENCE: 13

```
atgtcagaac gtttcccaaa tgacgtggat ccgatcgaaa ctcgcgactg gctccaggcg    60
atcgaatcgg tcatccgtga agaaggtgtt gagcgtgctc agtatctgat cgaccaactg    120
cttgctgaag cccgcaaagg cggtgtaaac gtagccgcag gcacaggtat cagcaactac    180
atcaacacca tccccgttga agaacaaccg gagtatccgg gtaatctgga actggaacgc    240
cgtattcgtt cagctatccg ctggaacgcc atcatgacgg tgctgcgtgc gtcgaaaaaa    300
gacctcgaac tgggcggcca tatggcgtcc ttccagtctt ccgcaaccat ttatgatgtg    360
tgctttaacc acttcttccg tgcacgcaac gagcaggatg gcggcgacct ggtttacttc    420
cagggccaca tctccccggg cgtgtacgct cgtgctttcc tggaaggtcg tctgactcag    480
gagcagctgg ataacttccg tcaggaagtt cacggcaatg gcctctcttc ctatccgcac    540
ccgaaactga tgccggaatt ctggcagttc ccgaccgtat ctatgggtct gggtccgatt    600
ggtgctattt accaggctaa attcctgaaa tatctggaac accgtggcct gaaagatacc    660
tctaaacaaa ccgtttacgc gttcctcggt gacggtgaaa tggacgaacc ggaatccaaa    720
ggtgcgatca ccatcgctac ccgtgaaaaa ctggataacc tggtcttcgt tatcaactgt    780
aacctgcagc gtcttgacgg cccggtcacc ggtaacggca gatcatcaa cgaactggaa    840
ggcatcttcg aaggtgctgg ctggaacgtg atcaaagtga tgtgggggtag ccgttgggat    900
gaactgctgc gtaaggatac cagcggtaaa ctgatccagc tgatgaacga aaccgttgac    960
ggcgactacc agaccttcaa atcgaaagat ggtgcgtacg ttcgtgaaca cttcttcggt    1020
aaatatcctg aaaccgcagc actggttgca gactggactg acgagcagat ctgggcactg    1080
aaccgtggtg gtcacgatcc gaagaaaatc tacgctgcat tcaagaaagc gcaggaaacc    1140
aaaggcaaag cgacagtaat ccttgctcat accattaaag gttacggcat gggcgacgcg    1200
gctgaaggta aaaacatcgc gcaccaggtt aagaaaatga acatggacgg tgtgcgtcat    1260
atccgcgacc gtttcaatgt gccggtgtct gatgcagata tcgaaaaact gccgtacatc    1320
```

```
accttcccgg aaggttctga agagcatacc tatctgcacg ctcagcgtca gaaactgcac   1380
ggttatctgc caagccgtca gccgaacttc accgagaagc ttgagctgcc gagcctgcaa   1440
gacttcggcg cgctgttgga agagcagagc aaagagatct ctaccactat cgctttcgtt   1500
cgtgctctga acgtgatgct gaagaacaag tcgatcaaag atcgtctggt accgatcatc   1560
gccgacgaag cgcgtacttt cggtatggaa ggtctgttcc gtcagattgg tatttacagc   1620
ccgaacggtc agcagtacac cccgcaggac cgcgagcagg ttgcttacta taaagaagac   1680
gagaaaggtc agattctgca ggaagggatc aacgagctgg cgcaggttg ttcctggctg    1740 gcagcggcga cctcttacag caccaacaat ctgccgatga tcccgttcta catctattac   1800
tcgatgttcg gcttccagcg tattggcgat ctgtgctggg cggctggcga ccagcaagcg   1860
cgtggcttcc tgatcggcgg tacttccggt cgtaccaccc tgaacggcga aggtctgcag   1920
cacgaagatg gtcacagcca cattcagtcg ctgactatcc cgaactgtat ctcttacgac   1980
ccggcttacg cttacgaagt tgctgtcatc atgcatgacg tctggagcg tatgtacggt    2040 gaaaaacaag agaacgttta ctactacatc actacgctga acgaaaacta ccacatgccg   2100
gcaatgccgg aaggtgctga ggaaggtatc cgtaaaggta tctacaaact cgaaactatt   2160
gaaggtagca aaggtaaagt tcagctgctc ggctccggtt ctatcctgcg tcacgtccgt   2220
gaagcagctg agatcctggc gaaagattac ggcgtaggtt ctgacgttta tagcgtgacc   2280
tccttccacg agctggcgcg tgatggtcag gattgtgaac gctggaacat gctgcacccg   2340
ctggaaactc cgcgcgttcc gtatatcgct caggtgatga cgacgctcc ggcagtggca    2400 tctaccgact atatgaaact gttcgctgag caggtccgta cttacgtacc ggctgacgac   2460
taccgcgtac tgggtactga tggcttcggt cgttccgaca gccgtgagaa cctgcgtcac   2520
cacttcgaag ttgatgcttc ttatgtcgtg gttgcgcgc tgggcgaact ggctaaacgt    2580
ggcgaaatcg ataagaaagt ggttgctgac gcaatcgcca aattcaacat cgatgcagat   2640
aaagttaacc cgcgtctggc gtag                                         2664
```

<210> SEQ ID NO 14
<211> LENGTH: 1893
<212> TYPE: DNA
<213> ORGANISM: Artificial Sequence
<220> FEATURE:
<223> OTHER INFORMATION: Synthetic (nucleotides coding
      aceF(dihydrolipoamide acetyltransferase))

<400> SEQUENCE: 14

```
atggctatcg aaatcaaagt accggacatc ggggctgatg aagttgaaat caccgagatc    60
ctggtcaaag tgggcgacaa agttgaagcc gaacagtcgc tgatcaccgt agaaggcgac   120
aaagcctcta tggaagttcc gtctccgcag gcgggtatcg ttaaagagat caaagtctct   180
gttggcgata aaacccagac cggcgcactg attatgattt tcgattccgc cgacggtgca   240
gcagacgctg cacctgctca ggcagaagag aagaaagaag cagctccggc agcagcacca   300
gcggctgcgg cggcaaaaga cgttaacgtt ccggatatcg gcagcgacga agttgaagtg   360
accgaaatcc tggtgaaagt tggcgataaa gttgaagctg aacagtcgct gatcaccgta   420
gaaggcgaca aggcttctat ggaagttccg gctccgtttg ctggcaccgt gaaagagatc   480
aaagtgaacg tgggtgacaa agtgtctacc ggctcgctga ttatggtctt cgaagtcgcg   540
ggtgaagcag cgcggcagc tccgccggct aaacaggaag cagctccggc agcggcccct   600
gcaccagcgg ctggcgtgaa agaagttaac gttccggata tcggcggtga cgaagttgaa   660
```

```
gtgactgaag tgatggtgaa agtgggcgac aaagttgccg ctgaacagtc actgatcacc      720
gtagaaggcg acaaagcttc tatggaagtt ccggcgccgt ttgcaggcgt cgtgaaggaa      780
ctgaaagtca acgttggcga taaagtgaaa actggctcgc tgattatgat cttcgaagtt      840
gaaggcgcag cgcctgcggc agctcctgcg aaacaggaag cggcagcgcc ggcaccggca      900
gcaaaagctg aagccccggc agcagcacca gctgcgaaag cggaaggcaa atctgaattt      960
gctgaaaacg acgcttatgt tcacgcgact ccgctgatcc gccgtctggc acgcgagttt     1020
ggtgttaacc ttgcgaaagt gaagggcact ggccgtaaag gtcgtatcct cgcgcgaagac    1080 gttcaggctt acgtgaaaga agctatcaaa cgtgcagaag cagctccggc agcgactggc     1140
ggtggtatcc ctggcatgct gccgtggccg aaggtggact cagcaagtt tggtgaaatc      1200 gaagaagtgg aactgggccg catccagaaa atctctggtg cgaacctgag ccgtaactgg     1260
gtaatgatcc cgcatgttac tcacttcgac aaaaccgata tcaccgagtt ggaagcgttc     1320
cgtaaacagc agaacgaaga gcggcgaaaa cgtaagctgg atgtgaagat caccccggtt     1380
gtcttcatca tgaaagccgt tgctgcagct cttgagcaga tgcctcgctt caatagttcg     1440
ctgtcggaag acggtcagcg tctgaccctg aagaaataca tcaacatcgg tgtggcggtg     1500
gataccccga acggtctggt tgttccggta ttcaaagacg tcaacaagaa aggcatcatc     1560
gagctgtctc gcgagctgat gactatttct aagaaagcgc gtgacggtaa gctgactgcg     1620
ggcgaaatgc agggcggttg cttcaccatc tccagcatcg gcggcctggg tactacccac     1680
ttcgcgccga ttgtgaacgc gccggaagtg gctatcctcg gcgttccaa gtccgcgatg      1740 gagccggtgt ggaatggtaa agagttcgtg ccgcgtctga tgctgccgat ttctctctcc     1800
ttcgaccacc gcgtgatcga cggtgctgat ggtgcccgtt tcattaccat cattaacaac     1860
acgctgtctg acattcgccg tctggtgatg taa                                  1893
```

<210> SEQ ID NO 15
<211> LENGTH: 401
<212> TYPE: PRT
<213> ORGANISM: Artificial Sequence
<220> FEATURE:
<223> OTHER INFORMATION: Synthetic (formate dehydrogenase)

<400> SEQUENCE: 15

```
Met Ala Lys Val Leu Cys Val Leu Tyr Asp Asp Pro Val Asp Gly Tyr
 1               5                  10                  15

Pro Lys Thr Tyr Ala Arg Asp Asp Leu Pro Lys Ile Asp His Tyr Pro
             20                  25                  30

Gly Gly Gln Ile Leu Pro Thr Pro Lys Ala Ile Asp Phe Thr Pro Gly
         35                  40                  45

Gln Leu Leu Gly Ser Val Ser Gly Glu Leu Gly Leu Arg Glu Tyr Leu
     50                  55                  60

Glu Ser Asn Gly His Thr Leu Val Val Thr Ser Asp Lys Asp Gly Pro
 65                  70                  75                  80

Asp Ser Val Phe Glu Arg Glu Leu Val Asp Ala Asp Val Val Ile Ser
                 85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140
```

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
            165                 170                 175

Gly Trp Asn Ile Ala Asp Cys Val Ser His Ala Tyr Asp Leu Glu Ala
        180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Asp Arg His
210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
370                 375                 380

Gly Asn Ala Thr Gly Gly Ser Glu Glu Ala Ala Lys Phe Lys Lys Ala
385                 390                 395                 400

Val

<210> SEQ ID NO 16
<211> LENGTH: 1206
<212> TYPE: DNA
<213> ORGANISM: Artificial Sequence
<220> FEATURE:
<223> OTHER INFORMATION: Synthetic (nucleotides coding formate
      dehydrogenase)

<400> SEQUENCE: 16
atggctaagg tcctgtgcgt tctttacgat gatccagttg acggctaccc taagacctac    60
gcccgcgacg atcttccaaa gatcgaccac taccctggcg ccagatcct cccaaccca    120 aaggccatcg acttcacccc tggccagctc ctcggctccg tctccggcga actcggcctg    180
cgcgaatacc tcgaatccaa cggccacacc ctggtcgtta cctccgacaa ggacggccca    240
gactccgttt cgagcgcga gctggtcgat gcagatgtcg tcatctccca gccattctgg    300
ccagcctacc tgaccccaga gcgcatcgcc aaggctaaga acctgaagct cgctctcacc    360
gctggcatcg ttccgacca cgtcgatctt cagtccgcta tcgaccgcaa cgtcaccgtt    420
gcagaagtca cctactgcaa ctccatcagc gtcgccgagc acgtggttat gatgatcctg    480
tccctggttc gcaactacct gccttcccac gaatgggcgc gcaagggcgg ctggaacatc    540

```
gccgactgcg tctcccacgc ctacgacctc gaagctatgc acgtcggcac cgttgctgcc      600
ggccgcatcg gtctcgcagt tctgcgccgt ctggcaccat cgacgttca cctgcactac      660 accgaccgtc accgcctgcc tgaatccgtc gagaaggaac tcaacctcac ctggcacgca      720
acccgcgagg acatgtaccc agtttgcgac gtggttaccc tgaactgccc actgcaccca      780
gaaaccgagc acatgatcaa tgacgagacc ctgaagctgt tcaagcgtgg cgcctacatc      840
gtcaacaccg cacgcggcaa gctgtgcgac cgcgatgctg ttgcacgtgc tctcgaatcc      900
ggccgcctgg ccggctacgc cggcgacgtt tggttcccac agcctgcacc aaaggaccac      960
ccatggcgca ccatgccata caacggcatg accccacaca tctccggcac caccctgacc     1020
gcacaggcac gttacgcagc aggcacccgc gagatcctgg agtgcttctt cgagggccgt     1080
cctatccgcg acgaatacct catcgttcag ggcggcgctc ttgctggcac cggcgcacat     1140
tcctactcca aggcaatgc accggcggt tccgaagagg ccgctaagtt caagaaggca      1200
gtctga                                                                 1206

<210> SEQ ID NO 17
<211> LENGTH: 500
<212> TYPE: PRT
<213> ORGANISM: Artificial Sequence
<220> FEATURE:
<223> OTHER INFORMATION: Synthetic (MQO malate:quinone oxidoreductase)

<400> SEQUENCE: 17

Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
            20                  25                  30

Leu Arg Gln Leu Glu Pro Ser Trp Thr Gln Ile Val Phe Glu Arg Leu
        35                  40                  45

Asp Gly Pro Ala Gln Glu Ser Ser Pro Trp Asn Asn Ala Gly Thr
    50                  55                  60

Gly His Ser Ala Leu Cys Glu Leu Asn Tyr Thr Pro Glu Val Lys Gly
65                  70                  75                  80

Lys Val Glu Ile Ala Lys Ala Val Gly Ile Asn Glu Lys Phe Gln Val
                85                  90                  95

Ser Arg Gln Phe Trp Ser His Leu Val Glu Glu Gly Val Leu Ser Asp
            100                 105                 110

Pro Lys Glu Phe Ile Asn Pro Val Pro His Val Ser Phe Gly Gln Gly
        115                 120                 125

Ala Asp Gln Val Ala Tyr Ile Lys Ala Arg Tyr Glu Ala Leu Lys Asp
    130                 135                 140

His Pro Leu Phe Gln Gly Met Thr Tyr Ala Asp Asp Glu Ala Thr Phe
145                 150                 155                 160

Thr Glu Lys Leu Pro Leu Met Ala Lys Gly Arg Asp Phe Ser Asp Pro
                165                 170                 175

Val Ala Ile Ser Trp Ile Asp Glu Gly Thr Asp Ile Asn Tyr Gly Ala
            180                 185                 190

Gln Thr Lys Gln Tyr Leu Asp Ala Ala Glu Val Glu Gly Thr Glu Ile
        195                 200                 205

Arg Tyr Gly His Glu Val Lys Ser Ile Lys Ala Asp Gly Ala Lys Trp
    210                 215                 220

Ile Val Thr Val Lys Asn Val His Thr Gly Asp Thr Lys Thr Ile Lys
225                 230                 235                 240
```

```
Ala Asn Phe Val Phe Val Gly Ala Gly Gly Tyr Ala Leu Asp Leu Leu
            245                 250                 255

Arg Ser Ala Gly Ile Pro Gln Val Lys Gly Phe Ala Gly Phe Pro Val
            260                 265                 270

Ser Gly Leu Trp Leu Arg Cys Thr Asn Glu Glu Leu Ile Glu Gln His
            275                 280                 285

Ala Ala Lys Val Tyr Gly Lys Ala Ser Val Gly Ala Pro Pro Met Ser
            290                 295                 300

Val Pro His Leu Asp Thr Arg Val Ile Glu Gly Lys Gly Leu Leu
305                 310                 315                 320

Phe Gly Pro Tyr Gly Gly Trp Thr Pro Lys Phe Leu Lys Glu Gly Ser
            325                 330                 335

Tyr Leu Asp Leu Phe Lys Ser Ile Arg Pro Asp Asn Ile Pro Ser Tyr
            340                 345                 350

Leu Gly Val Ala Ala Gln Glu Phe Asp Leu Thr Lys Tyr Leu Val Thr
            355                 360                 365

Glu Val Leu Lys Asp Gln Asp Lys Arg Met Asp Ala Leu Arg Glu Tyr
            370                 375                 380

Met Pro Glu Ala Gln Asn Gly Asp Trp Glu Thr Ile Val Ala Gly Gln
385                 390                 395                 400

Arg Val Gln Val Ile Lys Pro Ala Gly Phe Pro Lys Phe Gly Ser Leu
            405                 410                 415

Glu Phe Gly Thr Thr Leu Ile Asn Asn Ser Glu Gly Thr Ile Ala Gly
            420                 425                 430

Leu Leu Gly Ala Ser Pro Gly Ala Ser Ile Ala Pro Ser Ala Met Ile
            435                 440                 445

Glu Leu Leu Glu Arg Cys Phe Gly Asp Arg Met Ile Glu Trp Gly Asp
            450                 455                 460

Lys Leu Lys Asp Met Ile Pro Ser Tyr Gly Lys Lys Leu Ala Ser Glu
465                 470                 475                 480

Pro Ala Leu Phe Glu Gln Gln Trp Ala Arg Thr Gln Lys Thr Leu Lys
            485                 490                 495

Leu Glu Glu Ala
            500

<210> SEQ ID NO 18
<211> LENGTH: 1503
<212> TYPE: DNA
<213> ORGANISM: Artificial Sequence
<220> FEATURE:
<223> OTHER INFORMATION: Synthetic (MQO malate:quinone oxidoreductase)

<400> SEQUENCE: 18
atgtcagatt ccccgaagaa cgcaccgagg attaccgatg aggcagatgt agttctcatt      60
ggtgccggta tcatgagctc cacgctgggt gcaatgctgc gtcagctgga gccaagctgg     120
actcagatcg tcttcgagcg tttggatgga ccggcacaag agtcgtcctc cccgtggaac     180
aatgcaggaa ccggccactc tgctctatgc gagctgaact acaccccaga ggttaagggc     240
aaggttgaaa ttgccaaggc tgtaggaatc aacgagaagt ccaggtttc ccgtcagttc      300 tggtctcacc tcgttgaaga gggagtgctg tctgatccta aggaattcat caaccctgtt     360
cctcacgtat ctttcggcca gggcgcagat caggttgcat acatcaaggc tcgctacgaa     420
gctttgaagg atcaccccact cttccagggc atgacctacg ctgacgatga agctaccttc     480
accgagaagc tgcctttgat ggcaaagggc cgtgacttct ctgatccagt agcaatctct     540
```

```
tggatcgatg aaggcaccga catcaactac ggtgctcaga ccaagcagta cctggatgca    600
gctgaagttg aaggcactga atccgctat ggccacgaag tcaagagcat caaggctgat     660
ggcgcaaagt ggatcgtgac cgtcaagaac gtacacactg gcgacaccaa gaccatcaag    720
gcaaacttcg tgttcgtcgg cgcaggcgga tacgcactgg atctgcttcg cagcgcaggc    780
atcccacagg tcaagggctt cgctggattc ccagtatccg gcctgtggct tcgttgcacc    840
aacgaggaac tgatcgagca gcacgcagcc aaggtatatg gcaaggcatc tgttggcgct    900
cctccaatgt ctgttcctca ccttgacacc cgcgttatcg agggtgaaaa gggtctgctc    960
tttggacctt acggtggctg gacccctaag ttcttgaagg aaggctccta cctggacctg   1020
ttcaagtcca tccgcccaga caacattcct tcctaccttg gcgttgctgc tcaggaattt   1080
gatctgacca gtaccttgt cactgaagtt ctcaaggacc aggacaagcg tatggatgct    1140
cttcgcgagt acatgccaga ggcacaaaac ggcgattggg agaccatcgt tgccggacag   1200
cgtgttcagg ttattaagcc tgcaggattc cctaagttcg gttccctgga attcggcacc   1260
accttgatca caactccga aggcaccatc gccggattgc tcggtgcttc ccctggagca    1320
tccatcgcac cttccgcaat gatcgagctg cttgagcgtt gcttcggtga ccgcatgatc   1380
gagtggggcg acaagctgaa ggacatgatc ccttcctacg caagaagct tgcttccgag    1440 ccagcactgt tgagcagca gtgggcacgc acccagaaga ccctgaagct tgaggaagcc    1500
taa                                                                 1503
```

<210> SEQ ID NO 19
<211> LENGTH: 610
<212> TYPE: PRT
<213> ORGANISM: Artificial Sequence
<220> FEATURE:
<223> OTHER INFORMATION: Synthetic (PCKG phosphoenolpyruvate
      carboxykinase)

<400> SEQUENCE: 19

```
Met Thr Thr Ala Ala Ile Arg Gly Leu Gln Gly Glu Ala Pro Thr Lys
1               5                   10                  15

Asn Lys Glu Leu Leu Asn Trp Ile Ala Asp Ala Val Glu Leu Phe Gln
            20                  25                  30

Pro Glu Ala Val Val Phe Val Asp Gly Ser Gln Ala Glu Trp Asp Arg
        35                  40                  45

Met Ala Glu Asp Leu Val Glu Ala Gly Thr Leu Ile Lys Leu Asn Glu
    50                  55                  60

Glu Lys Arg Pro Asn Ser Tyr Leu Ala Arg Ser Asn Pro Ser Asp Val
65                  70                  75                  80

Ala Arg Val Glu Ser Arg Thr Phe Ile Cys Ser Glu Lys Glu Glu Asp
                85                  90                  95

Ala Gly Pro Thr Asn Asn Trp Ala Pro Pro Gln Ala Met Lys Asp Glu
            100                 105                 110

Met Ser Lys His Tyr Ala Gly Ser Met Lys Gly Arg Thr Met Tyr Val
        115                 120                 125

Val Pro Phe Cys Met Gly Pro Ile Ser Asp Pro Asp Pro Lys Leu Gly
    130                 135                 140

Val Gln Leu Thr Asp Ser Glu Tyr Val Val Met Ser Met Arg Ile Met
145                 150                 155                 160

Thr Arg Met Gly Ile Glu Ala Leu Asp Lys Ile Gly Ala Asn Gly Ser
                165                 170                 175
```

```
Phe Val Arg Cys Leu His Ser Val Gly Ala Pro Leu Glu Pro Gly Gln
            180                 185                 190

Glu Asp Val Ala Trp Pro Cys Asn Asp Thr Lys Tyr Ile Thr Gln Phe
        195                 200                 205

Pro Glu Thr Lys Glu Ile Trp Ser Tyr Gly Ser Gly Tyr Gly Gly Asn
    210                 215                 220

Ala Ile Leu Ala Lys Lys Cys Tyr Ala Leu Arg Ile Ala Ser Val Met
225                 230                 235                 240

Ala Arg Glu Glu Gly Trp Met Ala Glu His Met Leu Ile Leu Lys Leu
                245                 250                 255

Ile Asn Pro Glu Gly Lys Ala Tyr His Ile Ala Ala Phe Pro Ser
            260                 265                 270

Ala Cys Gly Lys Thr Asn Leu Ala Met Ile Thr Pro Thr Ile Pro Gly
        275                 280                 285

Trp Thr Ala Gln Val Val Gly Asp Asp Ile Ala Trp Leu Lys Leu Arg
    290                 295                 300

Glu Asp Gly Leu Tyr Ala Val Asn Pro Glu Asn Gly Phe Phe Gly Val
305                 310                 315                 320

Ala Pro Gly Thr Asn Tyr Ala Ser Asn Pro Ile Ala Met Lys Thr Met
                325                 330                 335

Glu Pro Gly Asn Thr Leu Phe Thr Asn Val Ala Leu Thr Asp Asp Gly
            340                 345                 350

Asp Ile Trp Trp Glu Gly Met Asp Gly Asp Ala Pro Ala His Leu Ile
        355                 360                 365

Asp Trp Met Gly Asn Asp Trp Thr Pro Glu Ser Asp Glu Asn Ala Ala
370                 375                 380

His Pro Asn Ser Arg Tyr Cys Val Ala Ile Asp Gln Ser Pro Ala Ala
385                 390                 395                 400

Ala Pro Glu Phe Asn Asp Trp Glu Gly Val Lys Ile Asp Ala Ile Leu
                405                 410                 415

Phe Gly Gly Arg Arg Ala Asp Thr Val Pro Leu Val Thr Gln Thr Tyr
            420                 425                 430

Asp Trp Glu His Gly Thr Met Val Gly Ala Leu Leu Ala Ser Gly Gln
        435                 440                 445

Thr Ala Ala Ser Ala Glu Ala Lys Val Gly Thr Leu Arg His Asp Pro
    450                 455                 460

Met Ala Met Leu Pro Phe Ile Gly Tyr Asn Ala Gly Glu Tyr Leu Gln
465                 470                 475                 480

Asn Trp Ile Asp Met Gly Asn Lys Gly Gly Asp Lys Met Pro Ser Ile
                485                 490                 495

Phe Leu Val Asn Trp Phe Arg Arg Gly Glu Asp Gly Arg Phe Leu Trp
            500                 505                 510

Pro Gly Phe Gly Asp Asn Ser Arg Val Leu Lys Trp Val Ile Asp Arg
        515                 520                 525

Ile Glu Gly His Val Gly Ala Asp Glu Thr Val Gly His Thr Ala
    530                 535                 540

Lys Ala Glu Asp Leu Asp Leu Asp Gly Leu Asp Thr Pro Ile Glu Asp
545                 550                 555                 560

Val Lys Glu Ala Leu Thr Ala Pro Ala Glu Gln Trp Ala Asn Asp Val
                565                 570                 575

Glu Asp Asn Ala Glu Tyr Leu Thr Phe Leu Gly Pro Arg Val Pro Ala
            580                 585                 590

Glu Val His Ser Gln Phe Asp Ala Leu Lys Ala Arg Ile Ser Ala Ala
```

His Ala
610

<210> SEQ ID NO 20
<211> LENGTH: 1833
<212> TYPE: DNA
<213> ORGANISM: Artificial Sequence
<220> FEATURE:
<223> OTHER INFORMATION: Synthetic (PCKG phosphoenolpyruvate carboxykinase)

<400> SEQUENCE: 20

```
atgactactg ctgcaatcag gggccttcag ggcgaggcgc cgaccaagaa taaggaactg      60
ctgaactgga tcgcagacgc cgtcgagctc ttccagcctg aggctgttgt gttcgttgat     120
ggatcccagg ctgagtggga tcgcatggcg gaggatcttg ttgaagccgg taccctcatc     180
aagctcaacg aggaaaagcg tccgaacagc tacctagctc gttccaaccc atctgacgtt     240
gcgcgcgttg agtcccgcac cttcatctgc tccgagaagg aagaagatgc tggcccaacc     300
aacaactggg ctccaccaca ggcaatgaag gacgaaatgt ccaagcatta cgctggttcc     360
atgaaggggc gcaccatgta cgtcgtgcct ttctgcatgg gtccaatcag cgatccggac     420
cctaagcttg gtgtgcagct cactgactcc gagtacgttg tcatgtccat gcgcatcatg     480
acccgcatgg gtattgaagc gctggacaag atcggcgcga acggcagctt cgtcaggtgc     540
ctccactccg ttggtgctcc tttggagcca ggccaggaag acgttgcatg ccttgcaac      600
gacaccaagt acatcaccca gttcccagag accaaggaaa tttggtccta cggttccggc     660
tacggcggaa acgcaatcct ggcaaagaag tgctacgcac tgcgtatcgc atctgtcatg     720
gctcgcgaag aaggatggat ggctgagcac atgctcatcc tgaagctgat caacccagag     780
ggcaaggcgt accacatcgc agcagcattc ccatctgctt gtggcaagac caacctcgcc     840
atgatcactc caaccatccc aggctggacc gctcaggttg ttggcgacga catcgcttgg     900
ctgaagctgc gcgaggacgg cctctacgca gttaacccag aaaatggttt cttcggtgtt     960
gctccaggca ccaactacgc atccaaccca atcgcgatga gaccatggaa ccaggcaac    1020
accctgttca ccaacgtggc actcaccgac gacggcgaca tctggtggga aggcatggac    1080
ggcgacgccc cagctcacct cattgactgg atgggcaacg actggacccc agagtccgac    1140
gaaaacgctg ctcaccctaa ctcccgttac tgcgtagcaa tcgaccagtc cccagcagca    1200
gcacctgagt tcaacgactg gaaggcgtc aagatcgacg caatcctctt cggtggacgt    1260
cgcgcagaca ccgtcccact ggttacccag acctacgact gggagcacgg caccatggtt    1320
ggtgcactgc tcgcatccgg tcagaccgca gcttccgcag aagcaaaggt cggcacactc    1380
cgccacgacc caatggcaat gctcccattc attggctaca cgctggtga ataacctgcag    1440
aactggattg acatgggtaa caagggtggc gacaagatgc catccatctt cctggtcaac    1500
tggttccgcc gtgcgaaga tggacgcttc ctgtggcctg cttcggcga caactctcgc    1560
gttctgaagt gggtcatcga ccgcatcgaa ggccacgttg cgcagacga ccgttgtt    1620
ggacacaccg ctaaggccga agacctcgac ctcgacggcc tcgacacccc aattgaggat    1680
gtcaaggaag cactgaccgc tcctgcagag cagtgggcaa acgacgttga agacaacgcc    1740
gagtacctca ctttcctcgg accacgtgtt cctgcagagg ttcacagcca gttcgatgct    1800
ctgaaggccc gcatttcagc agctcacgct taa                                 1833
```

<210> SEQ ID NO 21
<211> LENGTH: 490
<212> TYPE: PRT
<213> ORGANISM: Artificial Sequence
<220> FEATURE:
<223> OTHER INFORMATION: Synthetic (GABD3 NAD-dependent aldehyde dehydrogenase)

<400> SEQUENCE: 21

```
Met Thr Ile Asn Val Ser Glu Leu Leu Ala Lys Val Pro Thr Gly Leu
1               5                   10                  15

Leu Ile Gly Asp Ser Trp Val Glu Ala Ser Asp Gly Thr Phe Asp
            20                  25                  30

Val Glu Asn Pro Ala Thr Gly Glu Thr Ile Ala Thr Leu Ala Ser Ala
            35                  40                  45

Thr Ser Glu Asp Ala Leu Ala Ala Leu Asp Ala Ala Cys Ala Val Gln
        50                  55                  60

Ala Glu Trp Ala Arg Met Pro Ala Arg Glu Arg Ser Asn Ile Leu Arg
65                  70                  75                  80

Arg Gly Phe Glu Leu Val Ala Glu Arg Ala Glu Phe Ala Thr Leu
                85                  90                  95

Met Thr Leu Glu Met Gly Lys Pro Leu Ala Glu Ala Arg Gly Glu Val
            100                 105                 110

Thr Tyr Gly Asn Glu Phe Leu Arg Trp Phe Ser Glu Glu Ala Val Arg
        115                 120                 125

Leu Tyr Gly Arg Tyr Gly Thr Thr Pro Glu Gly Asn Leu Arg Met Leu
    130                 135                 140

Thr Ala Leu Lys Pro Val Gly Pro Cys Leu Leu Ile Thr Pro Trp Asn
145                 150                 155                 160

Phe Pro Leu Ala Met Ala Thr Arg Lys Val Ala Pro Ala Ile Ala Ala
                165                 170                 175

Gly Cys Val Met Val Leu Lys Pro Ala Arg Leu Thr Pro Leu Thr Ser
            180                 185                 190

Gln Tyr Phe Ala Gln Thr Met Leu Asp Ala Gly Leu Pro Ala Gly Val
        195                 200                 205

Leu Asn Val Val Ser Gly Ala Ser Ala Ser Ala Ile Ser Asn Pro Ile
    210                 215                 220

Met Glu Asp Asp Arg Leu Arg Lys Val Ser Phe Thr Gly Ser Thr Pro
225                 230                 235                 240

Val Gly Gln Gln Leu Leu Lys Lys Ala Ala Asp Lys Val Leu Arg Thr
                245                 250                 255

Ser Met Glu Leu Gly Gly Asn Ala Pro Phe Ile Val Phe Glu Asp Ala
            260                 265                 270

Asp Leu Asp Leu Ala Ile Glu Gly Ala Met Gly Ala Lys Met Arg Asn
        275                 280                 285

Ile Gly Glu Ala Cys Thr Ala Ala Asn Arg Phe Leu Val His Glu Ser
    290                 295                 300

Val Ala Asp Glu Phe Gly Arg Arg Phe Ala Ala Arg Leu Glu Glu Gln
305                 310                 315                 320

Val Leu Gly Asn Gly Leu Asp Glu Gly Val Thr Val Gly Pro Leu Val
                325                 330                 335

Glu Glu Lys Ala Arg Asp Ser Val Ala Ser Leu Val Asp Ala Ala Val
            340                 345                 350

Ala Glu Gly Ala Thr Val Leu Thr Gly Gly Lys Ala Gly Thr Gly Ala
        355                 360                 365
```

| Gly | Tyr | Phe | Tyr | Glu | Pro | Thr | Val | Leu | Thr | Gly | Val | Ser | Thr | Asp | Ala |
|---|---|---|---|---|---|---|---|---|---|---|---|---|---|---|---|
| | 370 | | | | 375 | | | | | 380 | | | | | |

| Ala | Ile | Leu | Asn | Glu | Glu | Ile | Phe | Gly | Pro | Val | Ala | Pro | Ile | Val | Thr |
|---|---|---|---|---|---|---|---|---|---|---|---|---|---|---|---|
| 385 | | | | | 390 | | | | | 395 | | | | | 400 |

| Phe | Gln | Thr | Glu | Glu | Glu | Ala | Leu | Arg | Leu | Ala | Asn | Ser | Thr | Glu | Tyr |
|---|---|---|---|---|---|---|---|---|---|---|---|---|---|---|---|
| | | | | 405 | | | | | 410 | | | | | 415 | |

| Gly | Leu | Ala | Ser | Tyr | Val | Phe | Thr | Gln | Asp | Thr | Ser | Arg | Ile | Phe | Arg |
|---|---|---|---|---|---|---|---|---|---|---|---|---|---|---|---|
| | | | | 420 | | | | | 425 | | | | | 430 | |

| Val | Ser | Asp | Gly | Leu | Glu | Phe | Gly | Leu | Val | Gly | Val | Asn | Ser | Gly | Val |
|---|---|---|---|---|---|---|---|---|---|---|---|---|---|---|---|
| | | | 435 | | | | | 440 | | | | | 445 | | |

| Ile | Ser | Asn | Ala | Ala | Ala | Pro | Phe | Gly | Gly | Val | Lys | Gln | Ser | Gly | Met |
|---|---|---|---|---|---|---|---|---|---|---|---|---|---|---|---|
| | 450 | | | | | 455 | | | | | 460 | | | | |

| Gly | Arg | Glu | Gly | Gly | Leu | Glu | Gly | Ile | Glu | Glu | Tyr | Thr | Ser | Val | Gln |
|---|---|---|---|---|---|---|---|---|---|---|---|---|---|---|---|
| 465 | | | | | 470 | | | | | 475 | | | | | 480 |

| Tyr | Ile | Gly | Ile | Arg | Asp | Pro | Tyr | Ala | Gly |
|---|---|---|---|---|---|---|---|---|---|
| | | | | 485 | | | | | 490 |

<210> SEQ ID NO 22
<211> LENGTH: 1473
<212> TYPE: DNA
<213> ORGANISM: Artificial Sequence
<220> FEATURE:
<223> OTHER INFORMATION: Synthetic (Corynebacterium
glutamicum(Ncgl0049))

<400> SEQUENCE: 22

| | |
|---|---|
| atgactatta atgtctccga actacttgcc aaagtcccca cgggtctact gattggtgat | 60 |
| tcctgggtgg aagcatccga cggcggtact ttcgatgtgg aaaacccagc gacgggtgaa | 120 |
| acaatcgcaa cgctcgcgtc tgctacttcc gaggatgcac tggctgctct tgatgctgca | 180 |
| tgcgctgttc aggccgagtg ggctaggatg ccagcgcgcg agcgttctaa tattttacgc | 240 |
| cgcggttttg agctcgtagc agaacgtgca gaagagttcg ccaccctcat gaccttggaa | 300 |
| atgggcaagc ctttggctga agctcgcggc gaagtcacct acggcaacga attcctgcgc | 360 |
| tggttctctg aggaagcagt tcgtctgtat ggccgttacg gaaccacacc agaaggcaac | 420 |
| ttgcggatgc tgaccgccct caagccagtt ggccgtgcc tcctgatcac cccatggaac | 480 |
| ttcccactag caatggctac ccgcaaggtc gcacctgcga tcgctgcagg ttgtgtcatg | 540 |
| gtgctcaagc cagctcgact taccccgctg acctccagt attttgctca gaccatgctt | 600 |
| gatgccggtc ttccagcagg tgtcctcaat gtggtctccg gtgcttccgc ctctgcgatt | 660 |
| tccaacccga ttatgaaga cgatcgcctt cgtaaagtct ccttcaccgg ctccaccca | 720 |
| gttggccagc agctgctcaa aaaggctgcc gataaagttc tgcgcacctc catggaactt | 780 |
| ggtggcaacg cacctttcat tgtcttcgag gacgccgacc tagatctcgc gatcgaaggt | 840 |
| gccatgggtg ccaaaatgcg caacatcggc gaagcttgca ccgcagccaa ccgtttctta | 900 |
| gtccacgaat ccgtcgccga tgaattcggc cgtcgcttcg ctgcccgcct gaagagcaa | 960 |
| gtcctaggca acggcctcga cgaaggcgtc accgtgggcc cctggttga ggaaaaagca | 1020 |
| cgagacagcg ttgcatcgct tgtcgacgcg gccgtcgccg aaggtgccac cgtcctcacc | 1080 |
| ggcggcaagg ccggcacagg tgcaggctac ttctacgaac caacggtgct cacgggagtt | 1140 |
| tcaacagatg cggctatcct gaacgaagag atcttcggtc ccgtcgcacc gatcgtcacc | 1200 |
| ttccaaaccg aggaagaagc cctgcgtcta gccaactcca ccgaatacgg actggcctcc | 1260 |
| tatgtgttca cccaggacac ctcacgtatt ttccgcgtct ccgatggtct cgagttcggc | 1320 |

| | |
|---|---|
| ctagtgggcg tcaattccgg tgtcatctct aacgctgctg cacctttgg tggcgtaaaa | 1380 |
| caatccggaa tgggccgcga aggtggtctc gaaggaatcg aggagtacac ctccgtgcag | 1440 |
| tacatcggta tccgggatcc ttacgccggc tag | 1473 |

<210> SEQ ID NO 23
<211> LENGTH: 1362
<212> TYPE: DNA
<213> ORGANISM: Artificial Sequence
<220> FEATURE:
<223> OTHER INFORMATION: Synthetic (Corynebacterium glutamicum(Ncgl0463))

<400> SEQUENCE: 23

| | |
|---|---|
| gtgtctttga ccttcccagt aatcaacccc agcgatggct ccaccatcac cgagctagaa | 60 |
| aaccacgatt ccacccagtg gatgtccgcg ctctctgatg cagttgcagc tggtccttca | 120 |
| tgggctgcga aaactccccg cgaaagatcc gtggtactca ccgcaatctt cgaagcactg | 180 |
| accgaacgcg cccaagaact tgcagagatc atccacctgg aagctggaaa atccgttgca | 240 |
| gaagctcttg gtgaagtcgc ttatggtgca gaatacttcc gttggtttgc ggaagaagca | 300 |
| gtgcgcctgc ccgccgcta cggacagtca ccttccggaa tcggtcacat cgccgtcacc | 360 |
| cgcgcacccg tgggaccagt gctggcgatc accccatgga atttccccat cgccatggcc | 420 |
| acccgcaaaa tcgccccagc cctggccgct ggttgccccg tgttggtgaa acctgcttcc | 480 |
| gaaaccccac tgaccatggt caaagtgggg gagatcatcg cctccgtctt tgatacctttt | 540 |
| aatatcccgc agggcttggt ctcaatcatc accaccactc gagatgcaga gctatcggca | 600 |
| gaactcatgg ctgatcctcg cttggctaaa gtcaccttca ctggatcaac caacgtggga | 660 |
| cgcatcctgg tccgccaatc cgcggaccga ctgctgcgca cctccatgga actcggcgga | 720 |
| aatgcagctt ttgttatcga cgaagccgca gacctcgacg aagccgtatc cggtgccatc | 780 |
| gccgcaaaac tccgcaacgc cggccaagta tgcatcgcag ctaaccgttt cttggttcat | 840 |
| gaatcccgcg ctgccgaatt cacctcaaag ctggcgacag ccatgcagaa cactcccatt | 900 |
| gggccggtga tttctgcccg ccaacgcgac cggatcgcag cactagtgga tgaagccatc | 960 |
| accgacggcg cccgcctcat catcggtggg gaggtccccg acggctccgg cttcttctat | 1020 |
| ccagccacca tcttggccga tgtccctgca cagtcacgga ttgtgcatga ggaaatcttc | 1080 |
| ggacctgtgg ccaccattgc cactttcacc gacttggccg aaggcgttgc acaagcaaat | 1140 |
| tccaccgaat tcggcctcgc agcctacgga ttcagcaaca atgtgaaagc aacacagtac | 1200 |
| atggcggaac acttggaagc cggaatggtc ggaatcaaca gaggcgccat ctctgaccca | 1260 |
| gcagcacctt ttggcggcat cggacaatcc ggcttcggca gagaaggcgg aaccgaagga | 1320 |
| atcgaagaat atctctccgt gcgttacctc gctttgccgt ga | 1362 |

<210> SEQ ID NO 24
<211> LENGTH: 1566
<212> TYPE: DNA
<213> ORGANISM: Artificial Sequence
<220> FEATURE:
<223> OTHER INFORMATION: Synthetic (Corynebacterium glutamicum(Ncgl2619))

<400> SEQUENCE: 24

| | |
|---|---|
| atgatcaaac gtcttccttt aggtccgctg cctaaagaac ttcatcagac tctgcttgat | 60 |
| ctgaccgcaa atgcccaaga tgcggcgaaa gtggaggtta tagcgccatt tactggcgag | 120 |
| accctcggat ttgttttttga tggtgatgag caagacgtcg agcatgcttt tgcactttca | 180 |

```
agggcagccc agaaaaagtg ggtgcacacc acggcagtgg aacgaagaa gatcttcctg      240 aagtttcatg atctggtatt gaaaaaccgt gagctgctca tggacatcgt gcagttggaa      300
acaggcaaaa atcgagcatc ggctgccgat gaggtgttgg acgttgcgat caccacccgc      360
ttctacgcaa acaatgcagg aaagttttta aatgacaaga aacgccccgg cgcgcttccg      420
atcatcacga aaacacacac acagtatgtg cccaagggag tggtcgggca gatcacgccg      480
tggaattacc ctttaacttt gggagtatct gatgctgttc cggcgctgct ggcaggaaac      540
gcagtggtgg ctaaacctga cctcgcgaca ccttcctcct gcttgatcat ggtgcacctg      600
ctcattgaag ccggtctgcc gcgtgatttg atgcaggttg tcaccggccc tggcgatatt      660
gttggcggtg cgattgcagc tcagtgtgat ttcctcatgt tcactggatc cacggccacg      720
ggccggatct gggtcggac aatgggtgag cgtttggtgg gtttctctgc ggaattaggc      780
ggaaagaacc ctcttattgt ggccaaggat gcagatctgg acaaggtgga agctgagctt      840
ccgcaggcgt gtttttccaa ctcggggcaa ttgtgtgtct ccactgaacg tatttatgtc      900
gaggaagacg tgtacgagga ggtgattgca cggtttagca aggcggcgaa agccatgtcc      960
attggtgccg gatttgagtg gaaatatgag atgggttcgt tgatcaatca ggcgcagctg     1020
gatcgggtga gcacctttgt tgatcaggct aaagctgcgg gcgccacggt gctgtgcggt     1080
ggcaagtcac gccctgatat tggtcccttc ttctatgagc ccacggtatt ggcggatgtc     1140
ccagagggca ccccactgct cacggaggaa gtcttcgggc cggtggtgtt catcgaaaag     1200
gtagccacac tggaagaagc cgtcgataag gcaaatggca cgccctacgg cctgaatgcg     1260
tccgtctttg ggtcgtcgga aaccggcaat cttgttgcag ccagctgga agctggcggt      1320 atcggtatta atgatggcta cgccgcgacg tgggcgagcg tgtccacgcc tctgggtggc     1380
atgaagcagt cggggctggg gcaccgccat ggtgcggagg gaattacaaa atatgcggag     1440
atccgaaaca tcgcggagca cgctggatg tctatgcgtg ggccggccaa aatgccgcga     1500
aaggtgtact cagacaccgt ggccacagcg ctaaagctgg gcaaaatctt taagttttg      1560 ccgtag                                                                1566
```

<210> SEQ ID NO 25
<211> LENGTH: 36
<212> TYPE: DNA
<213> ORGANISM: Artificial Sequence
<220> FEATURE:
<223> OTHER INFORMATION: Synthetic (sequences for removing LDH)

<400> SEQUENCE: 25
gcaggcatgc aagcttctag tctggggagc gaaacc                               36

<210> SEQ ID NO 26
<211> LENGTH: 35
<212> TYPE: DNA
<213> ORGANISM: Artificial Sequence
<220> FEATURE:
<223> OTHER INFORMATION: Synthetic (sequences for removing LDH)

<400> SEQUENCE: 26
gagctcagtc agtcatggac gccacgagga agatg                                35

<210> SEQ ID NO 27
<211> LENGTH: 35
<212> TYPE: DNA
<213> ORGANISM: Artificial Sequence
<220> FEATURE:

<223> OTHER INFORMATION: Synthetic (sequences for removing LDH)

<400> SEQUENCE: 27
tgactgactg agctcctgga caaagaccca gagct         35

<210> SEQ ID NO 28
<211> LENGTH: 36
<212> TYPE: DNA
<213> ORGANISM: Artificial Sequence
<220> FEATURE:
<223> OTHER INFORMATION: Synthetic (sequences for removing LDH)

<400> SEQUENCE: 28
ggccagtgcc aagcttttgc gggcaccaac gtaatg         36

<210> SEQ ID NO 29
<211> LENGTH: 230
<212> TYPE: DNA
<213> ORGANISM: Artificial Sequence
<220> FEATURE:
<223> OTHER INFORMATION: Synthetic (deleted ldh sequences)

<400> SEQUENCE: 29
acccagtgga tatcctgacc tacgcagtgt ggaaattctc cggcttggaa tggaaccgcg         60
tgatcggctc cggaactgtc ctggactccg ctcgattccg ctacatgctg ggcgaactct        120
acgaagtggc accaagctcc gtccacgcct acatcatcgg cgaacacggc gacactgaac        180
ttccagtcct gtcctccgcg accatcgcag gcgtatcgct tagccgaatg                   230

<210> SEQ ID NO 30
<211> LENGTH: 46
<212> TYPE: DNA
<213> ORGANISM: Artificial Sequence
<220> FEATURE:
<223> OTHER INFORMATION: Synthetic (sequences for deleting Mqo)

<400> SEQUENCE: 30
ctgcaggtcg actctagaga agaagtagtc cgtcatgccg tgaacc         46

<210> SEQ ID NO 31
<211> LENGTH: 32
<212> TYPE: DNA
<213> ORGANISM: Artificial Sequence
<220> FEATURE:
<223> OTHER INFORMATION: Synthetic (sequences for deleting Mqo)

<400> SEQUENCE: 31
tagaagatta ttttgactg acgcgtgggg cg         32

<210> SEQ ID NO 32
<211> LENGTH: 40
<212> TYPE: DNA
<213> ORGANISM: Artificial Sequence
<220> FEATURE:
<223> OTHER INFORMATION: Synthetic (sequences for deleting Mqo)

<400> SEQUENCE: 32
gtcaaaaata atcttctaac tgctttcttt aaagcacccg         40

<210> SEQ ID NO 33
<211> LENGTH: 45
<212> TYPE: DNA
<213> ORGANISM: Artificial Sequence
<220> FEATURE:
<223> OTHER INFORMATION: Synthetic (sequences for deleting Mqo)

<400> SEQUENCE: 33
ctcggtaccc ggggatcctc ttaaagcctg agatagcgag ttcca          45

<210> SEQ ID NO 34
<211> LENGTH: 28
<212> TYPE: DNA
<213> ORGANISM: Artificial Sequence
<220> FEATURE:
<223> OTHER INFORMATION: Synthetic (sequences for deleting pckG)

<400> SEQUENCE: 34
gctctagagt catgtattta ggtagggc          28

<210> SEQ ID NO 35
<211> LENGTH: 33
<212> TYPE: DNA
<213> ORGANISM: Artificial Sequence
<220> FEATURE:
<223> OTHER INFORMATION: Synthetic (sequences for deleting pckG)

<400> SEQUENCE: 35
atctgaaagc atgcatttgc aacgacacca agt          33

<210> SEQ ID NO 36
<211> LENGTH: 33
<212> TYPE: DNA
<213> ORGANISM: Artificial Sequence
<220> FEATURE:
<223> OTHER INFORMATION: Synthetic (sequences for deleting pckG)

<400> SEQUENCE: 36
gttgcaaatg catgctttca gatacagaac tag          33

<210> SEQ ID NO 37
<211> LENGTH: 26
<212> TYPE: DNA
<213> ORGANISM: Artificial Sequence
<220> FEATURE:
<223> OTHER INFORMATION: Synthetic (sequences for deleting pckG)

<400> SEQUENCE: 37
gctctagaca gtcgttgaac tcaggt          26

<210> SEQ ID NO 38
<211> LENGTH: 25
<212> TYPE: DNA
<213> ORGANISM: Artificial Sequence
<220> FEATURE:
<223> OTHER INFORMATION: Synthetic (primer sequences for substituting
      Pro to Ser in PYC)

<400> SEQUENCE: 38
gctctagatt gagcacaccg tgact          25

<210> SEQ ID NO 39
<211> LENGTH: 22
<212> TYPE: DNA
<213> ORGANISM: Artificial Sequence
<220> FEATURE:
<223> OTHER INFORMATION: Synthetic (primer sequences for substituting
      Pro to Ser in PYC)

<400> SEQUENCE: 39
ccggattcat tgccgatcac tc          22

<210> SEQ ID NO 40
<211> LENGTH: 28
<212> TYPE: DNA
<213> ORGANISM: Artificial Sequence
<220> FEATURE:
<223> OTHER INFORMATION: Synthetic (primer sequences for substituting Pro to Ser in PYC)

<400> SEQUENCE: 40
gctctagact gtcccacgga tcctcaaa                                28

<210> SEQ ID NO 41
<211> LENGTH: 19
<212> TYPE: DNA
<213> ORGANISM: Artificial Sequence
<220> FEATURE:
<223> OTHER INFORMATION: Synthetic (primer sequences for substituting Pro to Ser in PYC)

<400> SEQUENCE: 41
ctgaaggagg tgcgagtga                                          19

<210> SEQ ID NO 42
<211> LENGTH: 945
<212> TYPE: DNA
<213> ORGANISM: Artificial Sequence
<220> FEATURE:
<223> OTHER INFORMATION: Synthetic (Corynebacterium glutamicum ATCC 13032(NCgl2810))

<400> SEQUENCE: 42
atgaaagaaa ccgtcggtaa caagattgtc ctcattggcg caggagatgt tggagttgca    60
tacgcatacg cactgatcaa ccagggcatg gcagatcacc ttgcgatcat cgacatcgat   120
gaaaagaaac tcgaaggcaa cgtcatggac ttaaaccatg gtgttgtgtg ggccgattcc   180
cgcacccgcg tcaccaaggg cacctacgct gactgcgaag acgcagccat ggttgtcatt   240
tgtgccggcg cagcccaaaa gccaggcgag acccgcctcc agctggtgga caaaaacgtc   300
aagattatga atccatcgt cggcgatgtc atggacagcg gattcgacgg catcttcctc   360
gtggcgtcca acccagtgga tatcctgacc tacgcagtgt ggaaattctc cggcttggaa   420
tggaaccgcg tgatcggctc cggaactgtc ctggactccg ctcgattccg ctacatgctg   480
ggcgaactct acgaagtggc accaagctcc gtccacgcct acatcatcgg cgaacacggc   540
gacactgaac ttccagtcct gtcctccgcg accatcgcag gcgtatcgct tagccgaatg   600
ctggacaaag acccagagct tgagggccgt ctagagaaaa ttttcgaaga cacccgcgac   660
gctgcctatc acattatcga cgccaagggc tccacttcct acggcatcgg catgggtctt   720
gctcgcatca cccgcgcaat cctgcagaac caagacgttg cagtcccagt ctctgcactg   780
ctccacggtg aatacggtga ggaagacatc tacatcggca ccccagctgt ggtgaaccgc   840
cgaggcatcc gccgcgttgt cgaactagaa atcaccgacc acgagatgga acgcttcaag   900
cattccgcaa atacctgcg cgaaattcag aagcagttct tctaa                   945

<210> SEQ ID NO 43
<211> LENGTH: 23
<212> TYPE: DNA
<213> ORGANISM: Artificial Sequence
<220> FEATURE:
<223> OTHER INFORMATION: Synthetic (sequence for deleting gabD3)

<400> SEQUENCE: 43
attcggtgag gaatccggcg gtg                                          23

<210> SEQ ID NO 44
<211> LENGTH: 26
<212> TYPE: DNA
<213> ORGANISM: Artificial Sequence
<220> FEATURE:
<223> OTHER INFORMATION: Synthetic (sequence for deleting gabD3)

<400> SEQUENCE: 44
ctatgagaca gtcgtcctgt acccat                                       26

<210> SEQ ID NO 45
<211> LENGTH: 5390
<212> TYPE: DNA
<213> ORGANISM: Artificial Sequence
<220> FEATURE:
<223> OTHER INFORMATION: Synthetic (polynucleotides coding succinyl-
      CoA:coenzyme A transferase, succinate semialdehyde dehydrogenase
      and 4-hydroxybutyrate dehydrogenase)

<400> SEQUENCE: 45
tctagaatga ctattaatgt ctccgaacta cttgccaaag tccccacggg tctactgatt    60
ggtgattcct gggtggaagc atccgacggc ggtactttcg atgtgaaaaa cccagcgacg   120
ggtgaaacaa tcgcaacgct cgcgtctgct acttccgagg atgcactggc tgctcttgat   180
gctgcatgcg ctgttcaggc cgagtgggct aggatgccag cgcgcgagcg ttctaatatt   240
ttacgccgcg gttttgagct cgtagcagaa cgtgcagaag agttcgccac cctcatgacc   300
ttggaaatgg gcaagccttt ggctgaagct cgcggcgaaa tcacctacgg caacgaattc   360
ctgcgctggt tctctgagga agcagttcgt ctgtatggcc gttacggaac cacaccagaa   420
ggcaacttgc ggatgctgac cgccctcaag ccagttggcc cgtgcctcct gatcacccca   480
tggaacttcc cactagcaat ggctactaga tgattttgca tctgctgcga aatctttgtt   540
tccccgctaa agttgaggac aggttgcacc ggagttgact cgacgaatta tccaatgtga   600
gtaggtttgg tgcgtgagtt ggaaaaattc gccatactcg cccttgggtt ctgtcagctc   660
aagaattctt gagtgaccga tgctctgatt gacctaactg cttgacacat tgcatttcct   720
acaatcttta gaggagacac aacatgtcta aaggaatcaa gaatagccaa ttgaaaaaaa   780
agaacgtcaa ggccagtaac gttgctgaga agatcgaaga gaaggtggaa agaccgaca   840 aggtcgttga aaggctgct gaggtgaccg aaaagcgaat tcgaaactta agctccagg    900 aaaaagttgt gaccgcagat gtcgcagctg acatgatcga aatggcatg atcgtcgcaa    960 ttagcggctt cacgccatcc gggtatccaa aggaggttcc aaaagccctt actaagaagg  1020
ttaatgcgct ggaggaggag ttcaaggtga cgctgtatac cggttctagc acaggcgctg  1080
atattgacgg agaatgggcg aaggcaggaa taatcgaacg gcgtatccca taccagacca  1140
actctgacat gaggaaaaaa ataaacgatg gttcaatcaa gtacgcagat atgcacctga  1200
gccacatggc tcaatacatt aactattctg tgattcctaa ggttgacatt gccatcatcg  1260
aggcggtggc cattaccgag gaaggggata ttattcctag tactggaatc ggcaacacag  1320
ctacgtttgt cgagaatgcg gataaggtaa ttgtggaaat aaacgaggct cagccgcttg  1380
agttggaagg catggcagat atctataccc tgaagaaccc tccacgtcgc gagcccatcc  1440
cgatagtcaa cgcaggcaac cgcataggga ccacttacgt cacctgtggc tctgaaaaaa  1500
tctgcgcgat cgtcatgacc aacacccaag acaaaacccg cccactcacc gaagtttctc  1560
ctgtcagtca ggcaatctcc gataacctga ttggcttcct gaacaaagaa gtagaggagg  1620

```
gtaaactccc aaaaaacctg ctccccatac agtcaggtgt cggttcggtt gctaacgccg    1680
tgcatcccgg actctgcgaa tcaaacttca aaaatttgag ctgctacaca gaagtgatcc    1740
aggattcgat gttgaagctg atcaaatgtg aaaggcaga tgtggtgtcc ggcacctcga     1800
tctcgccatc accggaaatg ctgcccgagt tcataaagga cataaatttt tttcgcgaga    1860
agatagtact gcgccccag gaaatatcta ataatccgga aatagctcgt cgtataggag     1920
tgatctccat aaaacactgct ttggaagtag acatctacgg taatgtgaac tccacgcatg   1980
tcatgggctc caagatgatg aacggcatcg gcggcagcgg cgactttgcc cgcaacgcat    2040
acctcaccat attcactacg gagtccatcg cgaagaaggg cgacatttcc tctatcgttc    2100
ctatggtttc ccacgtggac cacaccgagc atgacgtaat ggtcatcgtt accgaacagg    2160
gggttgcgga tctccgcggt cttccctc gggaaaagc cgtggcgata attgagaatt       2220
gcgtccaccc ggattacaag gatatgctca tggagtactt cgaggaggct tgtaagtcct    2280
caggtggcaa cacccacac aaccttgaaa aagccctatc ctggcacact aagttcataa     2340
aaactggctc gatgaagtaa ttagaggaga cacaacatgg agattaaaga gatggtcagt    2400
cttgcgcgca aagctcagaa ggagtatcag gccacccata accaagaagc tgtggacaac    2460
atctgccgag ctgcagcgaa ggttatttac gaaaatgcag caattctggc ccgcgaggca    2520
gtggacgaaa ccggcatggg tgtttacgag cacaaggtgg ccaagaatca aggcaagtcc    2580
aaaggtgttt ggtacaacct gcataacaag aagtcgattg gcatcctcaa tatcgatgag    2640
cgtaccggca tgatcgagat cgcaaaacct atcggggttg taggcgccgt tacgccaacc    2700 accaaccta tcgttactcc gatgagcaac atcatctttg ctcttaagac ctgcaacgcc     2760
atcattatcg ccccacaccc gcgctccaaa agtgctctg cccacgcagt tcggctgatc     2820
aaagaggcta tcgctccgtt caacgtgccc gaaggtatgg ttcagatcat cgaggagcct    2880
agcatcgaga agacgcagga attgatgggc gccgtagacg tggtcgttgc taccgggggc    2940
atgggcatgg tcaagtctgc ctactcctca gggaagcctt ctttcggtgt cggagccggc    3000
aatgttcagg tgatagtgga cagcaacatc gatttcgaag cggctgcaga aaagatcatc    3060
accggacgtg ccttcgacaa cggtatcatc tgctcaggcg aacagtccat catctacaac    3120
gaggctgaca aggaagcagt tttcacagca ttccgcaacc acggtgcgta cttttgcgac    3180
gaggccgagg gagatcgggc tcgtgcagcg atcttgaaa atggagccat cgcgaaagat     3240
gttgtgggcc agtccgttgc ctttattgcc aagaaggcga acattaatat ccccgagggt    3300
actcgtattc tcgtggtcga agctcgcgga gtaggcgccg aagatgtcat ctgtaaagaa    3360
aagatgtgtc cagtcatgtg cgccctctcc tacaagcact tcgaagaggg ggtagagatc    3420
gcaaggacga acctcgcaaa cgaaggcaat ggccatacct gtgctatcca ctccaacaac    3480
caagcacaca tcatcttggc aggctcggag ctgaccgtgt ctcgcatcgt ggtcaacgcg    3540
ccaagtgcta ccacagcagg cggtcacatc cagaacggtc ttgccgtcac caatactcta    3600
ggctgcggct cttggggtaa caactcgatc tccgaaaact tcacttataa acacctgctc    3660
aacatttcac gcatcgcccc gttgaactcc agcattcata tcccagatga taaggaaatc    3720
tgggaactct aattagagga gacacaacat gcagctttc aagctcaaga gcgtcacaca     3780
tcactttgat acttttgcag agtttgccaa ggaattctgt ctcggtgaac gcgacttggt    3840
aattaccaac gagttcatct acgaaccgta tatgaaggca tgccagctgc cttgtcattt    3900
tgtgatgcag gagaaatacg gccaaggcga gccttctgac gagatgatga acaacatcct   3960
```

```
agcagatatc cgtaatatcc agttcgaccg cgtgatcggg atcggaggtg gtacggttat    4020
tgacatctca aaactctttg ttctgaaggg attaaatgat gttctcgacg cgttcgatcg    4080
caagattccc cttatcaaag agaaagaact gatcattgtg cccaccacct gcggaaccgg    4140
ctcggaggtg acgaacattt ccatcgccga gatcaagtcc cggcacacca agatgggttt    4200
ggctgacgat gcaattgttg ctgaccacgc cataatcatc cctgaacttc tgaagagctt    4260
gcccttccac ttctatgcat gctccgcaat cgatgctctt attcatgcca tcgagtcata    4320
cgtttctcca aaagcgtctc catactcccg tctgttcagt gaggcggcgt gggacattat    4380
cctggaagtt ttcaagaaaa tcgccgaaca cggcccagag taccgcttcg agaagctggg    4440
ggaaatgatc atggccagca actatgccgg tatcgctttc ggcaacgcag gcgttggcgc    4500
cgtccacgct ctatcctacc cgttgggcgg caactatcac gtgccgcatg gagaagcaaa    4560
ctatcagttc ttcaccgagg tctttaaagt ataccaaaag aagaatccgt tcggctatat    4620
tgtcgaactc aactggaagc tctccaagat tctgaactgc cagccagagt acgtgtaccc    4680
gaagctggat gaactgctcg gttgccttct taccaagaaa cctttgcacg aatacggcat    4740
gaaggacgaa gaggttcgtg gcttcgcgga atcggtcctg aagacccagc aacgcttgct    4800
cgccaacaac tacgtcgaac ttactgtcga tgagatcgaa ggtatctacc gacgtctcta    4860
ctaacatatg gcggccgcaa gcttgcctcg acgaaggcgt caccgtgggc cccctggttg    4920
aggaaaaagc acgagacagc gttgcatcgc ttgtcgacgc cgccgtcgcc gaaggtgcca    4980
ccgtcctcac cggcggcaag gccggcacag gtgcaggcta cttctacgaa ccaacggtgc    5040
tcacgggagt ttcaacagat gcggctatcc tgaacgaaga gatcttcggt cccgtcgcac    5100
cgatcgtcac cttccaaacc gaggaagaag ccctgcgtct agccaactcc accgaatacg    5160
gactggcctc ctatgtgttc acccaggaca cctcacgtat tttccgcgtc tccgatggtc    5220
tcgagttcgg cctagtgggc gtcaattccg gtgtcatctc taacgctgct gcaccttttg    5280
gtggcgtaaa acaatccgga atgggccgcg aaggtggtct cgaaggaatc gaggagtaca    5340
cctccgtgca gtacatcggt atccgggatc cttacgccgg ctaggctagc                5390
```

<210> SEQ ID NO 46
<211> LENGTH: 4625
<212> TYPE: DNA
<213> ORGANISM: Artificial Sequence
<220> FEATURE:
<223> OTHER INFORMATION: Synthetic (polynucleotides coding alpha-ketoglutarate synthase)

<400> SEQUENCE: 46

```
tctagaggat ccccgggtag gagcacgcag gagcttgccg aactcacacc atcgcaatat      60
ctggcaaaaa tggaatggcg cctagacaat cccaacctag caacattgg atccaacaag      120 attgttgcga ctggatataa gacctattac aagttgtgta tgagtatcct gaaattgctc      180
gcttaacacc ccataaagag ggtgaagatt taagttcagg tgcgatctgg gtgaacagta      240
cataaatatc atctttcgct aatggaaagc cccagctcac cgaattctcc attcgtttta      300
attgcttcgt taattaaaac gccatataaa aaccggcgca ttgccggtat ttttccagga      360
gaatttaatg attttgcatc tgctgcgaaa tctttgtttc cccgctaaag ttgaggacag      420
gttgacacgg agttgactcg acgaattatc caatgtgagt aggtttggtg cgtgagttgg      480
aaaaattcgc catactcgcc cttgggttct gtcagctcaa gaattcttga gtgaccgatg      540
ctctgattga cctaactgct tgacacattg catttcctac aatctttaga ggagacacaa      600
```

```
catgtaccga aaattccgcg acgatccatc ttctgtcgat ccttcatggc atgaattcct    660
tgtggattat tcacccgagc caacttctca acctgctgcc gaacctacgc gtgtgacttc    720
gccattggtt gctgaacgcg cagcagcagc ggctccccaa gctccaccaa agcccgcaga    780
tactgccgct gcaggtaacg gtgtagttgc tgcattggca gcaaagaccg ctgtgccacc    840
tccagctgag ggtgatgagg tagctgtgct tcgtggagca gcagctgcgg ttgtgaagaa    900
catgtctgct tccctcgagg tgccgactgc aacgtctgtt cgcgccgtac ccgccaaact    960
gctgatcgac aatcgcattg tgatcaacaa tcaactcaag cgtacgcgag gcggcaagat   1020
ctcctttact cacttgttgg gctacgccct cgttcaggcc gtcaagaaat cccgaacat    1080
gaaccgccat tacaccgaag tagacggaaa gccgacagcc gtcacgccag cacacacgaa   1140
cctgggcctc gctatcgatc tgcagggtaa agacggtaaa cgttcgcttg tcgtcgcagg   1200
catcaagcgc tgcgagacaa tgcgtttcgc ccagtttgtt actgcgtatg aggatatcgt   1260
tcgccgtgcg cgtgacggta agctcacaac cgaggacttc gcaggggtca cgatcagcct   1320
tacgaaccct gggaccattg gtaccgttca ttcggtccca cgactgatgc caggccaagg   1380
ggccatcatc ggcgttgggg ctatggaata ccctgcggag ttccaggag cctctgagga    1440
gcgcattgca gaacttggca tcggtaagct gatcaccctg actagcacct atgaccaccg   1500
cattattcag ggggcagaaa gcggtgattt cctccgaacc atccatgagc tcctgctctc   1560
cgatggcttt tgggatgagg ttttccgaga actttccatt ccgtacctcc cggtccgctg   1620
gagcaccgac aaccccgatt ccatcgtcga taaaaacgcc cgagtcatga acctcatcgc   1680
tgcgtaccgt aaccgtggcc acttgatggc cgatacggac cccttgcgct ggacaaggc    1740
tcgcttccgc tcgcacccgg atcttgaagt gctgacccat ggcctgaccc tttgggatct   1800
ggatcgtgtc ttcaaggtcg acggttttgc cggagcacag tacaagaaac ttcgagacgt   1860
cctcggcctc ctgcgtgatg cgtactgccg tcacatcggc gtggaatatg cccacatcct   1920
tgaccctgaa cagaaggagt ggttggagca acgcgtcgag actaaacacg tgaagccaac   1980
cgtggcgcag caaaagtaca tcctgtcgaa gttgaacgca gccgaggcct tcgagacttt   2040
cttgcagacc aaatatgttg gccaaaagcg gttctctctg gagggcgcgg agtccgtgat   2100
tcctatgatg gatgccgcta tcgaccaatg cgcagagcac ggactggacg aggtcgttat   2160
cggcatgcct catcgcggcc gccttaatgt cttggcaaat attgtgggaa agccgtattc   2220
ccagatcttc accgagttcg aaggtaatct gaacccatcc caggctcatg gctcgggcga   2280
tgttaagtac cacctgggcg ccaccggttt gtatctccag atgtttggtg ataacgatat   2340
tcaagttagc cttaccgcta atccgtccca cctggaggct gtggatccgg tgctcgaagg   2400
tctcgtgcgg gcgaagcagg atctgctcga ccacggttcc atcgactctg atggtcagcg   2460
cgccttctca gtcgttccct tgatgttgca cggagatgcg gcattcgctg gtcaaggagt   2520
agtggcggaa accctcaacc tcgcgaacct gccgggctac cgcgttgggg gcactatcca   2580
cattattgtc aacaaccaga ttggctttac cacagctccc gagtactctc gctcttcaga   2640
atactgtact gacgtcgcga agatgatcgg tgcgccgatc ttccatgtca acggcgacga   2700
cccagaggca tgtgtctggg tcgcacgtct cgccgtcgat ttccgccagc ggttcaagaa   2760
agacgtcgtg attgacatgc tttgctaccg ccgccgcggg cacaatgagg gagatgaccc   2820
atcaatgacc aacccataca tgtacgacgt tgtagatacc aagcgcgcgcg cgcgtaaatc   2880
ctacaccgag gcccttatcg gtcggggcga tatctccatg aaagaggctg aagatgcact   2940
tcgggattac cagggccagt tggaacgcgt ttttaacgaa gttcgcgagc tggaaaaaca   3000
```

```
tggagttcag ccgtccgagt cggttgaaag cgatcaaatg attccagctg gcttggcgac    3060
cgccgttgat aaatccttgc tggctcggat cggagatgca ttcctggcgc tgcctaatgg    3120
tttcaccgcg cacccacgcg tgcagccggt acttgagaag cgccgtgaaa tggcctacga    3180
aggcaagatt gactgggcat tcggtgaact gctggctctg ggttcgctgg tgcggaggtg    3240
taagcttgtt cgactgtccg gccaggattc ccgtcggggc accttctccc agcgccactc    3300
tgtcctgatc gatcggcaca caggcgaaga attcacccct ctgcagcttc tcgctaccaa    3360
ctcagacgga tcgccaaccg gaggaaagtt cctcgtatat gatagccccc tctcagaata    3420
cgcagcagtg ggctttgagt acggctacac tgtaggcaat cccgacgcgg tggtcctttg    3480
ggaggctcag ttcggtgact tgttaacgg cgcacagtcc atcatcgacg agtttatttc    3540
aagcggcgaa gcaaagtggg gtcaattgtc caatgtcgtg ctgctcctgc acatggaca    3600 cgaaggtcag gggccggacc acacctccgc tcgtattgaa cgcttcctcc aactgtgggc    3660
agaaggaagc atgaccattg ctatgccatc cacccatca aattattttc acctgctgcg    3720
gcgccatgcc ttggacggga tccagcggcc tcttattgtc ttcacaccaa agtccatgct    3780
ccgccacaaa gctgcagtgt ctgaaatcaa agacttcacc gaaatcaagt tccgctccgt    3840
tctggaagaa ccaacctacg aggacggaat cggcgaccgc aacaaggtgt cccgtatcct    3900
gttgacttcc ggaaaactct attacgaact tgcagcgcgt aaggcaaagg ataaccggaa    3960
tgacctcgcc atcgtgcgcc tggagcagct cgcaccttg cctcgtcgac gcctccgcga    4020
aaccctggac cgttacgaaa acgttaagga atttttctgg gtgcaggaag agcctgctaa    4080
ccagggtgcc tggccacgtt ttgggctcga gcttcccgaa ctcctgccgg ataaactcgc    4140
tggtattaaa cggatctccc gtcgtgctat gtctgcccct tccagcggca gctctaaggt    4200
gcacgcggtg gagcaacagg agatcctgga tgaagcattt ggttaactca gcttcaggct    4260
atgtttgcgc agttcatgta ataacttgta gtaaataaat cgggccttcc caaaagattc    4320
tttcttggga aaggcccgat tttggtattt gaggtctttt agtggagtgt cttagacatt    4380
tgtcgcaaca ctgactaact ggcggtcgta tttgtcagtt gtcgcacttt caagcatgac    4440
ccacgcagca tcttcatatg aggtgtacat tccggtttct cgatttactc gaacaacacg    4500
attctcaagc ttactgcgtg ccccttgagc atccataagg gaagtgacgg gaaactgtct    4560
ttaagccctg aacgtaagag atcaacgatg ctagtggcct gaatggcgaa tggcgataag    4620
ctagc                                                                4625
```

<210> SEQ ID NO 47
<211> LENGTH: 2444
<212> TYPE: DNA
<213> ORGANISM: Artificial Sequence
<220> FEATURE:
<223> OTHER INFORMATION: Synthetic (polynucleotides coding formate dehydrogenase)

<400> SEQUENCE: 47

```
ggatccgtgt caccgatcat tcgtaaattg agtatccccg agttcaccac caacaccca      60 gtgttggtgg atatctacat cgcagcgatg aactatgaca aagcaatcag ggatacccgg    120
atcgaagtct ggcggagaaa ctcccagaac cccggattca cagcagtggc agcgctgatg    180
gatgatcagg tcgtgggcgt ggcctatggc ttcaatggca gcccagatca ttggtggcaa    240
caccaattac gccggggact ccgacaacaa atgattttgc atctgctgcg aaatctttgt    300
ttccccgcta agttgaggca caggttgaca cggagttgac tcgacgaatt atccaatgtg    360
```

```
agtaggtttg gtgcgtgagt tggaaaaatt cgccatactc gcccttgggt tctgtcagct    420
caagaattct tgagtgaccg atgctctgat tgacctaact gcttgacaca ttgcatttcc    480
tacaatcttt agaggagaca caacctcgag gtcgacggta tcgataagct tatggctaag    540
gtcctgtgcg ttctttacga tgatccagtt gacggctacc ctaagaccta cgcccgcgac    600
gatcttccaa agatcgacca ctaccctggc ggccagatcc tcccaacccc aaaggccatc    660
gacttcaccc ctggccagct cctcggctcc gtctccggcg aactcggcct gcgcgaatac    720
ctcgaatcca acggccacac cctggtcgtt acctccgaca aggacggccc agactccgtt    780
ttcgagcgcg agctggtcga tgcagatgtc gtcatctccc agccattctg gccagcctac    840
ctgaccccag agcgcatcgc caaggctaag aacctgaagc tcgctctcac cgctggcatc    900
ggttccgacc acgtcgatct tcagtccgct atcgaccgca acgtcaccgt tgcagaagtc    960
acctactgca actccatcag cgtcgccgag cacgtggtta tgatgatcct gtccctggtt   1020
cgcaactacc tgccttccca cgaatgggcg cgcaagggcg gctggaacat cgccgactgc   1080
gtctcccacg cctacgacct cgaagctatg cacgtcggca ccgttgctgc cggccgcatc   1140
ggtctcgcag ttctgcgccg tctggcacca ttcgacgttc acctgcacta caccgaccgt   1200
caccgcctgc ctgaatccgt cgagaaggaa ctcaacctca cctggcacgc aacccgcgag   1260
gacatgtacc cagtttgcga cgtggttacc ctgaactgcc cactgcaccc agaaaccgag   1320
cacatgatca atgacgagac cctgaagctg ttcaagcgtg gcgcctacat cgtcaacacc   1380
gcacgcggca agctgtgcga ccgcgatgct gttgcacgtg ctctcgaatc cggccgcctg   1440
gccggctacg ccggcgacgt ttggttccca cagcctgcac caaaggacca cccatggcgc   1500
accatgccat acaacggcat gaccccacac atctccggca ccaccctgac cgcacaggca   1560
cgttacgcag caggcacccg cgagatcctg gagtgcttct tcgagggccg tcctatccgc   1620
gacgaatacc tcatcgttca gggcggcgct cttgctggca ccggcgcaca ttcctactcc   1680
aagggcaatg ccaccggcgg ttccgaagag gccgctaagt tcaagaaggc agtctgactg   1740
cagcccgggg gatccactag ttctagagcg gccgccaccg cggtggagct catttagcgg   1800
atgattctcg ttcaacttcg gccgaagcca cttcgtctgt cataatgaca gggatggttt   1860
cggccgtttt tgcaaataaa acgaaaggct cagtcgaaag actgggcctt tcgttttatc   1920
tgttgtttgt cggtgaacgc tctcctgagt aggacaaatc cgccgggagc ggatttgaac   1980
gttgcgaagc aacggcccgg agggtggcgg gcaggacgcc cgccataaac tgccaggcat   2040
caaattaagc agaaggccat cctgacggat ggcctttttg cgtttctaca aactcttcct   2100
gtcgtcatat ctacaagcca tcccccacag atacggtgg aggcccgacg gaagaggaaa   2160
tccatatcat ccacaactac tttgaggttg cggaagttca tgttcagcct ggcttccaag   2220
gtcacggcat tggccgaaag ctgatgcatg aactgttaaa agacaaacaa aacacttttg   2280
ccattttgtc tacacccgag gtcgacgatg aggcgaacca tgcgtttagc ctgtatcgct   2340
ctctcggctt cactgacttg ctcaggcagt ttaggtttga cggggatcaa cggccgtttg   2400
ccgtattgat caccgccctc cccttcatg attcctaaga attc                     2444
```

<210> SEQ ID NO 48
<211> LENGTH: 887
<212> TYPE: PRT
<213> ORGANISM: Escherichia coli

<400> SEQUENCE: 48

```
Met Ser Glu Arg Phe Pro Asn Asp Val Asp Pro Ile Glu Thr Arg Asp
 1               5                  10                  15
Trp Leu Gln Ala Ile Glu Ser Val Ile Arg Glu Glu Gly Val Glu Arg
            20                  25                  30
Ala Gln Tyr Leu Ile Asp Gln Leu Leu Ala Glu Ala Arg Lys Gly Gly
            35                  40                  45
Val Asn Val Ala Ala Gly Thr Gly Ile Ser Asn Tyr Ile Asn Thr Ile
 50                  55                  60
Pro Val Glu Glu Gln Pro Glu Tyr Pro Gly Asn Leu Glu Leu Glu Arg
 65                  70                  75                  80
Arg Ile Arg Ser Ala Ile Arg Trp Asn Ala Ile Met Thr Val Leu Arg
                85                  90                  95
Ala Ser Lys Lys Asp Leu Glu Leu Gly Gly His Met Ala Ser Phe Gln
            100                 105                 110
Ser Ser Ala Thr Ile Tyr Asp Val Cys Phe Asn His Phe Arg Ala
            115                 120                 125
Arg Asn Glu Gln Asp Gly Gly Asp Leu Val Tyr Phe Gln Gly His Ile
            130                 135                 140
Ser Pro Gly Val Tyr Ala Arg Ala Phe Leu Glu Gly Arg Leu Thr Gln
145                 150                 155                 160
Glu Gln Leu Asp Asn Phe Arg Gln Glu Val His Gly Asn Gly Leu Ser
                165                 170                 175
Ser Tyr Pro His Pro Lys Leu Met Pro Glu Phe Trp Gln Phe Pro Thr
            180                 185                 190
Val Ser Met Gly Leu Gly Pro Ile Gly Ala Ile Tyr Gln Ala Lys Phe
            195                 200                 205
Leu Lys Tyr Leu Glu His Arg Gly Leu Lys Asp Thr Ser Lys Gln Thr
            210                 215                 220
Val Tyr Ala Phe Leu Gly Asp Gly Glu Met Asp Glu Pro Glu Ser Lys
225                 230                 235                 240
Gly Ala Ile Thr Ile Ala Thr Arg Glu Lys Leu Asp Asn Leu Val Phe
                245                 250                 255
Val Ile Asn Cys Asn Leu Gln Arg Leu Asp Gly Pro Val Thr Gly Asn
            260                 265                 270
Gly Lys Ile Ile Asn Glu Leu Glu Gly Ile Phe Glu Gly Ala Gly Trp
            275                 280                 285
Asn Val Ile Lys Val Met Trp Gly Ser Arg Trp Asp Glu Leu Leu Arg
            290                 295                 300
Lys Asp Thr Ser Gly Lys Leu Ile Gln Leu Met Asn Glu Thr Val Asp
305                 310                 315                 320
Gly Asp Tyr Gln Thr Phe Lys Ser Lys Asp Gly Ala Tyr Val Arg Glu
                325                 330                 335
His Phe Phe Gly Lys Tyr Pro Glu Thr Ala Ala Leu Val Ala Asp Trp
            340                 345                 350
Thr Asp Glu Gln Ile Trp Ala Leu Asn Arg Gly Gly His Asp Pro Lys
            355                 360                 365
Lys Ile Tyr Ala Ala Phe Lys Lys Ala Gln Glu Thr Lys Gly Lys Ala
            370                 375                 380
Thr Val Ile Leu Ala His Thr Ile Lys Gly Tyr Gly Met Gly Asp Ala
385                 390                 395                 400
Ala Glu Gly Lys Asn Ile Ala His Gln Val Lys Lys Met Asn Met Asp
                405                 410                 415
Gly Val Arg His Ile Arg Asp Arg Phe Asn Val Pro Val Ser Asp Ala
```

```
                420             425             430
Asp Ile Glu Lys Leu Pro Tyr Ile Thr Phe Pro Glu Gly Ser Glu Glu
            435                 440             445

His Thr Tyr Leu His Ala Gln Arg Gln Lys Leu His Gly Tyr Leu Pro
450                 455                 460

Ser Arg Gln Pro Asn Phe Thr Glu Lys Leu Glu Leu Pro Ser Leu Gln
465                 470                 475                 480

Asp Phe Gly Ala Leu Leu Glu Glu Gln Ser Lys Glu Ile Ser Thr Thr
                485                 490                 495

Ile Ala Phe Val Arg Ala Leu Asn Val Met Leu Lys Asn Lys Ser Ile
                500                 505                 510

Lys Asp Arg Leu Val Pro Ile Ile Ala Asp Glu Ala Arg Thr Phe Gly
            515                 520                 525

Met Glu Gly Leu Phe Arg Gln Ile Gly Ile Tyr Ser Pro Asn Gly Gln
        530                 535                 540

Gln Tyr Thr Pro Gln Asp Arg Glu Gln Val Ala Tyr Tyr Lys Glu Asp
545                 550                 555                 560

Glu Lys Gly Gln Ile Leu Gln Glu Gly Ile Asn Glu Leu Gly Ala Gly
                565                 570                 575

Cys Ser Trp Leu Ala Ala Ala Thr Ser Tyr Ser Thr Asn Asn Leu Pro
                580                 585                 590

Met Ile Pro Phe Tyr Ile Tyr Tyr Ser Met Phe Gly Phe Gln Arg Ile
            595                 600                 605

Gly Asp Leu Cys Trp Ala Ala Gly Asp Gln Gln Ala Arg Gly Phe Leu
        610                 615                 620

Ile Gly Gly Thr Ser Gly Arg Thr Thr Leu Asn Gly Glu Gly Leu Gln
625                 630                 635                 640

His Glu Asp Gly His Ser His Ile Gln Ser Leu Thr Ile Pro Asn Cys
                645                 650                 655

Ile Ser Tyr Asp Pro Ala Tyr Ala Tyr Glu Val Ala Val Ile Met His
                660                 665                 670

Asp Gly Leu Glu Arg Met Tyr Gly Glu Lys Gln Glu Asn Val Tyr Tyr
            675                 680                 685

Tyr Ile Thr Thr Leu Asn Glu Asn Tyr His Met Pro Ala Met Pro Glu
        690                 695                 700

Gly Ala Glu Glu Gly Ile Arg Lys Gly Ile Tyr Lys Leu Glu Thr Ile
705                 710                 715                 720

Glu Gly Ser Lys Gly Lys Val Gln Leu Leu Gly Ser Gly Ser Ile Leu
                725                 730                 735

Arg His Val Arg Glu Ala Ala Glu Ile Leu Ala Lys Asp Tyr Gly Val
                740                 745                 750

Gly Ser Asp Val Tyr Ser Val Thr Ser Phe Thr Glu Leu Ala Arg Asp
            755                 760                 765

Gly Gln Asp Cys Glu Arg Trp Asn Met Leu His Pro Leu Glu Thr Pro
        770                 775                 780

Arg Val Pro Tyr Ile Ala Gln Val Met Asn Asp Ala Pro Ala Val Ala
785                 790                 795                 800

Ser Thr Asp Tyr Met Lys Leu Phe Ala Glu Gln Val Arg Thr Tyr Val
                805                 810                 815

Pro Ala Asp Asp Tyr Arg Val Leu Gly Thr Asp Gly Phe Gly Arg Ser
            820                 825                 830

Asp Ser Arg Glu Asn Leu Arg His His Phe Glu Val Asp Ala Ser Tyr
        835                 840                 845
```

Val Val Val Ala Ala Leu Gly Glu Leu Ala Lys Arg Gly Glu Ile Asp
    850                 855                 860

Lys Lys Val Val Ala Asp Ala Ile Ala Lys Phe Asn Ile Asp Ala Asp
865                 870                 875                 880

Lys Val Asn Pro Arg Leu Ala
            885

<210> SEQ ID NO 49
<211> LENGTH: 2664
<212> TYPE: DNA
<213> ORGANISM: Escherichia coli

<400> SEQUENCE: 49

```
atgtcagaac gtttcccaaa tgacgtggat ccgatcgaaa ctcgcgactg gctccaggcg      60
atcgaatcgg tcatccgtga agaaggtgtt gagcgtgctc agtatctgat cgaccaactg     120
cttgctgaag cccgcaaagg cggtgtaaac gtagccgcag gcacaggtat cagcaactac     180
atcaacacca tccccgttga agaacaaccg agtatccgg gtaatctgga actggaacgc      240
cgtattcgtt cagctatccg ctggaacgcc atcatgacgg tgctgcgtgc gtcgaaaaaa     300
gacctcgaac tgggcggcca tatggcgtcc ttccagtctt ccgcaaccat ttatgatgtg     360
tgctttaacc acttcttccg tgcacgcaac gagcaggatg cggcgaccct ggtttacttc     420
cagggccaca tctccccggg cgtgtacgct cgtgctttcc tggaaggtcg tctgactcag     480
gagcagctgg ataacttccg tcaggaagtt cacggcaatg cctctcttc ctatccgcac      540 ccgaaactga tgccggaatt ctggcagttc cgaccgtat ctatgggtct gggtccgatt      600
ggtgctattt accaggctaa attcctgaaa tatctggaac accgtggcct gaaagatacc     660
tctaaacaaa ccgtttacgc gttcctcggt acggtgaaa tggacgaacc ggaatccaaa      720
ggtgcgatca ccatcgctac ccgtgaaaaa ctggataacc tggtcttcgt tatcaactgt     780
aacctgcagc gtcttgacgg cccggtcacc ggtaacggca agatcatcaa cgaactggaa     840
ggcatcttcg aaggtgctgg ctggaacgtg atcaaagtga tgtggggtag ccgttgggat    900
gaactgctgc gtaaggatac cagcggtaaa ctgatccagc tgatgaacga accgttgac     960 ggcgactacc agaccttcaa atcgaaagat ggtgcgtacg ttcgtgaaca cttcttcggt    1020
aaatatcctg aaaccgcagc actggttgca gactggactg acgagcagat ctgggcactg    1080
aaccgtggtg gtcacgatcc gaagaaaatc tacgctgcat tcaagaaagc gcaggaaacc    1140
aaaggcaaag cgacagtaat ccttgctcat accattaaag gttacggcat gggcgacgcg    1200
gctgaaggta aaaacatcgc gcaccaggtt aagaaaatga catggacgg tgtgcgtcat     1260 atccgcgacc gtttcaatgt gccggtgtct gatgcagata tcgaaaaact gccgtacatc    1320
accttcccgg aaggttctga agagcatacc tatctgcacg ctcagcgtca gaaactgcac    1380
ggttatctgc aagccgtca gccgaacttc accgagaagc ttgagctgcc gagcctgcaa     1440
gacttcggcg cgctgttgga agagcagagc aaagagatct ctaccactat cgctttcgtt    1500
cgtgctctga acgtgatgct gaagaacaag tcgatcaaag atcgtctggt accgatcatc    1560
gccgacgaag cgcgtacttt cggtatggaa ggtctgttcc gtcagattgg tatttacagc    1620
ccgaacggtc agcagtacac cccgcaggac cgcgagcagg ttgcttacta taagaagac     1680 gagaaaggtc agattctgca ggaagggatc aacgagctgg cgcaggttg ttcctggctg     1740 gcagcggcga cctcttacag caccaacaat ctgccgatga tcccgttcta catctattac    1800
tcgatgttcg gcttccagcg tattggcgat ctgtgctggg cggctggcga ccagcaagcg    1860
```

```
cgtggcttcc tgatcggcgg tacttccggt cgtaccaccc tgaacggcga aggtctgcag    1920
cacgaagatg gtcacagcca cattcagtcg ctgactatcc cgaactgtat ctcttacgac    1980
ccggcttacg cttacgaagt tgctgtcatc atgcatgacg gtctggagcg tatgtacggt    2040
gaaaaacaag agaacgttta ctactacatc actacgctga acgaaaacta ccacatgccg    2100
gcaatgccgg aaggtgctga ggaaggtatc cgtaaaggta tctacaaact cgaaactatt    2160
gaaggtagca aagtaaagt tcagctgctc ggctccggtt ctatcctgcg tcacgtccgt    2220
gaagcagctg agatcctggc gaaagattac ggcgtaggtt ctgacgttta tagcgtgacc    2280
tccttcaccg agctggcgcg tgatggtcag gattgtgaac gctggaacat gctgcacccg    2340
ctggaaactc cgcgcgttcc gtatatcgct caggtgatga acgacgctcc ggcagtggca    2400
tctaccgact atatgaaact gttcgctgag caggtccgta cttacgtacc ggctgacgac    2460
taccgcgtac tgggtactga tggcttcggt cgttccgaca gccgtgagaa cctgcgtcac    2520
cacttcgaag ttgatgcttc ttatgtcgtg gttgcggcgc tgggcgaact ggctaaacgt    2580
ggcgaaatcg ataagaaagt ggttgctgac gcaatcgcca aattcaacat cgatgcagat    2640
aaagttaacc cgcgtctggc gtaa                                          2664
```

<210> SEQ ID NO 50
<211> LENGTH: 630
<212> TYPE: PRT
<213> ORGANISM: Escherichia coli

<400> SEQUENCE: 50

```
Met Ala Ile Glu Ile Lys Val Pro Asp Ile Gly Ala Asp Glu Val Glu
1               5                   10                  15

Ile Thr Glu Ile Leu Val Lys Val Gly Asp Lys Val Glu Ala Glu Gln
            20                  25                  30

Ser Leu Ile Thr Val Glu Gly Asp Lys Ala Ser Met Glu Val Pro Ser
        35                  40                  45

Pro Gln Ala Gly Ile Val Lys Glu Ile Lys Val Ser Val Gly Asp Lys
    50                  55                  60

Thr Gln Thr Gly Ala Leu Ile Met Ile Phe Asp Ser Ala Asp Gly Ala
65                  70                  75                  80

Ala Asp Ala Ala Pro Ala Gln Ala Glu Glu Lys Lys Glu Ala Ala Pro
                85                  90                  95

Ala Ala Ala Pro Ala Ala Ala Ala Lys Asp Val Asn Val Pro Asp
            100                 105                 110

Ile Gly Ser Asp Glu Val Glu Val Thr Glu Ile Leu Val Lys Val Gly
        115                 120                 125

Asp Lys Val Glu Ala Glu Gln Ser Leu Ile Thr Val Glu Gly Asp Lys
    130                 135                 140

Ala Ser Met Glu Val Pro Ala Pro Phe Ala Gly Thr Val Lys Glu Ile
145                 150                 155                 160

Lys Val Asn Val Gly Asp Lys Val Ser Thr Gly Ser Leu Ile Met Val
                165                 170                 175

Phe Glu Val Ala Gly Glu Ala Gly Ala Ala Pro Ala Ala Lys Gln
            180                 185                 190

Glu Ala Ala Pro Ala Ala Ala Pro Ala Pro Ala Ala Gly Val Lys Glu
        195                 200                 205

Val Asn Val Pro Asp Ile Gly Gly Asp Glu Val Glu Val Thr Glu Val
    210                 215                 220
```

```
Met Val Lys Val Gly Asp Lys Val Ala Ala Glu Gln Ser Leu Ile Thr
225                 230                 235                 240

Val Glu Gly Asp Lys Ala Ser Met Glu Val Pro Ala Pro Phe Ala Gly
            245                 250                 255

Val Val Lys Glu Leu Lys Val Asn Val Gly Asp Lys Val Lys Thr Gly
            260                 265                 270

Ser Leu Ile Met Ile Phe Glu Val Glu Gly Ala Ala Pro Ala Ala Ala
        275                 280                 285

Pro Ala Lys Gln Glu Ala Ala Pro Ala Pro Ala Ala Lys Ala Glu
    290                 295                 300

Ala Pro Ala Ala Ala Pro Ala Ala Lys Ala Glu Gly Lys Ser Glu Phe
305                 310                 315                 320

Ala Glu Asn Asp Ala Tyr Val His Ala Thr Pro Leu Ile Arg Arg Leu
                325                 330                 335

Ala Arg Glu Phe Gly Val Asn Leu Ala Lys Val Lys Gly Thr Gly Arg
            340                 345                 350

Lys Gly Arg Ile Leu Arg Glu Asp Val Gln Ala Tyr Val Lys Glu Ala
        355                 360                 365

Ile Lys Arg Ala Glu Ala Ala Pro Ala Ala Thr Gly Gly Gly Ile Pro
370                 375                 380

Gly Met Leu Pro Trp Pro Lys Val Asp Phe Ser Lys Phe Gly Glu Ile
385                 390                 395                 400

Glu Glu Val Glu Leu Gly Arg Ile Gln Lys Ile Ser Gly Ala Asn Leu
            405                 410                 415

Ser Arg Asn Trp Val Met Ile Pro His Val Thr His Phe Asp Lys Thr
            420                 425                 430

Asp Ile Thr Glu Leu Glu Ala Phe Arg Lys Gln Gln Asn Glu Glu Ala
        435                 440                 445

Ala Lys Arg Lys Leu Asp Val Lys Ile Thr Pro Val Val Phe Ile Met
    450                 455                 460

Lys Ala Val Ala Ala Ala Leu Glu Gln Met Pro Arg Phe Asn Ser Ser
465                 470                 475                 480

Leu Ser Glu Asp Gly Gln Arg Leu Thr Leu Lys Lys Tyr Ile Asn Ile
            485                 490                 495

Gly Val Ala Val Asp Thr Pro Asn Gly Leu Val Val Pro Val Phe Lys
            500                 505                 510

Asp Val Asn Lys Lys Gly Ile Ile Glu Leu Ser Arg Glu Leu Met Thr
        515                 520                 525

Ile Ser Lys Lys Ala Arg Asp Gly Lys Leu Thr Ala Gly Glu Met Gln
    530                 535                 540

Gly Gly Cys Phe Thr Ile Ser Ser Ile Gly Gly Leu Gly Thr Thr His
545                 550                 555                 560

Phe Ala Pro Ile Val Asn Ala Pro Glu Val Ala Ile Leu Gly Val Ser
            565                 570                 575

Lys Ser Ala Met Glu Pro Val Trp Asn Gly Lys Glu Phe Val Pro Arg
            580                 585                 590

Leu Met Leu Pro Ile Ser Leu Ser Phe Asp His Arg Val Ile Asp Gly
        595                 600                 605

Ala Asp Gly Ala Arg Phe Ile Thr Ile Ile Asn Asn Thr Leu Ser Asp
    610                 615                 620

Ile Arg Arg Leu Val Met
625                 630
```

<210> SEQ ID NO 51
<211> LENGTH: 1893
<212> TYPE: DNA
<213> ORGANISM: Escherichia coli

<400> SEQUENCE: 51

| | | | | | |
|---|---|---|---|---|---|
| atggctatcg | aaatcaaagt | accggacatc | ggggctgatg | aagttgaaat | caccgagatc | 60 |
| ctggtcaaag | tgggcgacaa | agttgaagcc | gaacagtcgc | tgatcaccgt | agaaggcgac | 120 |
| aaagcctcta | tggaagttcc | gtctccgcag | gcgggtatcg | ttaaagagat | caaagtctct | 180 |
| gttggcgata | aaacccagac | cggcgcactg | attatgattt | tcgattccgc | cgacggtgca | 240 |
| gcagacgctc | cacctgctca | ggcagaagag | aagaaagaag | cagctccggc | agcagcacca | 300 |
| gcggctgcgg | cggcaaaaga | cgttaacgtt | ccggatatcg | cagcgacga | agttgaagtg | 360 |
| accgaaatcc | tggtgaaagt | tggcgataaa | gttgaagctg | aacagtcgct | gatcaccgta | 420 |
| gaaggcgaca | aggcttctat | ggaagttccg | gctccgtttg | ctggcaccgt | gaaagagatc | 480 |
| aaagtgaacg | tgggtgacaa | agtgtctacc | ggctcgctga | ttatggtctt | cgaagtcgcg | 540 |
| ggtgaagcag | gcgcggcagc | tccggccgct | aaacaggaag | cagctccggc | agcggcccct | 600 |
| gcaccagcgg | ctggcgtgaa | agaagttaac | gttccggata | tcggcggtga | cgaagttgaa | 660 |
| gtgactgaag | tgatggtgaa | agtgggcgac | aaagttgccg | ctgaacagtc | actgatcacc | 720 |
| gtagaaggcg | acaaagcttc | tatggaagtt | ccggcgccgt | ttgcaggcgt | cgtgaaggaa | 780 |
| ctgaaagtca | acgttggcga | taaagtgaaa | actggctcgc | tgattatgat | cttcgaagtt | 840 |
| gaaggcgcag | cgcctgcggc | agctcctgcg | aaacaggaag | cggcagcgcc | ggcaccggca | 900 |
| gcaaaagctg | aagccccggc | agcagcacca | gctgcgaaag | cggaaggcaa | atctgaattt | 960 |
| gctgaaaacg | acgcttatgt | tcacgcgact | ccgctgatcc | gccgtctggc | acgcgagttt | 1020 |
| ggtgttaacc | ttgcgaaagt | gaagggcact | ggccgtaaag | gtcgtatcct | gcgcgaagac | 1080 |
| gttcaggctt | acgtgaaaga | agctatcaaa | cgtgcagaag | cagctccggc | agcgactggc | 1140 |
| ggtggtatcc | ctggcatgct | gccgtggccg | aaggtggact | cagcaagtt | tggtgaaatc | 1200 |
| gaagaagtgg | aactgggccg | catccagaaa | atctctggtg | cgaacctgag | ccgtaactgg | 1260 |
| gtaatgatcc | cgcatgttac | tcacttcgac | aaaaccgata | tcaccgagtt | ggaagcgttc | 1320 |
| cgtaaacagc | agaacgaaga | agcggcgaaa | cgtaagctgg | atgtgaagat | caccccggtt | 1380 |
| gtcttcatca | tgaaagccgt | tgctgcagct | cttgagcaga | tgcctcgctt | caatagttcg | 1440 |
| ctgtcggaag | acggtcagcg | tctgaccctg | aagaaataca | tcaacatcgg | tgtggcggtg | 1500 |
| gatacccga | acggtctggt | tgttccggta | ttcaaagacg | tcaacaagaa | aggcatcatc | 1560 |
| gagctgtctc | gcgagctgat | gactatttct | aagaaagcgc | gtgacggtaa | gctgactgcg | 1620 |
| ggcgaaatgc | agggcggttg | cttcaccatc | tccagcatcg | gcggcctggg | tactacccac | 1680 |
| ttcgcgccga | ttgtgaacgc | gccggaagtg | gctatcctcg | gcgtttccaa | gtccgcgatg | 1740 |
| gagccggtgt | ggaatggtaa | agagttcgtg | ccgcgtctga | tgctgccgat | ttctctctcc | 1800 |
| ttcgaccacc | gcgtgatcga | cggtgctgat | ggtgcccgtt | tcattaccat | cattaacaac | 1860 |
| acgctgtctg | acattcgccg | tctggtgatg | taa | | | 1893 |

<210> SEQ ID NO 52
<211> LENGTH: 474
<212> TYPE: PRT
<213> ORGANISM: Escherichia coli

<400> SEQUENCE: 52

-continued

```
Met Ser Thr Glu Ile Lys Thr Gln Val Val Val Leu Gly Ala Gly Pro
1               5                   10                  15
Ala Gly Tyr Ser Ala Ala Phe Arg Cys Ala Asp Leu Gly Leu Glu Thr
            20                  25                  30
Val Ile Val Glu Arg Tyr Asn Thr Leu Gly Gly Val Cys Leu Asn Val
        35                  40                  45
Gly Cys Ile Pro Ser Lys Ala Leu Leu His Val Ala Lys Val Ile Glu
    50                  55                  60
Glu Ala Lys Ala Leu Ala Glu His Gly Ile Val Phe Gly Glu Pro Lys
65                  70                  75                  80
Thr Asp Ile Asp Lys Ile Arg Thr Trp Lys Glu Lys Val Ile Asn Gln
                85                  90                  95
Leu Thr Gly Gly Leu Ala Gly Met Ala Lys Gly Arg Lys Val Lys Val
            100                 105                 110
Val Asn Gly Leu Gly Lys Phe Thr Gly Ala Asn Thr Leu Glu Val Glu
        115                 120                 125
Gly Glu Asn Gly Lys Thr Val Ile Asn Phe Asp Asn Ala Ile Ile Ala
    130                 135                 140
Ala Gly Ser Arg Pro Ile Gln Leu Pro Phe Ile Pro His Glu Asp Pro
145                 150                 155                 160
Arg Ile Trp Asp Ser Thr Asp Ala Leu Glu Leu Lys Glu Val Pro Glu
                165                 170                 175
Arg Leu Leu Val Met Gly Gly Gly Ile Ile Gly Leu Glu Met Gly Thr
            180                 185                 190
Val Tyr His Ala Leu Gly Ser Gln Ile Asp Val Val Glu Met Phe Asp
        195                 200                 205
Gln Val Ile Pro Ala Ala Asp Lys Asp Ile Val Lys Val Phe Thr Lys
    210                 215                 220
Arg Ile Ser Lys Lys Phe Asn Leu Met Leu Glu Thr Lys Val Thr Ala
225                 230                 235                 240
Val Glu Ala Lys Glu Asp Gly Ile Tyr Val Thr Met Glu Gly Lys Lys
                245                 250                 255
Ala Pro Ala Glu Pro Gln Arg Tyr Asp Ala Val Leu Val Ala Ile Gly
            260                 265                 270
Arg Val Pro Asn Gly Lys Asn Leu Asp Ala Gly Lys Ala Gly Val Glu
        275                 280                 285
Val Asp Asp Arg Gly Phe Ile Arg Val Asp Lys Gln Leu Arg Thr Asn
    290                 295                 300
Val Pro His Ile Phe Ala Ile Gly Asp Ile Val Gly Gln Pro Met Leu
305                 310                 315                 320
Ala His Lys Gly Val His Glu Gly His Val Ala Ala Glu Val Ile Ala
                325                 330                 335
Gly Lys Lys His Tyr Phe Asp Pro Lys Val Ile Pro Ser Ile Ala Tyr
            340                 345                 350
Thr Glu Pro Glu Val Ala Trp Val Gly Leu Thr Glu Lys Glu Ala Lys
        355                 360                 365
Glu Lys Gly Ile Ser Tyr Glu Thr Ala Thr Phe Pro Trp Ala Ala Ser
    370                 375                 380
Gly Arg Ala Ile Ala Ser Asp Cys Ala Asp Gly Met Thr Lys Leu Ile
385                 390                 395                 400
Phe Asp Lys Glu Ser His Arg Val Ile Gly Gly Ala Ile Val Gly Thr
                405                 410                 415
Asn Gly Gly Glu Leu Leu Gly Glu Ile Gly Leu Ala Ile Glu Met Gly
```

```
              420             425             430
Cys Asp Ala Glu Asp Ile Ala Leu Thr Ile His Ala His Pro Thr Leu
        435                     440                     445

His Glu Ser Val Gly Leu Ala Ala Glu Val Phe Glu Gly Ser Ile Thr
    450                     455                     460

Asp Leu Pro Asn Pro Lys Ala Lys Lys Lys
465                 470
```

<210> SEQ ID NO 53
<211> LENGTH: 1425
<212> TYPE: DNA
<213> ORGANISM: Escherichia coli

<400> SEQUENCE: 53

```
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta aagcactgct gcacgtagca     180
aaagttatcg aagaagccaa agcgctggct gaacacggta tcgtcttcgg cgaaccgaaa     240
accgatatcg acaagattcg tacctggaaa gagaaagtga tcaatcagct gaccggtggt     300
ctggctggta tggcgaaagg ccgcaaagtc aaagtggtca acggtctggg taaattcacc     360
ggggctaaca ccctggaagt tgaaggtgag aacggcaaaa ccgtgatcaa cttcgacaac     420
gcgatcattg cagcgggttc tcgcccgatc caactgccgt ttattccgca tgaagatccg     480
cgtatctggg actccactga cgcgctgaaa ctgaaagaag taccagaacg cctgctggta     540
atgggtggcg gtatcatcgg tctggaaatg ggcaccgttt accacgcgct gggttcacag     600
attgacgtgg ttgaaatgtt cgaccaggtt atcccggcag ctgacaaaga catcgttaaa     660
gtcttcacca gcgtatcag caagaaattc aacctgatgc tggaaaccaa agttaccgcc     720
gttgaagcga agaagacgg catttatgtg acgatggaag cgaaaaaagc acccgctgaa     780
ccgcagcgtt acgacgccgt gctggtagcg attggtcgtg tgccgaacgg taaaaacctc     840
gacgcaggca agcaggcgt ggaagttgac gaccgtggtt tcatccgcgt tgacaaacag     900
ctgcgtacca acgtaccgca catctttgct atcggcgata tcgtcggtca accgatgctg     960
gcacacaaag tgttcacga aggtcacgtt gccgctgaag ttatcgccgg taagaaacac    1020
tacttcgatc cgaaagttat cccgtccatc gcctataccg aaccagaagt tgcatgggtg    1080
ggtctgactg agaagaagc gaaagagaaa ggcatcagct atgaaaccgc caccttcccg    1140
tgggctgctt ctggtcgtgc tatcgcttcc gactgcgcag acggtatgac caagctgatt    1200
ttcgacaaag aatctcaccg tgtgatcggt ggtgcgattg tcggtactaa cggcggcgag    1260
ctgctgggtg aaatcggcct ggcaatcgaa atgggttgtg atgctgaaga catcgcactg    1320
accatccacg cgcacccgac tctgcacgag tctgtgggcc tggcggcaga agtgttcgaa    1380
ggtagcatta ccgacctgcc gaacccgaaa gcgaagaaga agtag                     1425
```

<210> SEQ ID NO 54
<211> LENGTH: 25
<212> TYPE: DNA
<213> ORGANISM: Artificial Sequence
<220> FEATURE:
<223> OTHER INFORMATION: Synthetic (primer)

<400> SEQUENCE: 54

```
aaatggaatg gcgcctagac aatcc                                              25
```

<210> SEQ ID NO 55
<211> LENGTH: 24
<212> TYPE: DNA
<213> ORGANISM: Artificial Sequence
<220> FEATURE:
<223> OTHER INFORMATION: Synthetic (primer)

<400> SEQUENCE: 55
cacttccctt atggatgctc aagg                                              24

<210> SEQ ID NO 56
<211> LENGTH: 46
<212> TYPE: DNA
<213> ORGANISM: Artificial Sequence
<220> FEATURE:
<223> OTHER INFORMATION: Synthetic (MD-616)

<400> SEQUENCE: 56
aaagtgtaaa gcctgggaac aacaagaccc atcatagttt gccccc                      46

<210> SEQ ID NO 57
<211> LENGTH: 36
<212> TYPE: DNA
<213> ORGANISM: Artificial Sequence
<220> FEATURE:
<223> OTHER INFORMATION: Synthetic (MD-618)

<400> SEQUENCE: 57
gttcttctaa tcagaattgg ttaattggtt gtaaca                                 36

<210> SEQ ID NO 58
<211> LENGTH: 40
<212> TYPE: DNA
<213> ORGANISM: Artificial Sequence
<220> FEATURE:
<223> OTHER INFORMATION: Synthetic (MD-615)

<400> SEQUENCE: 58
gcgtaatagc gaagaggggc gttttttccat aggctccgcc                            40

<210> SEQ ID NO 59
<211> LENGTH: 40
<212> TYPE: DNA
<213> ORGANISM: Artificial Sequence
<220> FEATURE:
<223> OTHER INFORMATION: Synthetic (MD-617)

<400> SEQUENCE: 59
gttcaatcat aacacccctt gtattactgt ttatgtaagc                             40

<210> SEQ ID NO 60
<211> LENGTH: 31
<212> TYPE: DNA
<213> ORGANISM: Artificial Sequence
<220> FEATURE:
<223> OTHER INFORMATION: Synthetic (MD-619)

<400> SEQUENCE: 60
gggtgttatg attgaacaag atggattgca c                                      31

<210> SEQ ID NO 61
<211> LENGTH: 39
<212> TYPE: DNA
<213> ORGANISM: Artificial Sequence
<220> FEATURE:
<223> OTHER INFORMATION: Synthetic (MD-620)

<400> SEQUENCE: 61
attctgatta gaagaactcg tcaagaaggc gatagaagg                            39

<210> SEQ ID NO 62
<211> LENGTH: 17
<212> TYPE: DNA
<213> ORGANISM: Artificial Sequence
<220> FEATURE:
<223> OTHER INFORMATION: Synthetic (LacZa-NR)

<400> SEQUENCE: 62
cctcttcgct attacgc                                                   17

<210> SEQ ID NO 63
<211> LENGTH: 21
<212> TYPE: DNA
<213> ORGANISM: Artificial Sequence
<220> FEATURE:
<223> OTHER INFORMATION: Synthetic (MD-404)

<400> SEQUENCE: 63
cccaggcttt acactttatg c                                              21

<210> SEQ ID NO 64
<211> LENGTH: 47
<212> TYPE: DNA
<213> ORGANISM: Artificial Sequence
<220> FEATURE:
<223> OTHER INFORMATION: Synthetic (MD-627)

<400> SEQUENCE: 64
gccaccgcgg tggagctcat ttagcggatg attctcgttc aacttcg                  47

<210> SEQ ID NO 65
<211> LENGTH: 32
<212> TYPE: DNA
<213> ORGANISM: Artificial Sequence
<220> FEATURE:
<223> OTHER INFORMATION: Synthetic (MD-628)

<400> SEQUENCE: 65
ttttatttgc aaaaacggcc gaaaccatcc ct                                  32

<210> SEQ ID NO 66
<211> LENGTH: 40
<212> TYPE: DNA
<213> ORGANISM: Artificial Sequence
<220> FEATURE:
<223> OTHER INFORMATION: Synthetic (MD-629)

<400> SEQUENCE: 66 ccgttttgc aaataaaacg aaaggctcag tcgaaagact                            40

<210> SEQ ID NO 67
<211> LENGTH: 43
<212> TYPE: DNA
<213> ORGANISM: Artificial Sequence
<220> FEATURE:
<223> OTHER INFORMATION: Synthetic (MD-630)

<400> SEQUENCE: 67
gaacaaaagc tggagctacc gtatctgtgg ggggatggct tgt                      43

<210> SEQ ID NO 68

```
<211> LENGTH: 50
<212> TYPE: DNA
<213> ORGANISM: Artificial Sequence
<220> FEATURE:
<223> OTHER INFORMATION: Synthetic (J0180)

<400> SEQUENCE: 68
ctatagggcg aattgggtac ctgcgttaat aaaggtggag aataagttgt            50

<210> SEQ ID NO 69
<211> LENGTH: 41
<212> TYPE: DNA
<213> ORGANISM: Artificial Sequence
<220> FEATURE:
<223> OTHER INFORMATION: Synthetic (MD-1081)

<400> SEQUENCE: 69
tgacctcctc tcgagtttag attccctaaa cttttatcga g                     41

<210> SEQ ID NO 70
<211> LENGTH: 36
<212> TYPE: DNA
<213> ORGANISM: Artificial Sequence
<220> FEATURE:
<223> OTHER INFORMATION: Synthetic (MD-1082)

<400> SEQUENCE: 70
aaactcgaga ggaggtcatg atgagtactg aaatca                           36

<210> SEQ ID NO 71
<211> LENGTH: 36
<212> TYPE: DNA
<213> ORGANISM: Artificial Sequence
<220> FEATURE:
<223> OTHER INFORMATION: Synthetic (MD-1083)

<400> SEQUENCE: 71
ttattcctcc tacttcttct tcgctttcgg gttcgg                           36

<210> SEQ ID NO 72
<211> LENGTH: 37
<212> TYPE: DNA
<213> ORGANISM: Artificial Sequence
<220> FEATURE:
<223> OTHER INFORMATION: Synthetic (MD-1084)

<400> SEQUENCE: 72
aagaagtagg aggaataacc catgtcagaa cgtttcc                          37

<210> SEQ ID NO 73
<211> LENGTH: 22
<212> TYPE: DNA
<213> ORGANISM: Artificial Sequence
<220> FEATURE:
<223> OTHER INFORMATION: Synthetic (MD-1085)

<400> SEQUENCE: 73
ttttacctcc tacgccagac gc                                          22

<210> SEQ ID NO 74
<211> LENGTH: 26
<212> TYPE: DNA
<213> ORGANISM: Artificial Sequence
<220> FEATURE:
<223> OTHER INFORMATION: Synthetic (MD-1086)

<400> SEQUENCE: 74
```

```
tctggcgtag gaggtaaaag aataat                                        26

<210> SEQ ID NO 75
<211> LENGTH: 43
<212> TYPE: DNA
<213> ORGANISM: Artificial Sequence
<220> FEATURE:
<223> OTHER INFORMATION: Synthetic (MD-1087)

<400> SEQUENCE: 75
ggtggcggcc gctctagatt acatcaccag acggcgaatg tca                     43

<210> SEQ ID NO 76
<211> LENGTH: 47
<212> TYPE: DNA
<213> ORGANISM: Artificial Sequence
<220> FEATURE:
<223> OTHER INFORMATION: Synthetic (primer)

<400> SEQUENCE: 76
caggtcgact ctagaggatc cgtgtcaccg atcattcgta aattgag                 47

<210> SEQ ID NO 77
<211> LENGTH: 46
<212> TYPE: DNA
<213> ORGANISM: Artificial Sequence
<220> FEATURE:
<223> OTHER INFORMATION: Synthetic (primer)

<400> SEQUENCE: 77
gtaaaacgac ggccagtgaa ttcttaggaa tcatgaaggg ggaggg                  46
```